United States Patent
Zhang et al.

(10) Patent No.: US 11,538,553 B2
(45) Date of Patent: Dec. 27, 2022

(54) SYSTEMS AND METHODS OF FRAGMENT-CENTRIC TOPOGRAPHICAL MAPPING (FCTM) TO TARGET PROTEIN-PROTEIN INTERACTIONS

(71) Applicant: NEW YORK UNIVERSITY, New York, NY (US)

(72) Inventors: Yingkai Zhang, New York, NY (US); David Rooklin, Brooklyn, NY (US)

(73) Assignee: New York University, New York, NY (US)

( * ) Notice: Subject to any disclaimer, the term of this patent is extended or adjusted under 35 U.S.C. 154(b) by 1430 days.

(21) Appl. No.: 15/559,719

(22) PCT Filed: Mar. 22, 2016

(86) PCT No.: PCT/US2016/023620
§ 371 (c)(1),
(2) Date: Sep. 19, 2017

(87) PCT Pub. No.: WO2016/154220
PCT Pub. Date: Sep. 29, 2016

(65) Prior Publication Data
US 2018/0101641 A1   Apr. 12, 2018

Related U.S. Application Data

(60) Provisional application No. 62/137,035, filed on Mar. 23, 2015.

(51) Int. Cl.
G16B 15/30 (2019.01)
G16B 15/00 (2019.01)

(52) U.S. Cl.
CPC .............. *G16B 15/30* (2019.02); *G16B 15/00* (2019.02)

(58) Field of Classification Search
CPC ................................ G16B 15/30; G16B 15/00
USPC ........................................................ 702/19
See application file for complete search history.

(56) References Cited

U.S. PATENT DOCUMENTS

| | | |
|---|---|---|
| 2002/0015038 A1 | 2/2002 | Patel et al. |
| 2009/0006059 A1 | 1/2009 | Arora et al. |
| 2010/0183226 A1 | 7/2010 | Kim et al. |

FOREIGN PATENT DOCUMENTS

WO   WO-01/09615 A2   2/2001

OTHER PUBLICATIONS

Aguilar, et al., "A potent and highly efficacious Bcl-2/Bcl-xL inhibitor," Journal of Medicinal Chemistry 56(7), pp. 3048-3067 (2013).
An, et al., "Pocketome via comprehensive identification and classification of ligand binding envelopes," Molecular & Cellular Proteomics 4(6), pp. 752-761 (2005).
Arkin, "Protein-protein interactions and cancer: small molecules going in for the kill," Current Opinion in Chemical Biology 9(3), pp. 317-324 (2005).
Arkin, et al., "Binding of small molecules to an adaptive protein-protein interface," Proceedings of the National Academy of Sciences 100(4), pp. 1603-1608 (2003).
Barber, et al., "The quickhull algorithm for convex hulls," ACM Transactions on Mathematical Software 22(4), pp. 469-483 (1996).
Basse, et al., "2P2Idb: a structural database dedicated to orthosteric modulation of protein-protein interactions," Nucleic Acids Research 41 (D1), pp. D824-D827 (2013).
Binkowski, et al., "CASTp: Computed Atlas of Surface Topography of proteins," Nucleic Acids Research 31(13), pp. 3352-3355 (2003).
Bista, "Transient Protein States in Designing Inhibitors of the MDM2-p53 Interaction," Structure 21(12), pp. 2143-2151 (2013).
Blazer & Neubig, "Small Molecule Protein-Protein Interaction Inhibitors as CNS Therapeutic Agents: Current Progress and Future Hurdles," Neuropsychopharmacology 34, pp. 126-141 (2009).
Bogan & Thorn, "Anatomy of hot spots in protein interfaces," Journal of Molecular Biology 280(1), pp. 1-9 (1998).
Bourgeas, et al., "Atomic Analysis of Protein-Protein Interfaces with Known Inhibitors: The 2P2I Database," PLoS One 5(3), e9598, 11 pages (2010).
Brady & Stouten, "Fast prediction and visualization of protein binding pockets with PASS," Journal of Computer-Aided Molecular Design 14(4), pp. 383-401 (2000).
Braisted, et al., "Discovery of a Potent Small Molecule IL-2 Inhibitor through Fragment Assembly," Journal of the American Chemical Society 125(13), pp. 3714-3715 (2003).
Brenke, et al., "Fragment-based identification of druggable "hot spots" of proteins using Fourier domain correlation techniques," Bioinformatics 25(5), pp. 621-627 (2009).
Cao & Li, "Improved protein-ligand binding affinity prediction by using a curvature-dependent surface-area model," Bioinformatics 30(12), pp. 1674-1680 (2014).
Chang, et al., "MEDock: a web server for efficient prediction of ligand binding sites based on a novel optimization algorithm," Nucleic Acids Research 33(Supp.), pp. W233-W238 (2005).
Cheng, et al., "Structure-based maximal affinity model predicts small-molecule druggability," Nature Biotechnology 25, pp. 71-75 (2007).
Chothia & Janin, "Principles of protein-protein recognition," Nature 256, pp. 705-708 (1975).

(Continued)

*Primary Examiner* — Jerry Lin
(74) *Attorney, Agent, or Firm* — Foley & Lardner LLP

(57) ABSTRACT

A system for identifying and evaluating a pocket of a protein includes performing a Voronoi tessellation and developing a Voronoi diagram of a surface of the protein. All alpha-spheres on the surface of the protein are identified. The alpha-spheres are filtered based on radius and remaining alpha-spheres are clustered into alpha-clusters. At least one alpha-cluster is selected for quantitative evaluation. Alpha-sphere contact atoms are determined for a plurality of interaction points of the pocket. A Delaunay triangulation of the four contact atoms of each interaction point is performed. A plurality of alpha-spaces for each interaction point are determined. An alpha-atom and an alpha-atom contact surface area (ACSA) of each interaction point is determined. The pocket is ranked, a pocket-fragment complementarity is determined, and the pocket is matched between various conformations of the proteins.

19 Claims, 23 Drawing Sheets

(56) References Cited

OTHER PUBLICATIONS

Cochran, "Antagonists of protein-protein interactions," Chemistry & Biology 7(4), pp. R85-R94 (2000).

Congreve, et al., "Recent Developments in Fragment-Based Drug Discovery," Journal of Medicinal Chemistry 51(13), pp. 3661-3680 (2008).

Dawson, et al., "Synthesis of proteins by native chemical ligation," Science 266(5186), pp. 776-779 (1994).

Durrant, et al., "POVME 2.0: An Enhanced Tool for Determining Pocket Shape and Volume Characteristics," Journal of Chemical Theory and Computation 10(11), pp. 5047-5056 (2014).

Eyisch & Helms, "Transient pockets on protein surfaces involved in protein-protein interaction," Journal of Medicinal Chemistry 50(15), pp. 3457-3464 (2007).

Fuller, et al., "Predicting druggable binding sites at the protein-protein interface," Drug Discovery Today 14(3-4), pp. 155-161 (2009).

Goldberg & Bona, "Dimeric MHC-peptides inserted into an immunoglobulin scaffold as new immunotherapeutic agents," Journal of Cellular and Molecular Medicine 15(9), pp. 1822-1832 (2011).

Gourdreau, et al., "Optimization and determination of the absolute configuration of a series of potent inhibitors of human papillomavirus type-11 E1-E2 protein-protein interaction: A combined medicinal chemistry, NMR and computational chemistry approach," Bioorganic & Medicinal Chemistry 15(7), pp. 2690-2700 (2007).

Halgern, "Identifying and characterizing binding sites and assessing druggability," Journal of Chemical Information and Modeling 49(2), pp. 377-389 (2009).

Hall, et al., "Hot Spot Analysis for Driving the Development of Hits into Leads in Fragment-Based Drug Discovery," Journal of Chemical Information and Modeling 52(1), pp. 199-209 (2012).

Hayouka, et al., "Inhibiting HIV-1 integrase by shifting its oligomerization equilibrium," Proceedings of the National Academy of Sciences 104(20), pp. 8316-8321 (2007).

He, et al., "Small-Molecule Inhibition of TNF-a," Science 310(5750), pp. 1022-1025 (2005).

Hendlich, et al., "LIGSITE: automatic and efficient detection of potential small molecule-binding sites in proteins," Journal of Molecular Graphics and Modelling 15(6), pp. 359-363 (1997).

Hernandez, et al., "SITEHOUND-web: a server for ligand binding site identification in protein structures," Nucleic Acids Research 31(Supp.), pp. W413-W416 (2009).

Huang & Jacobson, "Binding-site assessment by virtual fragment screening," PLoS One 5(4), e10109, 10 pages (2010).

Huang & Schroeder, "LIGSITEcsc: predicting ligand binding sites using the Connolly surface and degree of conservation," BMC Structural Biology 6(19), 11 pages (2006).

Kastritis & Bonvin, "On the binding affinity of macromolecular interactions: daring to ask why proteins interact," Journal of the Royal Society Interface 10(79), 20120835, 27 pages (2013).

Khoo, et al., "Drugging the p53 pathway: understanding the route to clinical efficacy," Nature Reviews Drug Discovery 13, pp. 217-236 (2014).

Kortemme, et al., "Computational Alanine Scanning of Protein-Protein Interfaces," Science's STKE 2004(219), pl2, 8 pages (2004).

Kozakov, et al., "Structural conservation of druggable hotspots in protein-protein interfaces," Proceedings of the National Academy of Sciences 108(33), pp. 13528-13533 (2011).

Kussie, et al., "Structure of the MDM2 oncoprotein bound to the p53 tumor suppressor transactivation domain," Science 274(5289), pp. 948-953 (1996).

Lao, et al., "In vivo modulation of hypoxia-inducible signaling by topographical helix mimetics," Proceedings of the National Academy of Sciences 111(21), pp. 7531-7536 (2014).

Laskowski, "SURFNET: A program for visualizing molecular surfaces, cavities, and intermolecular interactions," Journal of Molecular Graphics 13(5), pp. 323-330 (1995).

Laurie & Jackson, "Methods for the Prediction of Protein-Ligand Binding Sites for Structure-Based Drug Design and Virtual Ligand Screening," Current Protein and Peptide Science 7(5), pp. 395-406 (2006).

Laurie & Jackson, "Q-SiteFinder: an energy-based method for the prediction of protein-ligand binding sites," Bioinformatics 21(9), pp. 1908-1916 (2005).

Levvit & Banaszak, "POCKET: a computer graphics method for identifying and displaying protein cavities and their surrounding amino acids," Journal of Molecular Graphics 10(4), pp. 229-234 (1992).

Li, et al., "Computational method to identify druggable binding sites that target protein-protein interactions," Journal of Chemical Information and Modelling 54(5), pp. 1391-1400 (2014).

Li, et al., "Systematic Mutational Analysis of Peptide Inhibition of the p53-MDM2/MDMX Interactions," Journal of Moleculary Biology 398(2), pp. 200-213 (2010).

Liang, et al., "Anatomy of protein pockets and cavities: Measurement of binding site geometry and implications for ligand design," Protein Science 7(9), pp. 1884-1897 (1998).

Liu, et al., "A left-handed solution to peptide inhibition of the p53-MDM2 interaction," Angewandte Chemie 49(21), pp. 3649-3652 (2010).

Marks, et al., "Protein 3D Structure Computed from Evolutionary Sequence Variation," PLoS One 6(12), e28766, 20 pages (2011).

Moreira, et al., "Hot spots—a review of the protein-protein interface determinant amino-acid residues," Proteins 68(4), pp. 803-812 (2007).

Mullard, "Protein-protein interaction inhibitors get into the groove," Nature Reviews Drug Discovery 11, pp. 173-175 (2012).

Murray & Rees, "The rise of fragment-based drug discovery," Nature Chemistry 1, pp. 187-192 (2009).

Nero, et al., "Oncogenic protein interfaces: small molecules, big challenges," Nature Reviews Cancer 14, pp. 248-262 (2014).

Ngan, et al., "FTSite: high accuracy detection of ligand binding sites on unbound protein structures," Bioinformatics 28(2), pp. 286-287 (2012).

Nisius, et al., "Structure-based computational analysis of protein binding sites for function and druggability prediction," Journal of Biotechnology 159(3), pp. 123-134 (2012).

Paramo, et al., "Efficient Characterization of Protein Cavities within Molecular Simulation Trajectories: trj_cavity," Journal of Chemical Theory and Computation 10(5), pp. 2151-2164 (2014).

Peters, et al., "The Automatic Search for Ligand Binding Sites in Proteins of Known Three-dimensional Structure Using only Geometric Criteria,"Journal of Molecular Biology 256(1), pp. 201-213 (1996).

Poupon, "Voronoi and Voronoi-related tessellations in studies of protein structure and interaction," Current Opinion in Structural Biology 14(2), pp. 233-241 (2004).

Raimundo, et al., "Integrating Fragment Assembly and Biophysical Methods in the Chemical Advancement of Small-Molecule Antagonists of IL-2:? An Approach for Inhibiting Protein-Protein Interactions," Journal of Medicinal Chemistry 47(12), pp. 3111-3130 (2004).

Raj, et al., "Plucking the high hanging fruit: a systematic approach for targeting protein-protein interactions," Bioorganic & Medicinal Chemistry 21(14), pp. 4051-4057 (2013).

Rew, et al., "Structure-based design of novel inhibitors of the MDM2-p53 interaction," Journal of Medicinal Chemistry 55(11), pp. 4936-4954 (2012).

Richards, "The interpretation of protein structures: Total volume, group volume distributions and packing density," Journal of Molecular Biology 82(1), pp. 1-14 (1974).

Rush, et al., "A shape-based 3-D scaffold hopping method and its application to a bacterial protein-protein interaction," Journal of Medicinal Chemistry 48(5), pp. 1489-1495 (2005).

Sattler, et al., "Structure of Bcl-xL-Bak Peptide Complex: Recognition Between Regulators of Apoptosis," Science 275(5302), pp. 983-986 (1997).

Schmidtke & Barril, "Understanding and Predicting Druggability. A High-Throughput Method for Detection of Drug Binding Sites," Journal of Medicinal Chemistry 53(15), pp. 5858-5867 (2010).

(56) References Cited

OTHER PUBLICATIONS

Schmidtke, et al., "Large-scale comparison of four binding site detection algorithms," Journal of Chemical Information and Modeling 50(12), pp. 2191-2200 (2010).
Schmidtke, et al., "MDpocket: open-source cavity detection and characterization on molecular dynamics trajectories," Bioinformatics 27(23), pp. 3276-3285 (2011).
Shuker, et al., "Discovering High-Affinity Ligands for Proteins: SAR by NMR," Science 274(5292), pp. 1531-1534 (1996).
Spencer, "High-throughput screening of historic collections: Observations on file size, biological targets, and file diversity," Biotechnology and Bioengineering 61(1), pp. 61-67 (1998).
Sun, et al., "Discovery of AMG 232, a Potent, Selective, and Orally Bioavailable MDM2-p53 Inhibitor in Clinical Development," Journal of Medicinal Chemistry 57(4), pp. 1454-1472 (2014).
Sundaram, et al., "Specific Inhibition of p25/Cdk5 Activity by the Cdk5 Inhibitory Peptide Reduces Neurodegeneration In Vivo," Journal of Neurosciences 33(1), pp. 334-343 (2013).
Tsao, et al., "Discovery of novel inhibitors of the ZipA/FtsZ complex by NMR fragment screening coupled with structure-based design," Bioorganic & Medicinal Chemistry 14(23), pp. 7953-7961 (2006).
Uhrinova, et al., "Structure of free MDM2 N-terminal domain reveals conformational adjustments that accompany p53-binding," Journal of Molecular Biology 350(3), pp. 587-598 (2005).
Vassilev, et al., "n vivo activation of the p53 pathway by small-molecule antagonists of MDM2," Science 303(5659), pp. 844-848 (2004).
Weisel, et al., "PocketPicker: analysis of ligand binding-sites with shape descriptors," Chemistry Central Journal 1(7), 17 pages (2007).
Wells & McClendon, "Reaching for high-hanging fruit in drug discovery at protein-protein interfaces," Nature 450, pp. 1001-1009 (2007).
Whitty & Kumaravel, "Between a rock and a hard place?," Nature Chemical Biology 2, pp. 112-118 (2006).
Yu, et al., "Roll: a new algorithm for the detection of protein pockets and cavities with a rolling probe sphere," Bioinformatics 26(1), pp. 46-52 (2010).
Zerbe, et al., "Relationship between hot spot residues and ligand binding hot spots in protein-protein interfaces," Journal of Chemical Information and Modeling 52(8), pp. 2236-2244 (2012).
Zhan, et al., "An ultrahigh affinity d-peptide antagonist Of MDM2," Journal of Medicinal Chemistry 55(13), pp. 6237-6241 (2012).
International Search Report and Written Opinion for PCT/US2016/023620, dated Aug. 15, 2016, 14 pages.
Le Guilloux et al., "Fpocket: An open source platform for ligand pocket detection", <https://bmebioinformatics.biomedcentral.com/articles/10.1186/1471-2105-10-168>, Jun. 2, 2009, 19 pages.
Zhou et al., "Alpha shape and Delaunay triangulation in studies of protein-related interactions", Briefings in Bioinformatics, Nov. 27, 2012, 15(1):54-64.
Rooklin et al., "AlphaSpace: Fragment-Centric Topographical Mapping to Target Protein-Protein Interaction Interfaces", J. Chem. Inf. Model., Jul. 30, 2015, 55:1585-1599.

SYSTEMS AND METHODS OF FRAGMENT-CENTRIC TOPOGRAPHICAL MAPPING (FCTM) TO TARGET PROTEIN-PROTEIN INTERACTIONS

CROSS-REFERENCE TO RELATED APPLICATIONS

This application is the U.S. national phase application under 35 U.S.C. § 371 of International Application No. PCT/US2016/023620, filed Mar. 22, 2016, which claims priority to and benefit of U.S. Provisional Patent Application No. 62/137,035, filed Mar. 23, 2015, the entire disclosures of which are incorporated herein by reference.

TECHNICAL FIELD

The present disclosure relates generally to systems and methods for mapping a protein surface for the identification and evaluation of chemical fragment interaction regions and for the evaluation and optimization of bound chemical fragment candidates.

BACKGROUND

Various protein-protein interaction (PPI) inhibitors (iPPIs) are in development to treat cancer, neurodegenerative disease, autoimmune disease, arthritis, viral infection, bacterial infection, etc., and several have advanced into clinical trials and beyond. Historically PPI interfaces have been comparatively intractable drug targets. But over the last decade, traditional high-throughput screening (HTS) of drug-like compounds is being supplanted by a fragment-centric screening and lead-development approach known as fragment-based drug discovery (FBDD). FBDD aims to identify the affinity, not of full-sized compounds with promising affinity, but of small weakly binding chemical fragments, to be subsequently linked or extended into unique multi-fragment scaffolds.

In this way, FBDD untethers the discovery of new drugs from the screening libraries of preexisting drug programs. Fragment-based approaches have led to the discovery of several high-affinity inhibitors that are highly complementary to the distinct PPI interfaces they target. Potent fragment-based compounds tend to be somewhat larger than classical drugs, but they engage in multiple fragment-centric interactions to achieve therapeutically relevant binding, with some of the tightest PPI inhibitors attaining picomolar affinities.

The alanine scanning technique, commonly used to identify which residues interact most favorably in a PPI complex, also invokes a fragment-centric view of the PPI interface. The interactions between the hot spot side chains and the partner protein can be thought of as native fragment-like interactions. Biomimetic iPPIs are often designed specifically to preserve these hot spot interactions, and to optimize them. While identification of the important side chains can provide a good starting point for PPI inhibitor design, alanine scanning does not provide structural information about the surface involved in a hot spot interaction or the degree of complementarity between the surface and the side chain binding fragment. Thus from an inhibitor design perspective, whether using FBDD or the alanine scanning technique, it is of significant interest and importance to provide a fragment-centric structural characterization, or mapping, of PPI interfaces.

Mapping of PPI interfaces is closely related to the problem of ligand binding site detection. Over the years, a number of diverse algorithms have been developed for this purpose, which fall into four general categories: geometry-based, probe-based, grid-based, and docking-based. Some methods rely on the structure alone, while others incorporate energetic terms or sequence conservation into the pocket detection. However, since PPIs usually feature large and flat binding surfaces, without the deep pockets of typical drug targets, they pose a distinct challenge for geometry-based pocket-detection methods in providing a meaningful fragment-centric structural characterization. In particular, conventional cavity-centric methods are susceptible to: incomplete interface coverage, pocket expansion into solvent-inaccessible regions and, due to the comparatively subtle boundaries between some fragment-centric interaction regions, the over-consolidation of pocket space across multiple side chain or fragment interactions.

SUMMARY

Embodiments described herein relate generally to systems and methods for identification and ranking of fragments-centric interaction regions, and in particular to systems and methods that identify and evaluate one or more pockets of a protein and assess the complementarity of bound chemical fragments using alpha-atoms, alpha-spaces and alpha-clusters and evaluate the pocket for interaction with the chemical fragment.

In some embodiments, a method for mapping and evaluating protein surfaces includes performing a Voronoi tessellation of a protein structure. A Voronoi diagram of the surface of the protein is developed which includes a plurality of Voronoi vertices. All alpha-spheres on the surface of the protein are identified. A center of the alpha-spheres corresponds to the Voronoi vertices. The alpha-spheres are filtered based on radius to remove alpha-spheres having a radius below a minimum radius and above a maximum radius. The remaining alpha-spheres are clustered into alpha-clusters, which comprise localized pockets on the protein surface clustered using a linkage algorithm with optimized clustering parameters. At least one alpha-cluster is selected for quantitative evaluation which comprises the pocket of the protein. The pocket of the protein is displayed to a user.

In other embodiments, a method for evaluating a pocket of a protein includes determining sets of alpha-sphere contact atoms in a plurality of interaction points. The contact atoms include four atoms of the protein that are equidistant to a corresponding alpha-sphere, which represents a single interaction point. A Delaunay triangulation of the four contact atoms of each interaction point is performed. A plurality of alpha-spaces of the pocket are determined. Each alpha-space corresponds to a volume of a region defined by the Delaunay triangulation of the contact atoms of each interaction point. An alpha-atom of each interaction point is determined, and an alpha-atom contact surface area (ACSA) of each localized region the pocket is also determined. The pocket is ranked to determine a pocket score. The pocket score corresponds to a nonpolar-weighted alpha-space volume. A pocket-fragment complementarity is determined by discretely evaluating whether there is overlap for individual alpha-atoms. Pockets between various conformations of the protein are matched. An optimal chemical fragment for binding to the pocket of the protein is identified. The optimal chemical fragment is displayed to a user.

In still other embodiments, a system for identifying and evaluating a pocket of a protein to identify chemical fragments which can optimally bind to the pocket in a protein-protein-interaction includes a computing device. The computing device is specifically programmed for identifying and evaluating the pocket of the protein and is configured to performing a Voronoi tessellation of a protein structure. A Voronoi diagram of the surface of the protein is developed which includes a plurality of Voronoi vertices. All alpha-spheres on the surface of the protein are identified. A center of the alpha-spheres corresponds to the Voronoi vertices. The alpha-spheres are filtered based on radius to remove alpha-spheres having a radius below a minimum radius and above a maximum radius. The remaining alpha-spheres are clustered into alpha-clusters, which include localized pockets on the protein structure clustered using a linkage algorithm with optimized clustering parameters. At least one alpha-cluster is selected for quantitative evaluation which comprises the pocket of the protein.

Alpha-sphere contact atoms are determined in a plurality of interaction points. The contact atoms include four atoms of the protein that are equidistant to a corresponding alpha-sphere, which represents a single interaction point. A Delaunay triangulation of the four contact atoms of each interaction point is performed. A plurality of alpha-spaces of the pocket are determined. Each alpha-space corresponds to a volume of a region defined by the Delaunay triangulation of the contact atoms of each interaction point. An alpha-atom of each interaction point is determined, and an alpha-atom contact surface area (ACSA) of the pocket is also determined. The pocket is ranked to determine a pocket score. The pocket score corresponds to a nonpolar-weighted alpha-space volume. A pocket-fragment complementarity is determined by discretely evaluating whether there is overlap for individual alpha-atom. Pockets between various conformations of the protein are matched. An optimal chemical fragment for binding to the pocket of the protein is identified. The optimal chemical fragment is displayed to a user.

In some embodiments, a method for identifying druggable surface regions of a protein comprises identifying a plurality of pockets of the protein. All identified pockets of the plurality of pockets of the protein are quantified as core pockets, auxiliary pockets or minor pockets. Each isolated core pocket or each set of overlapping core pockets is designated as a community core. Each set of core pockets is expanded to include any overlapping auxiliary pockets. The expanded set of core pockets and auxiliary pockets define a pocket community, representing a druggable surface region of the protein.

In some embodiments, a method for mapping a surface of a protein comprises detecting all fragment-centric pockets of the protein at an interaction point. A pairwise pocket distance between a pair of pockets is calculated. A Jaccard distance between a plurality of pairs of pockets is also calculated. An n×n pairwise distance matrix is generated, where n is a total number of pockets at the interaction point. The pairwise pocket distance matrix is clustered into d-pockets using an average linkage criteria and a predetermined distance parameter.

In some embodiments, a non-transitory computer readable medium for identifying and evaluating a pocket of a protein, having instructions stored thereon that, when executed by a computing device, causes the computing device to perform operations comprising performing a Voronoi tessellation of a structure of the protein. A Voronoi diagram of the surface of the protein is developed which includes a plurality of Voronoi vertices. All alpha-spheres on the surface of the protein are identified. A center of the alpha-spheres corresponds to the Voronoi vertices. The alpha-spheres are filtered based on radius to remove alpha-spheres having a radius below a minimum radius and above a maximum radius. The remaining alpha-spheres are clustered into alpha-clusters, which include localized pockets on the protein structure clustered using a linkage algorithm with optimized clustering parameters. At least one alpha-cluster is selected for quantitative evaluation which comprises the pocket of the protein. Alpha-sphere contact atoms are determined in a plurality of interaction points. The contact atoms include four atoms of the protein that are equidistant to a corresponding alpha-sphere, which represents a single interaction point. A Delaunay triangulation of the four contact atoms of each interaction point is performed. A plurality of alpha-spaces of the pocket are determined. Each alpha-space corresponds to a volume of a region defined by the Delaunay triangulation of the contact atoms of each interaction point. An alpha-atom of each interaction point is determined, and an alpha-atom contact surface area (ACSA) of the pocket is also determined. The pocket is ranked to determine a pocket score. The pocket score corresponds to a nonpolar-weighted alpha-space volume. A pocket-fragment complementarity is determined by discretely evaluating whether there is overlap for individual alpha-atoms. Pockets between various conformations of the protein are matched. An optimal chemical fragment for binding to the pocket of the protein is identified. The optimal chemical fragment is displayed to a user.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

FIG. 4 panel (B) is an individual alpha-system including an alpha-sphere, alpha-atom, alpha-space and contact atoms; and FIG. 4 panel (C) is a schematic of an individual alpha-system in 3-dimensions.

Figure 1:
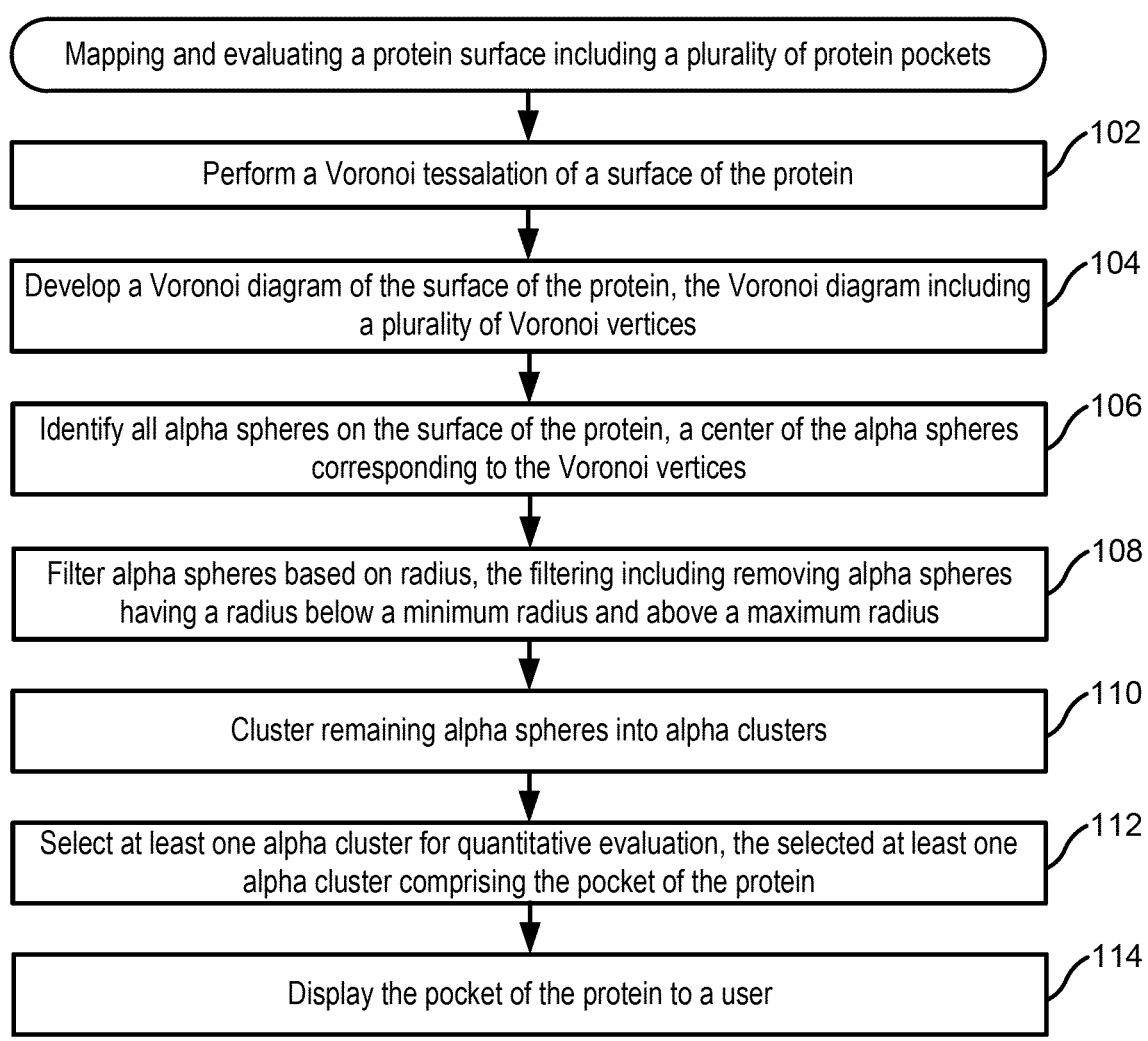
FIG. 1 is a schematic flow diagram of a method for identifying a pocket of a protein which can bind a chemical fragment in a PPI, according to an embodiment.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION OF VARIOUS EMBODIMENTS

Embodiments described herein relate generally to systems and methods for identification and ranking of fragment-centric interaction regions, and in particular to systems and methods that identify and evaluate one or more pockets of a protein and assess the complementarity of bound chemical fragments using alpha-atoms, alpha-spaces and alpha-clusters and evaluate the pocket for interaction with the chemical fragment.

Embodiments of the fragment-centric topographical methods for mapping proteins described herein provide several benefits including, for example: (1) providing enhanced interface coverage of the protein by localization of the protein pockets into solvent accessible, fragment-centric interaction regions; (2) providing a high resolution map of underutilized, targetable pocket space at a PPI interface; (3) employing a fast geometry-based approach to provide a comprehensive FCTM of the PPI interface; (4) ranking and facilitating the evaluation of complementarity of a pocket and chemical fragment using the concepts of alpha-space and alpha-atom to provide a high resolution map of underutilized, targetable pocket space at a PPI interface; and (5) providing to a user an optimal chemical fragment for binding with a particular protein.

As described herein, the term "alpha-sphere" refers to a geometric feature derived from the Voronoi diagram of a set of points in 3-dimensional space in which the alpha-sphere centers are defined at the vertices of the Voronoi tessellation.

As described herein, the term "alpha-space" refers to a volume of a region defined by the Delaunay triangulation of the contact atoms included in a localized region of a protein pocket. The alpha-space is the volume of the tetrahedron defined by the centers of the four alpha-sphere contact atoms. The set of all alpha-spaces for a set of points is equivalent to its Delaunay triangulation, which is the dual graph of the Voronoi diagram.

As described herein, the term "alpha-atom" refers to a theoretical atom having a radius of 1.8 angstroms, sharing its center with an alpha-sphere, and in approximate contact with the contact atoms of that alpha-sphere. An alpha-atom represents a localized interaction point within the pocket to which it belongs.

As described herein, the term "alpha-cluster" refers to a cluster of alpha-atoms representing a localized fragment-centric interaction region at the protein surface.

The systems and methods described herein can be used to map the interactions of any bound chemical fragment, for example from proteins, peptides, or small molecule inhibitors or chemical fragments that have been docked or designed into identified interaction regions. The methods described herein can also be used to map the surface of proteins not engaged in a PPI in order to develop, for instance, allosteric inhibitors. Furthermore, the systems and methods described herein are not limited to proteins but can also be used to map the topographies of DNA, RNA, lipid bilayers, or any other macromolecular structure.

FIG. 1 is a schematic flow diagram of a method 100 for mapping and evaluating protein surfaces, for example, for identifying a pocket of a protein which can bind a chemical fragment in a PPI. The operations of the method 100 may be stored on a computer readable medium which can be executed by a computing device (e.g. the computing device 430 described herein) to cause the computing device to perform operations of the method 100.

The method 100 includes performing a Voronoi tessellation of a surface of the protein at 102. A Voronoi diagram of the surface of the protein is developed at 104. The Voronoi diagram includes a plurality of Voronoi vertices. The Voronoi diagram is a tessellation of the space containing the points into a set of Voronoi cells, or polyhedrons, formed from planes that bisect adjacent points from the set.

All alpha-spheres on the surface of the protein are identified at 106 such that a center of the alpha-spheres corresponds to the Voronoi vertices. Expanding further, an alpha-sphere is a geometric feature derived from the Voronoi diagram of a set of points in 3-dimensional space. The alpha-sphere centers are defined at the vertices of this Voronoi tessellation. Each alpha-center will be an intersection of six bisecting planes and equidistant to exactly four points from the set.

In some embodiments, a "classical" Voronoi tessellation is employed, for which all atoms are treated as equivalent points. In such embodiments, the alpha-sphere makes contact with the centers of exactly four atoms, but is otherwise empty, and its radius is measured from alpha-sphere center to atom center. Alpha-spheres centered outside the protein surface indicate concave surface regions and represent volumes of potential interaction space.

The alpha-spheres are filtered based on radius at 108. The filtering includes removing alpha-spheres having a radius below a minimum radius and above a maximum radius. The filtering removes alpha-spheres that are likely too small to represent solvent accessible spaces. Further, in some embodiments the filter also removes alpha-spheres that are not likely near the surface of the protein, such as indicated by a large alpha-sphere radius. In some embodiments, the minimum radius is 3.2 angstroms and the maximum radius is 5.4 angstroms such that only solvent-accessible space near the surface of the protein are mapped.

The cut-off maximum radius is selected to balance a complete representation of the pocket structure and accurate application of a scoring and pocket occupation metric described herein. Furthermore, the cut-off minimum radius is selected to balance between a full representation of all solvent accessible spaces, and the confidence that unoccupied space will readily accommodate larger ligand atoms. In some embodiments, the cut-off minimum radius is 3.2 angstroms and cut-off maximum radius is 5.4 angstroms such that the alpha-sphere radius can have a size of about 3.3, 3.5, 3.7, 3.9, 4.1, 4.3, 4.5, 4.7, 4.9, 5.1 or about 5.3 angstroms, inclusive of all ranges and values therebetween.

Figure 6:
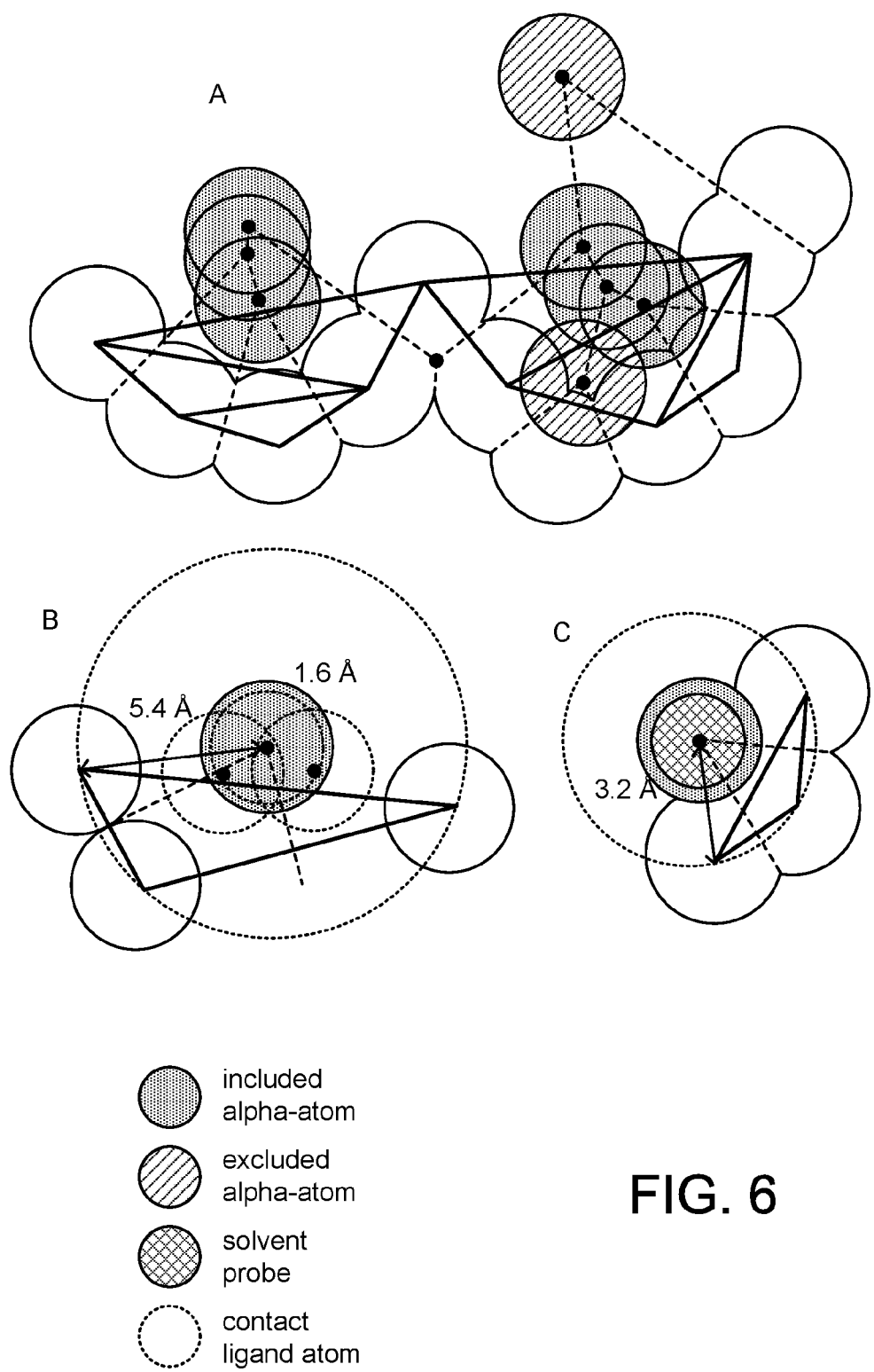
FIG. 6 panel (A) is a 2-dimensional schematic of two fragment-centric pockets in a protein surface, depicting the alpha-atom/alpha-space model; panel (B) is a schematic of an alpha-system that includes alpha-spheres, alpha-atoms, and alpha-spaces at maximum radius cutoff (5.4 angstroms); panel (C) is an alpha-system at minimum radius cutoff (3.2 angstroms).

Thus, only alpha-spheres having radii within a limited range are considered. If an alpha-sphere radius is too small, it will represent a position that is not solvent-accessible. FIG. 6 panel C depicts schematically that, in order to accommodate a typical solvent probe (1.4 angstroms radius), the space is represented by an alpha-sphere with a minimum radius of 3.2 angstroms. While a non-polar ligand atom (about 1.8 angstroms radius) at this alpha-center would experience some steric overlap with the surface in this minimum radius case, the tight but solvent-accessible spaces are included in the filtration and minimum alpha-sphere radius is held at 3.2 angstroms by default.

In contrast, if an alpha-sphere radius is too large, the use of its center as an atomic position conferring surface contact may become less accurate. Conversely, if the maximum radius cutoff drops too far, the representation of particularly broad pocket structure may be sacrificed from the surface map. A 5.4 angstrom maximum radius cutoff may be used to balance between alpha-sphere proximity to the surface and the complete representation of concave pocket structure (see FIG. 6 to visualize a geometric model for the relationship between an alpha-sphere with the maximum radius and the protein surface).

The remaining alpha-spheres are clustered into alpha-clusters at 110. The alpha-clusters include localized pockets on the protein surface clustered using a linkage algorithm with optimized clustering parameters such as, for example, an average linkage algorithm, a complete linkage algorithm, a density-based algorithm, or a density peak clustering algorithm. In some embodiments, an average linkage algorithm is used. The average linkage algorithm uses a pair wise alpha-sphere Euclidean distance matrix to generate a hierarchical dendrogram of the alpha-spheres according to an average-linking criterion. The average linkage algorithm utilizes a clustering parameter to separate the dendrogram of the alpha-spheres into a plurality of alpha-clusters. In some embodiments, the clustering parameter corresponds to a maximum average linkage distance between alpha-clusters. In particular embodiments, the clustering parameter is between 4.6 angstrom and 4.8 angstrom. In such embodiments, the average number of side chains from a bound peptide engaged by each pocket of the protein is 1. In particular embodiments, the clustering parameter can be reduced or increased slightly (e.g., by about ±10%) in order to affect the subdivision or merger of pockets near the threshold.

Figure 7:
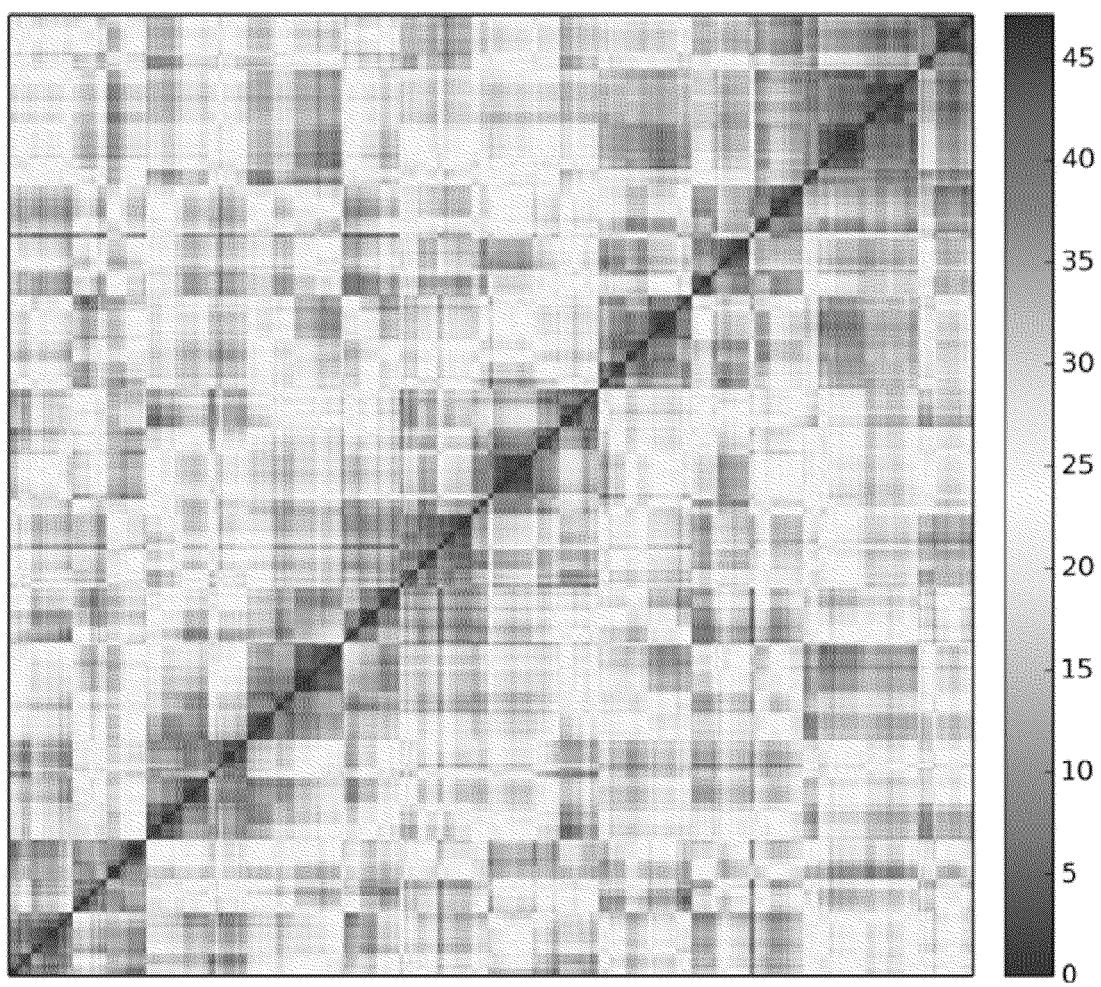
FIG. 7 is a dendrogram for an average-linkage hierarchical clustering of alpha-spheres at the surface of Mdm2 (PDB: 1ycr) based on Euclidian distance (angstroms).

Expanding further, for interaction space at PPI interfaces, because of the subtlety in fragment-centric modularity, there is often not a well-defined gap within the flow of alpha-spheres across the surface. The clustering operation 110, clusters filtered alpha-spheres into localized pockets, or alpha-clusters, using an average linkage routine. The average linkage routine uses the pairwise alpha-sphere Euclidian distance matrix to generate a dendrogram according to the average-linkage criterion. An exemplary dendrogram generated by operation 110 is shown in FIG. 7. The clustering parameter, which is the maximum mean distance between elements of any single cluster, determines where to cut the dendrogram and, to define the general size and final number of alpha-clusters in the topographical map. By considering amino acid side chains to be the natural binding fragments in PPIs, the clustering parameter is fit to yield, on average, one alpha-cluster for every side chain engaged in a PPI. As shown in FIG. 7, the average number of side chains per pocket is near unity when the maximum average linkage distance is within the range 4.6 to 4.8 angstroms. In some embodiments, the average linkage distance can be 4.7 angstroms.

At least one alpha-cluster for quantitative evaluation is selected at 112, which includes the pocket of the protein. The pockets of the protein are not screened by number of alpha-spheres, but instead all selected pockets are engaged in (or in the proximity of) a PPI/iPPI to provide a landscape-like interface map with complete coverage of all concave interaction space. The pocket of the protein is then displayed to a user at 114. For example, the method may display a 3 dimensional structure of the pocket or a chemical structure of the pocket to the user on a screen or a printed article.

Figure 2:
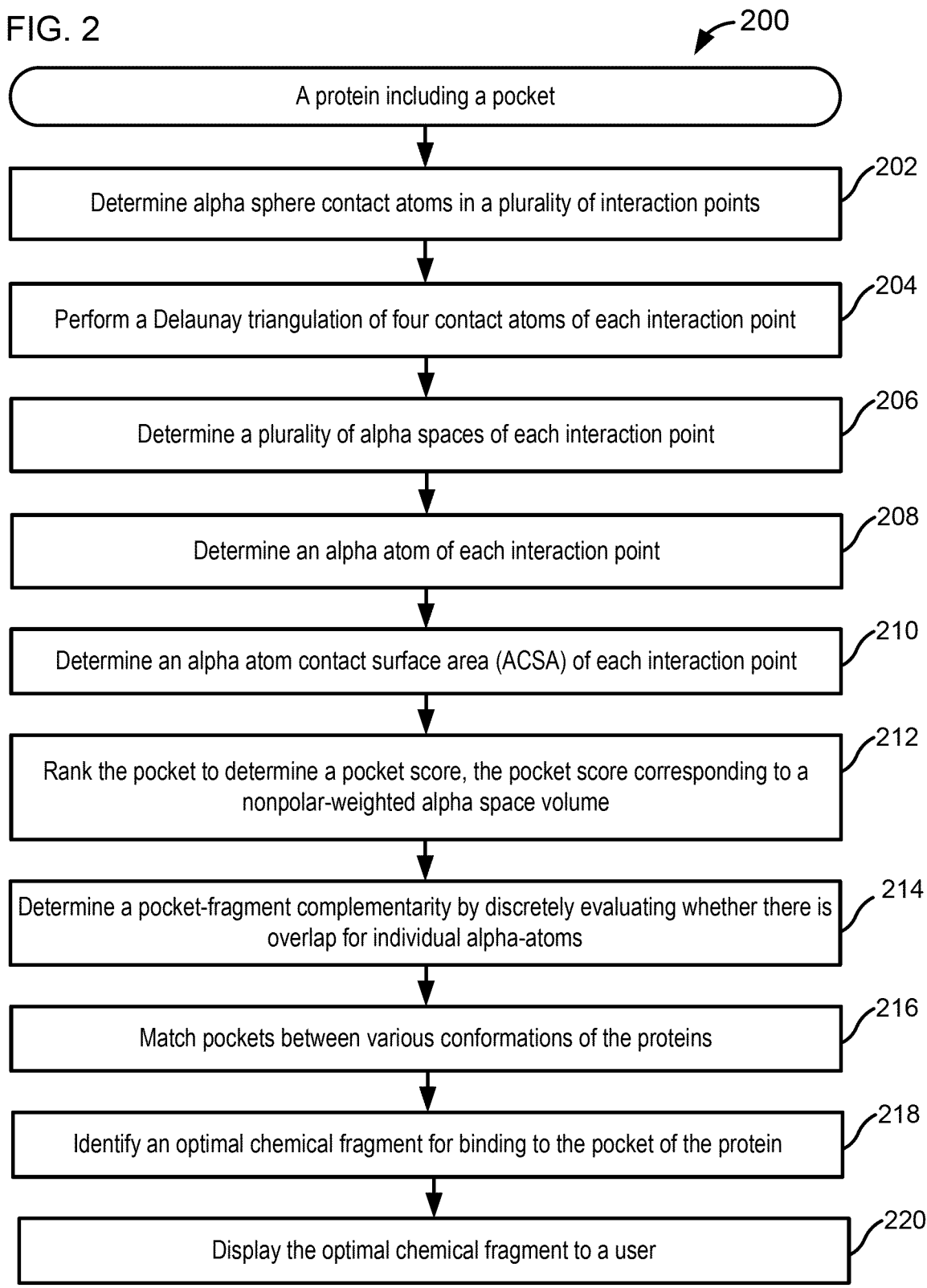
FIG. 2 is a schematic flow diagram of another embodiment of a method for evaluating a pocket of a protein for identifying a complimentary chemical fragment for binding to the pocket in a PPI.

FIG. 2 is a schematic flow diagram of a method 200 for evaluating a pocket of a protein, for example, for identifying a complimentary chemical fragment for binding to the pocket in a protein-protein-interaction. The methods 200 may be used to evaluate a pocket identified by the method 100. The operations of the method 200 can be stored on a computer readable medium which can be executed by a computing device (e.g. the computing device 430 described herein) to cause the computing device to perform operations of the method 200. The pocket evaluation provides a high-resolution map of underutilized and targetable pocket space at a PPI interface, and the analysis is facilitated by the alpha-sphere related features: alpha-atom and alpha-space, as described herein.

The methods 200 includes determining sets of alpha-sphere contact atoms in a plurality of interaction points at 202. The contact atoms include four atoms of the protein that are equidistant to a corresponding alpha-sphere which represents a single interaction point.

A Delaunay triangulation of the four contact atoms of each interaction point at 204. A plurality of alpha-spaces of each interaction point are determined at 206. Each alpha-space corresponds to a volume of a region defined by the Delaunay triangulation of the contact atoms of each interaction point. The alpha-space is the volume of the tetrahedron defined by the centers of the four alpha-sphere contact atoms. The set of all alpha-spaces for a set of points is equivalent to its Delaunay triangulation, which is the dual graph of the Voronoi diagram. In some embodiments, each of the plurality of alpha-spaces does not overlap with another of the plurality of alpha-spaces such that the plurality of alpha-spaces are positioned face-to-face within the pocket to define a contiguous volume without gaps. In particular embodiments, a sum of all the alpha-spaces correlates well with the surface area and curvature of the entire pocket.

Figure 4:
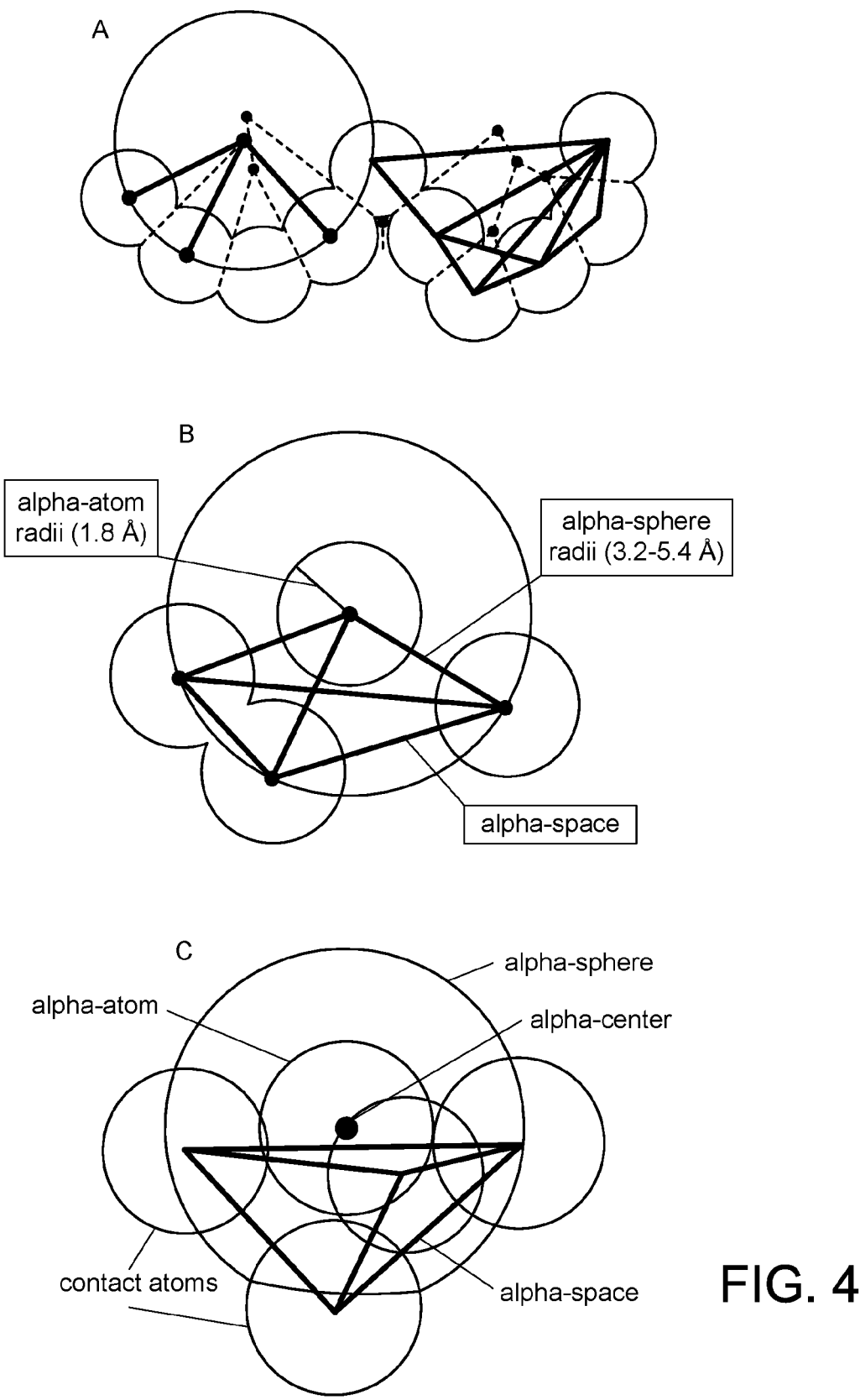
FIG. 4 panel (A) is a 2-dimensional schematic of two fragment-centric pockets in a protein surface.

The alpha-space is a geometric feature related to the size and shape of a localized region of protein surface. The size of an individual alpha-space reflects the surface area and curvature of the small surface region associated with the set four alpha-sphere contact atoms, as shown in FIG. 4. While the set of alpha-spheres in an alpha-cluster will overlap, the corresponding set of alpha-spaces will fit face-to-face to form a contiguous volume. This allows for the sum of overall alpha-spaces within a pocket to serve as a single metric that approximates the surface area and curvature of the complete pocket. It is to be noted that the alpha-space is not intended to represent the physical volume involved in the binding of the chemical fragments but simply serves as a metric that correlates with the properties of the protein surface at a specific interaction point.

An alpha-atom of each interaction point is determined at 208. The alpha-atom includes a theoretical atom having a radius of 1.8 angstrom in approximate contact with a surface defined by the contact atoms of the pocket. This represents the radius of a theoretical non-polar ligand atom.

Figure 8:
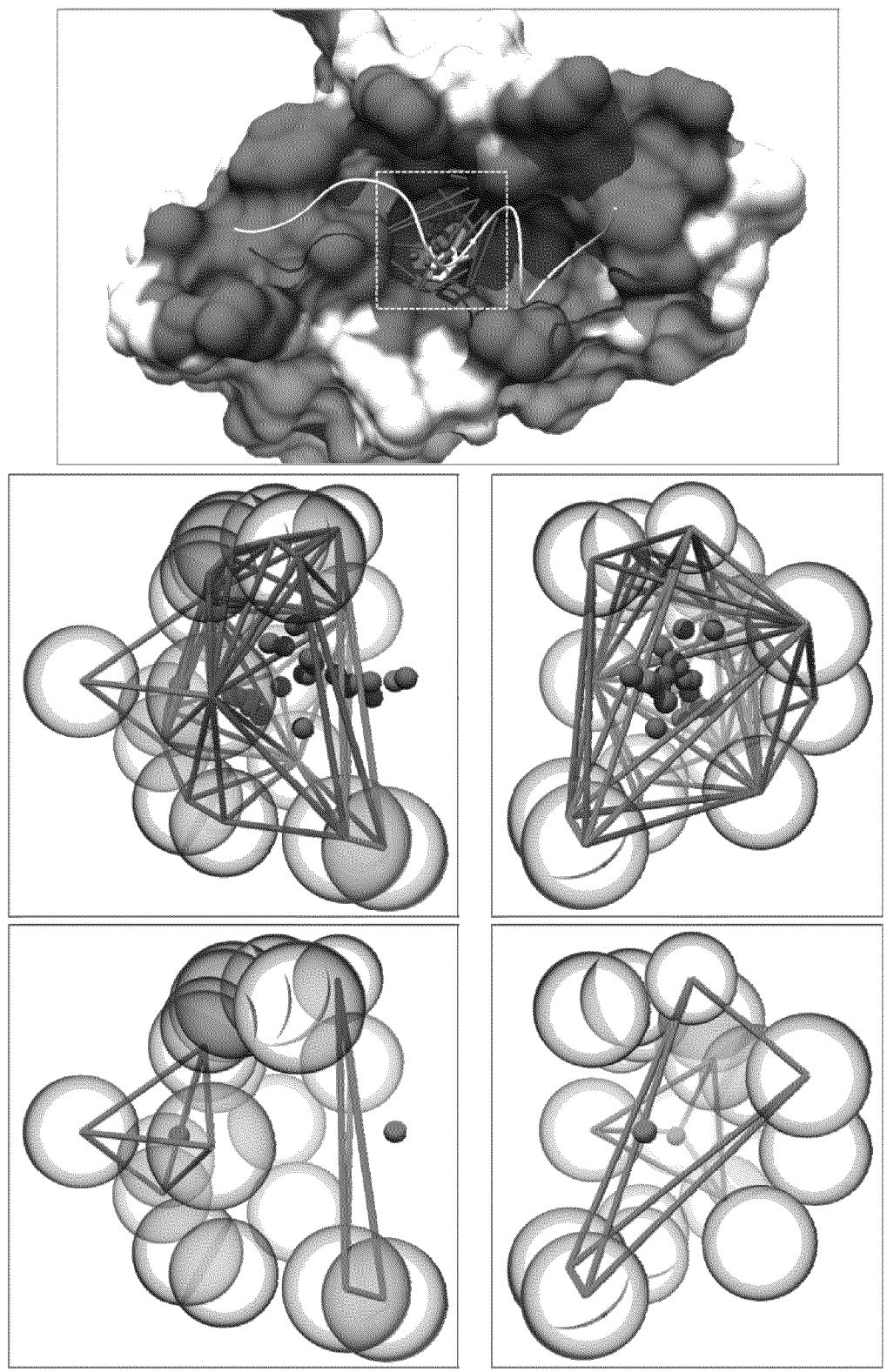
FIG. 8 are illustrations of pocket-lining atoms, alpha-sphere centers, and alpha-spaces for the Mdm2/p53 Trp92 pocket; (Top) shown in the context of the protein surface (PDB: 1ycr). (Middle) The entire alpha-cluster is shown with two selected alpha-spheres and their respective pocket-atoms and alpha-spaces. Top left is a side-view, and top right is a perspective view of the pocket. (Bottom) Displaying only the alpha-spheres and alpha-spaces for a clearer visualization of the alpha-sphere/alpha-space relationship.

Every alpha-atom has an associated alpha-space, the volume of which captures information about the relative positions of the four contact atoms, which is related to the structure of the surface region associated with these four atoms. FIG. 8 illustrates the geometric relationship between the alpha-atom and the alpha-space in the context of an alpha-cluster (the Trp92 pocket from Mdm2/p53). In some embodiments, the alpha-atoms of each localized region of the pocket form an overlapping alpha-cluster. An outline of the alpha-cluster represents a shape and size of a chemical fragment complimentary to the pocket. In other words, the outline of a set of overlapping alpha-atoms defines the approximate shape of a ligand fragment with structural complementarity to that local interaction space. The enclosed volume of this alpha-cluster pseudo-fragment will represent the approximate volume of an expected chemical fragment binder.

Figure 5:
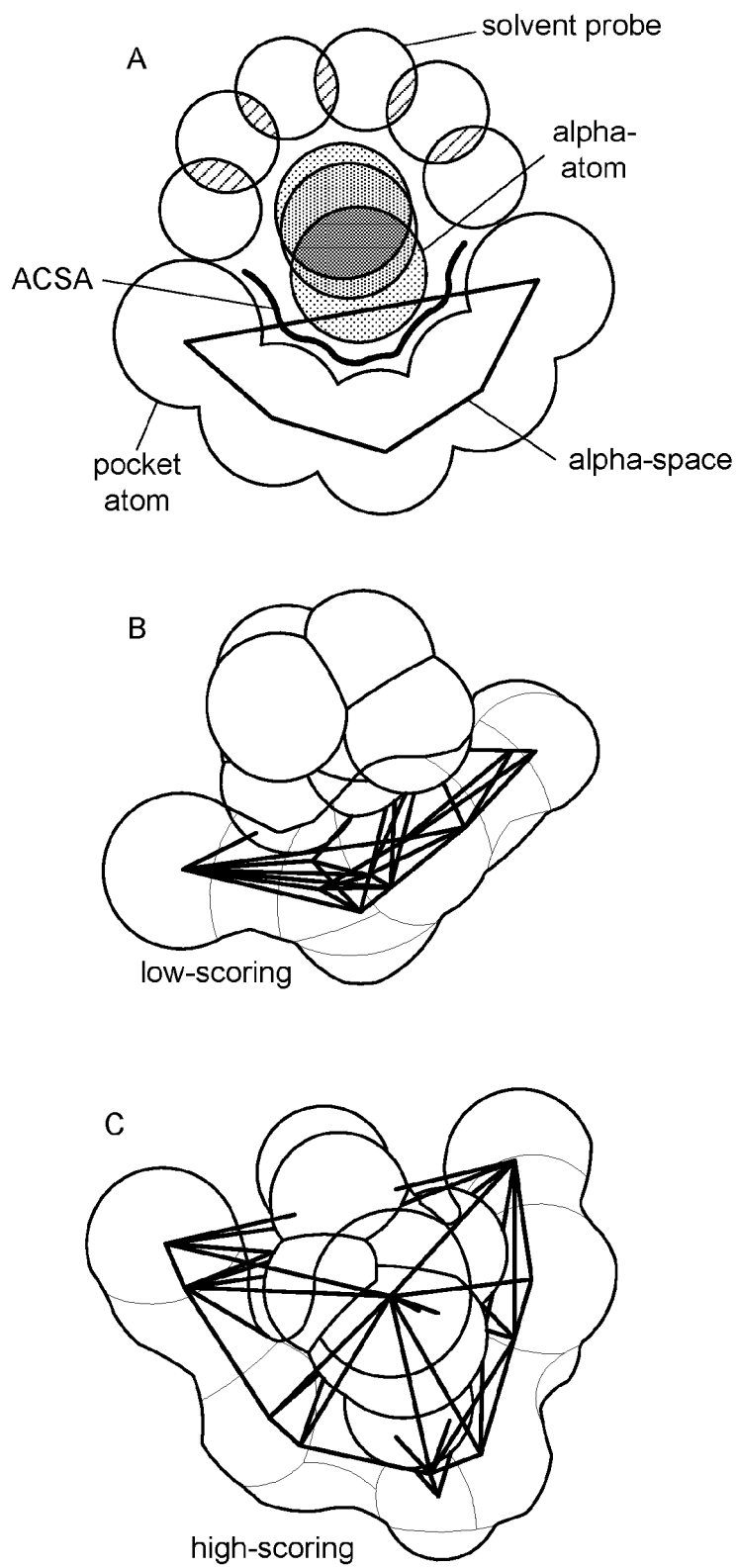
FIG. 5 panel (A) is a 2-dimensional schematic depicting components used to calculate pocket score: solvent probes and alpha-atoms are used to calculate the alpha-atom contact surface area (ACSA) of the pocket atoms; panel (B) is an alpha-atom and alpha-space representation for a low-scoring, shallow pocket; and panel (C) is an alpha-atom and alpha-space representations for a high-scoring, deep pocket.

An alpha-atom contact surface area (ACSA) of each interaction point is determined at 210. When alpha-spheres are clustered to define a pocket, the corresponding alpha-atoms form an overlapping alpha-cluster, the outline of which represents the approximate shape and size of that pocket's complementary pseudo-fragment, as shown in FIG. 5. In some embodiments, determining the ACSA includes taking a difference between a first contact surface of the contact atoms of each localized region of the pocket, and a second contact surface of the contact atoms using the alpha-cluster as a bound pseudo-fragment. In this manner, ACSA provides a novel way to calculate the exact pocket-centric surface area and/or the pocket-centric desolvated area.

The pocket is ranked to determine a pocket score (also referred to herein as "interaction score") at 212. The pocket score corresponds to a nonpolar-weighted alpha-space volume and reflects a maximal affinity model, where the score is proportional to the affinity expected to be achieved between each pocket and a hypothetical complementary chemical fragment. In some embodiments, the pocket score is determined using a formula (I):

$$score_J = \sum_{\alpha \in J} \left( V_\alpha * \frac{\sum_{i \in \alpha}(ACSA_{i,J} * NP_{i,J})}{\sum_{i \in \alpha} ACSA_{i,J}} \right) \quad (I)$$

where $\alpha$ is an alpha-space within the pocket J with volume $V_\alpha$, $ACSA_{i,J}$ is the alpha-atom contact surface area for atom i calculated using alpha-cluster J and $NP_{i,J}$ is the binary polarity status for atom i in pocket J.

In other embodiments, the pocket score is determined using the total alpha-space using the following formula:

$$score_J = \Sigma_{\alpha \in J}(V_\alpha),$$

or using the nonpolar weighting alone using the following formula:

$$score_J = \frac{\sum_{\alpha \in J}\left( V_\alpha * \frac{\sum_{i \in \alpha}(ACSA_{i,J} * NP_{i,J})}{\sum_{i \in \alpha} ACSA_{i,J}} \right)}{\sum_{\alpha \in J}(V_\alpha)}.$$

A pocket-fragment complementarity is determined at 214 by discretely evaluating whether there is overlap for individual alpha-atoms. In some embodiments, the pocket-fragment complementarity is determined using a formula (II):

$$\% occ_J = \frac{\sum_{\alpha \in J}(V_\alpha * O_\alpha)}{\sum_{\alpha \in J} V_\alpha} \quad (II)$$

where:
$\% occ_J$ is the percentage of the interaction space of pocket J that is occupied by the bound ligand, $\alpha$ is an alpha-space within pocket J with volume $V_\alpha$, and $O\alpha$ is the binary occupation status of $\alpha$.

Expanding further, the total alpha-space of the pocket is partitioned into occupied space and unoccupied space by leveraging the discreet nature of each alpha-atom/alpha-space pair. Thus, the alpha-space occupation status is mediated through the position of its corresponding alpha-atom. Alpha-space occupation is conferred by spatial overlap between the alpha-atom and an atom from the bound ligand molecule, evaluated using a 1.6 angstrom cutoff distance measured between the centers of the alpha-atom and the ligand atoms. This cutoff is designed to be just longer than an average carbon-carbon bond length so that an unoccupied alpha-atom should represent a targetable interaction space, able to accommodate at least a methyl extension to the ligand, given the proper structure and chemistry of the evolving ligand. In some embodiments, an alpha-space is at least partially occupied when a distance between a center of the alpha-space and a center of the overlapping chemical fragment atom is less than 1.6 angstroms. In other embodiments, the alpha-space is unoccupied when the distance between the center of the alpha-space and the center of the overlapping chemical fragment atom is greater than 1.6 angstroms.

As the concave space represented by an alpha-sphere gets flatter, its alpha-sphere radius gets larger. This results in large pocket volumes assigned to shallow pockets, for which much of the alpha-sphere volume lies outside the meaningful interaction space. A more meaningful alpha-cluster volume can be calculated using the alpha-atoms, with 1.8 angstroms radii to represent generic nonpolar ligand atoms. This alpha-cluster volume can be used to approximate the molecular volume of a pocket's complementary ligand fragment.

In particular embodiments, a score of the "occupied" portion of the pocket can also be used as a type of interaction score. For example, the total interaction score of a ligand or binder can be evaluated using: (1) total pocket score for all contact pockets; or (2) total occupied pocket score by summing over all the alpha-spaces associated with occupied alpha atoms. Alternatively, the interaction score can also be calculated on a residue-by-residue basis (e.g., when mapping the binding interface of a peptide) by: (1) total pocket score of any pocket in contact with the residue; or (2) total occupied pocket score for all alpha-spaces associated with "occupied" alpha-atoms. In one embodiment, the interaction score can be used as a virtual alanine scanning approach in which each residue is modified to alanine, and the difference in the interaction score for each residue is calculated. Inversely, the total unoccupied pocket score for a pocket can be calculated by summing over the "unoccupied" alpha-spaces of that pocket. This can be used to identify the pockets with the greatest opportunity for fragment optimization.

In one embodiment, a pocket score is determined using only the alpha-spaces associated with the alpha-atoms that are occupied by a chemical fragment. In some embodiments, at least a portion of a chemical fragment is extended to overlap the alpha-atom associated with an unoccupied alpha-space to optimize pocket occupation.

Pockets between various conformations of the proteins are matched at 216. In some embodiments, the pocket similarity is determined using a formula (III):

$$sim_{J,k} = \frac{\sum_{i\in (J\cap K)} ACSA_{i,J} + ACSA_{i,K}}{\sum_{i\in J} ACSA_{i,J} + \sum_{i\in K} ACSA_{i,K}} \quad (III)$$

where:
$sim_{J,K}$ is a similarity metric between a first conformation J of the pocket and a second conformation K of the pocket. In particular embodiments, a similarity cut-off for matching the first conformation J of the pocket and the second conformation K of the pocket is 30%.

In one embodiment, when comparing pockets between two conformations of the same protein, all pairwise pocket similarities are first calculated, and pockets are paired off into exclusive pairs in the order of highest similarity. By matching pockets with adequate overlap between their atomistic ACSAs, the pocket is treated as a dynamic object with an intrinsic degree of structural integrity. The pocket matching allows quantification of the degree of structural flexibility between two conformations of a dynamic pocket.

In particular embodiments, the pocket matching can be extended to apply to a series of protein conformations altogether (e.g., a molecular dynamics trajectory of the protein) to mutually match pockets among all conformations and to yield a dynamic pocket object that includes multiple instances of the "same" pocket. This can also be performed using a clustering algorithm (e.g., the average linkage algorithm). In another embodiment, the chemical fragments can be positioned or extended into the pockets to optimize pocket occupation. In another embodiment, the method 200 can be used to map a complete protein or other macromolecular structure surface to provide a complete interaction map of all concave interaction space across the entire surface.

Based on the pocket matching, an optimal chemical fragment for binding to the pocket of the protein is identified at 218. The optimal chemical fragment is displayed to a user at 220. In some embodiments, the methods 100 and 200 can be used for inhibitor, agonist and/or antagonist design and optimization. For example, once an interaction pocket is identified and evaluated for the occupation of that pocket based on the overlap between its alpha-atoms and interacting fragment atoms, the bound fragment can be optimized by chemically extending the fragment into unoccupied space to introduce new overlap with the unoccupied alpha-atoms of the pocket. This can increase the overall occupation of the pocket. The designed inhibitor may then be recombinantly synthesized or synthesized using any other method, for example for use as a therapeutic.

In one embodiment, the inhibitor can be designed by theoretically mutating a residue engaged in a PPI to a different canonical or non-canonical amino acid and evaluating whether the pocket occupation has increased. In another embodiment, a potential ligand fragment or inhibitor scaffold is specifically positioned to maximize overlap with the alpha-atoms from a pocket or set of pockets in order to evaluate the extent of a potential fragment to form favorable interactions with that pocket or set of pockets. This can, for example, be used to predict a favored binding position for the interacting ligand or peptide.

Figure 3:
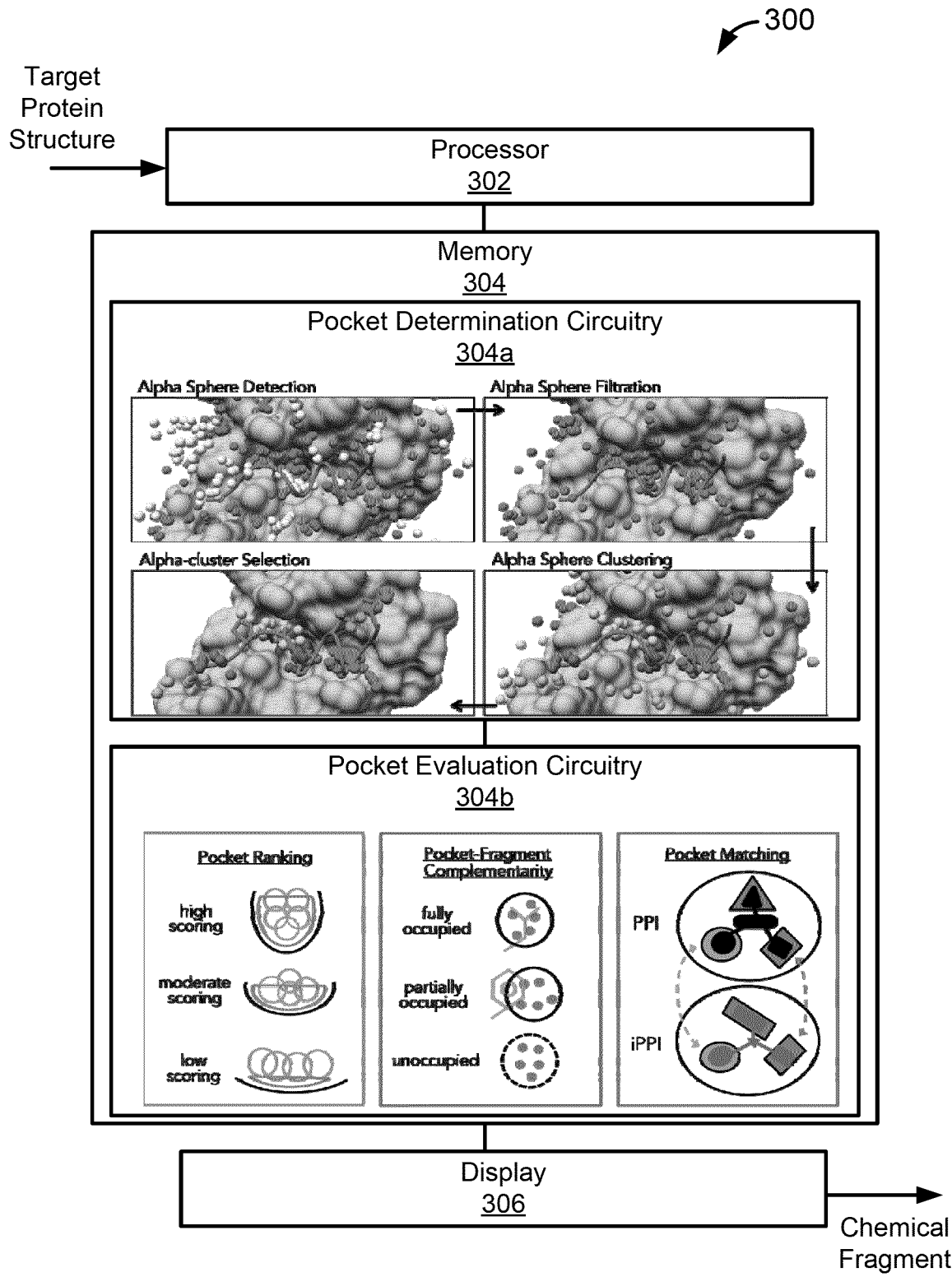
FIG. 3 is an overview of an embodiment of a system for identifying a protein pocket and evaluating the pocket.

FIG. 3 is a diagram of a system 300 for identifying and evaluating a pocket of a protein to identify chemical fragments which can optimally bind to the pocket in a PPI. The system 300 includes a processor 302, a memory 304 or any other computer readable medium and a display 306.

The processor 302 can include a microprocessor, programmable logic controller (PLC) chip, an ASIC chip, or any other suitable processor. The processor 302 is in communication with the memory 304 and configured to execute instructions, algorithms, commands or otherwise programs stored in the memory 304.

The memory 304 includes any of the memory and/or storage components discussed herein. For example, memory 304 may include RAM and/or cache of processor 304. The memory 304 may also include one or more storage devices (e.g., hard drives, flash drives, computer readable media, etc.) either local or remote to controller 304. The memory 304 is configured to store look up tables, algorithms or instructions.

For example, the memory 304 includes a pocket identification circuitry 304a, and a pocket evaluation circuitry 304. In some embodiments, the system 300 can include a computing device (e.g., the computing device 430) which includes the pocket identification circuitry 304a and the pocket evaluation circuitry 304b. The computing device can be specifically programmed to execute the instructions of the pocket identification circuitry 304a and the pocket evaluation circuitry 304b so that an optimal chemical fragment for binding to the protein pocket can be identified. The display 306 is configured to display the optimal chemical fragment of the user. The display 306 may include any suitable display, for example a computer monitor, a printed article and/or any other display.

In a first stage, the pocket identification circuitry 304a is performs the following steps:

(1) Alpha-sphere Detection: All alpha-spheres are identified from the Voronoi tessellation of a protein structure. A Voronoi tessellation of a surface of the protein is performed. A Voronoi diagram of the surface of the protein is developed, which includes a plurality of Voronoi vertices. All alpha-spheres on the surface of the protein are identified such that a center of the alpha-spheres corresponds to the Voronoi vertices. The alpha-sphere detection step can be substantially similar to operations 102-106 described with respect to the method 100 and therefore, not described in further detail herein.

(2) Alpha-sphere Filtration: The alpha-spheres are filtered based on radius by removing alpha-spheres having a radius below a minimum radius and above a maximum radius. In some embodiments, the minimum radius is set at 3.2 angstroms, as shown in FIG. 6C, and the maximum radius is 5.4 angstroms, as shown in FIG. 6B. These filtration parameters are optimized to restrict mapping to include only solvent-accessible space near the surface of the protein. The alpha-sphere filtration can be substantially similar to the operation 108 described with respect to method 100.

(3) Alpha-sphere Clustering: Remaining alpha-spheres are clustered into pockets, or alpha-clusters, using a linkage algorithm, for example, an average linkage algorithm to restrict individual pocket size to represent small, fragment-centric interaction spaces. For interaction space at PPI interfaces, because of the subtlety in fragment-centric modularity, there is often not a well-defined gap within the flow of alpha-spheres across the surface. The alpha-sphere clustering clusters filtered alpha-spheres into localized pockets, or alpha-clusters, using the average linkage routine (e.g., the average linking routing included in the SciPy hierarchical clustering package). The routine uses the pairwise alpha-sphere Euclidian distance matrix to generate a dendrogram according to the average-linkage criterion. An exemplary dendrogram is shown in FIG. 7. The clustering parameter, which is the maximum mean distance between elements of any single cluster, determines where to cut the dendrogram and, thus, determine the general size and final number of alpha-clusters in the topographical map.

By considering amino acid side chains to be the natural binding fragments in PPIs, the clustering parameter is fit to yield, on average, one alpha-cluster for every side chain engaged in a PPI. As shown in FIG. 7, the average number of side chains per pocket is near unity when the maximum average linkage distance is within a range of 4.6 to 4.8 angstroms. The number of side chains per pocket is calculated by dividing the number of side chains in contact with a pocket by the number of pockets in contact with a side chain (omitting pockets exclusively occupied by backbone atoms). In some embodiments, the average linking distance is 4.7 angstroms. In particular embodiments, the alpha-sphere clustering can be substantially similar to the operation 110 described with respect to method 100.

(4) Alpha-cluster Selection: At least one alpha-cluster, which includes a pocket of the protein is selected for evaluation. In some embodiments, pockets are not screened by number of alpha-spheres, but all pockets engaged in (or in the proximity of) a PPI/iPPI are selected to provide a landscape-like interface map with complete coverage of all concave interaction space.

After all pockets across a protein surface have been identified by the pocket determination circuitry 304a, the pocket evaluation circuitry focuses the pocket analysis onto the PPI/iPPI interface. This focus can be restricted to include only pockets in direct contact with the peptide or inhibitor binding partner, or it can be broadened to also include unoccupied pockets in the local vicinity of the interface. In one implementation, an interface pocket is detected if there is direct contact between at least one alpha-sphere and an atom from the peptide or inhibitor binder, using a 1.6 angstrom contact distance cutoff. Then the adjacent unoccupied pockets can be identified by searching for overlap between the atom list of an unoccupied pocket and the atom list of a direct contact pocket. In another implementation, an interface atom list is used and is defined to include any atom with solvent-accessible surface area (SASA) reduced upon placement of the peptide or inhibitor binder at the interface. In such implementations, a minimum fraction of a pocket's atoms is found in the interface atom list in order to qualify as an interface pocket. The value of this minimum fraction controls the scale of the interface expansion. In some embodiments, the minimum fraction can be in the range of 30% to 50% (e.g., 30%, 35%, 40%, 45% or 50% inclusive of all ranges and values therebetween). In particular embodiments, the minimum fraction can be 50%.

Figure 13:
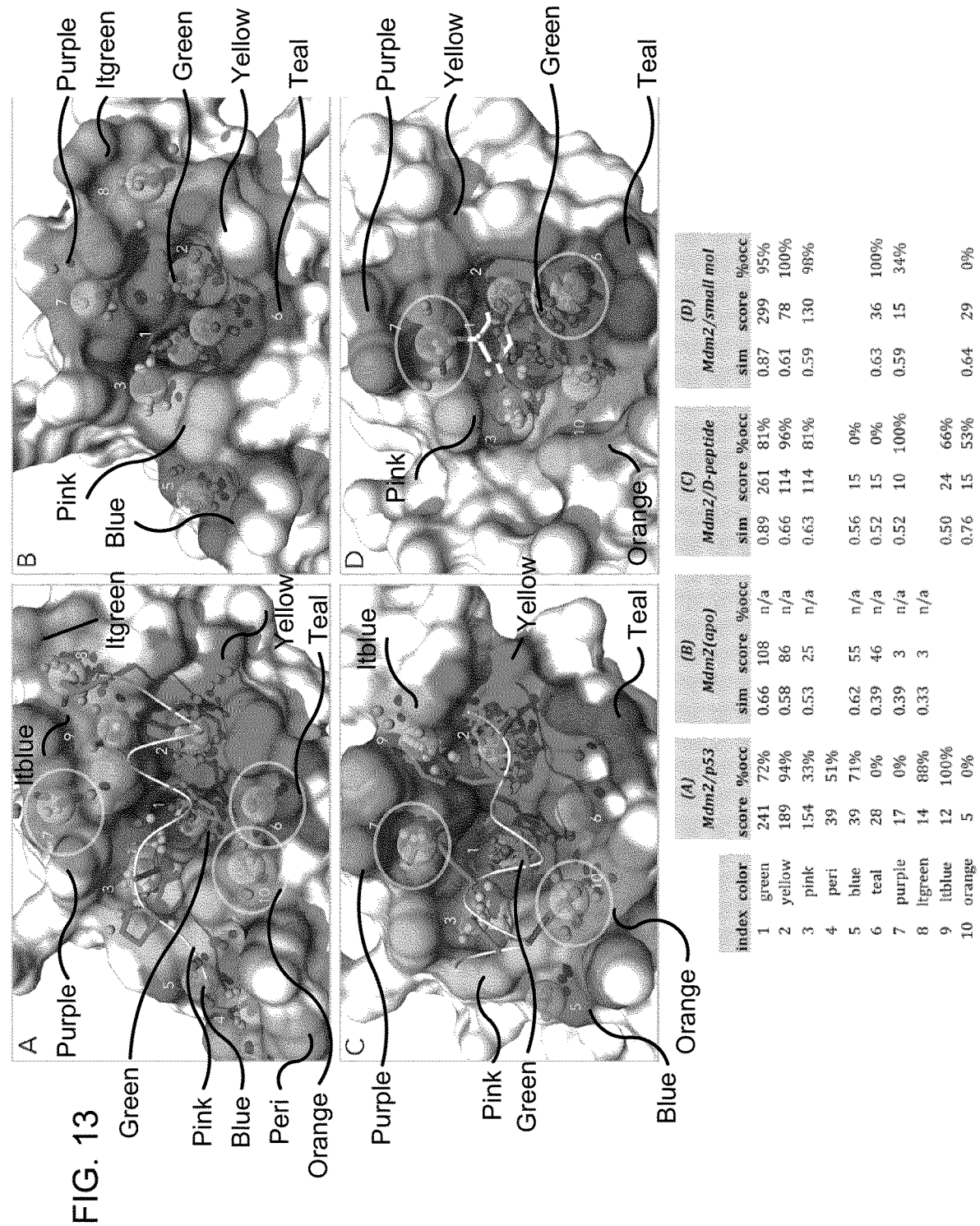
FIG. 13 panel A is an illustration of Mdm2/p53 (PDB: 1ycr), panel B of Mdm2 apo (PDB: 1z1m), panel C of Mdm2/$^D$PMI-δ ($_D$-peptide inhibitor) (PDB: 3tpx), panel D Mdm2/piperidinone sulfone derivative (small molecule inhibitor) (PDB: 4oas). Circled in panel A are three unoccupied pockets near the PPI interface, and, in panels C and D, matching pockets are targeted by inhibitor fragments. The table (bottom) presents the quantitative matching results for all pockets, including similarity (if matched to a native Mdm2/p53 pocket), pocket score, and percent pocket occupation.

For example, the three unoccupied pocket at the Mdm2/p53 interface, depicted in FIG. 13 panel A, are detected when the minimum fraction of interface atoms is set to 50%. The interface atom list from a PPI can also be applied to the mapping of an apo protein in order to focus the FCTM to the similar surface region.

Once the pocket is identified using the pocket identification circuitry 304a, the identified pocket is then evaluated by the pocket evaluation circuitry 304b in a second stage. Selected pockets from the first stage are quantitatively characterized in the second stage. The pocket evaluation circuitry 304b includes three consecutive steps including pocket ranking, pocket-fragment complementarity and pocket matching, as shown in FIG. 3. The pocket evaluation provides a high-resolution map of underutilized and targetable pocket space at a PPI interface, and the analysis is facilitated by the alpha-sphere related features, alpha-atom and alpha-space, described with respect to the method 200.

The pocket evaluation circuitry 304b first determines the alpha-sphere contact atoms in a plurality of interaction points. The contact atoms include four atoms of the protein that are equidistant to a corresponding alpha-sphere which represents a single interaction point (as described before herein). A Delaunay triangulation of the four contact atoms of each interaction point is performed. A plurality of alpha-spaces of each interaction point, each alpha-space corresponding to a volume of a region defined by the Delaunay triangulation of the contact atoms of each interaction point. An alpha-atom of each interaction point is determined. Furthermore, an alpha-atom contact surface area (ACSA) of the pocket is also determined.

Alpha-space is used as a geometric feature related to the size and shape of a localized region of protein surface. The size of an individual alpha-space reflects the surface area and curvature of the small surface region associated with the set four alpha-sphere contact atoms, as shown in FIG. 4. While the set of alpha-spheres in an alpha-cluster overlap, the corresponding set of alpha-spaces fit face-to-face to form a contiguous volume. This allows for the sum over all alpha-spaces within a pocket to serve as a single metric that approximates the surface area and curvature of the complete pocket. FIG. 8 illustrates the geometric relationship between the alpha-atom and the alpha-space in the context of an alpha-cluster (shown for Trp92 pocket from Mdm2/p53).

The alpha-atom construct can be used to calculate the alpha-atom contact surface area (ACSA) of the pocket. When alpha-spheres are clustered to define a pocket, the corresponding alpha-atoms form an overlapping alpha-cluster, the outline of which represents the approximate shape and size of that pocket's complementary pseudo-fragment, as shown in FIG. 5. Taking the difference between the contact surface area of a protein alone, and that of the protein in complex with a single alpha-cluster yields the exact pocket surface area that is desolvated by the theoretical pseudo-fragment.

The pocket evaluation circuitry 304b ranks the pocket to determine a pocket score which corresponds to a nonpolar-weighted alpha-space volume which can participate in the protein-protein-interaction. Given a pocket J, the pocket evaluation circuitry 304b may calculate a pocket score using the formula I:

$$score_J = \sum\nolimits_{\kappa \in J} \left( V_\alpha * \frac{\sum_{i \in \alpha}(ACSA_{i,J} * NP_{i,J})}{\sum_{i \in \alpha} ACSA_{i,J}} \right) \quad \text{(I)}$$

where α is an alpha-space within pocket J with volume $V_\alpha$, $ACSA_{i,J}$ is the alpha-atom contact surface area for atom i calculated using alpha-cluster J and $NP_{i,J}$ is the binary polarity status for atom i in pocket J (1 for non-polar atoms and 0 for polar atoms).

In other embodiments, the pocket score is determined using the total alpha-space using the following formula:

$$score_J = \sum_{\alpha \in J}(V_\alpha)$$

or using the nonpolar weighting alone using the following formula:

$$score_J = \frac{\sum_{\alpha \in J}\left(V_\alpha * \frac{\sum_{i \in \alpha}(ACSA_{i,J} * NP_{i,J})}{\sum_{i \in \alpha} ACSA_{i,J}}\right)}{\sum_{\alpha \in J}(V_\alpha)}$$

A pocket-fragment complementarity is determined by discretely evaluating whether there is overlap for individual alpha-atoms. For example, if pocket J is engaged in a PPI or iPPI, the structural complementarity between the pocket and the bound chemical fragment is assessed using the formula II:

$$\% occ_J = \frac{\sum_{\alpha \in J}(V_\alpha * O_\alpha)}{\sum_{\alpha \in J} V_\alpha} \quad (II)$$

where % $occ_J$ is the percentage of the interaction space of pocket J that is occupied by the bound ligand, α is an alpha-space within pocket J with volume $V_\alpha$, and O is the binary occupation status of α (1 if occupied and 0 if unoccupied). The total alpha-space of the pocket is partitioned into occupied space and unoccupied space by leveraging the discreet nature of each alpha-atom/alpha-space pair. Thus, the alpha-space occupation status is mediated through the position of its corresponding alpha-atom. Alpha-space occupation is conferred by spatial overlap between the alpha-atom and an atom from the bound ligand molecule, evaluated using a 1.6 angstroms cutoff distance measured between the centers of the alpha-atom and the ligand atoms. This cutoff is designed to be just longer than an average carbon-carbon bond length so that an unoccupied alpha-atom should represent a targetable interaction space, able to accommodate at least a methyl extension to the ligand, given the proper structure and chemistry of the evolving ligand. In some embodiments, at least a portion of a chemical fragment is extended to overlap the alpha-atom associated with an unoccupied alpha-space to optimize pocket occupation.

The pocket evaluation circuitry 304b matches pockets between various conformations of the protein. To match similar pockets between different conformations (or complexes) of the same protein, the following pocket similarity metric according to the formula (III) is used:

$$sim_{J,k} = \frac{\sum_{i \in (J \cap K)} ACSA_{i,J} + ACSA_{i,K}}{\sum_{i \in J} ACSA_{i,J} + \sum_{i \in K} ACSA_{i,K}} \quad (III)$$

where, in the numerator, the ACSAs of the atoms shared by pocket J and pocket K are summed, and divided by the total ACSA of pocket J and pocket K. The formula (III) approximates the portion of the total pocket surface area that is similar between the two pockets. When comparing pockets between two conformations of the same protein, all pairwise pocket similarities are calculated first, and pockets are paired off into exclusive pairs in the order of highest similarity. A minimum similarity cutoff can be modulated to control the strictness applied in pocket matching. In some embodiments, the similarity cutoff is 30%. By matching pockets with adequate overlap between their atomistic ACSAs, the pocket is treated as a dynamic object with an intrinsic degree of structural integrity. Thus, pocket matching allows quantification of the degree of structural flexibility between two conformations of a dynamic pocket.

Examples of FCTM of Specific Proteins

In this section, p53 tumor suppressor peptide, which targets Mdm2 (Mdm2/p53 PPI), is used as a test case to demonstrate the applicability of the system 300 for performing FCTM described herein. To provide a high-resolution visual and quantitative characterization of all interaction space at a targetable PPI interface, results were compared with those obtained from a docking-based program, FTMap®. Finally, the application of systems and methods described herein were evaluated for a larger dataset of 12 PPIs and 12 iPPIs from the 2P2I database of PPIs. With the use of the pocket score and pocket matching, it is confirmed that high-ranking fragment-centric pockets are generally enriched at the interaction interfaces and are often conserved between PPIs and their corresponding iPPIs. Additionally, a shift toward higher pocket-fragment complementarity in the high-ranking iPPI pockets was observed over the high-ranking PPI pockets, which may contribute to the generally high ligand efficiency (LE) documented for successful iPPIs.

FCTM of the Mdm2/p53 Interface

Mdm2/p53 is an important PPI and oncogene drug target, with several small molecule inhibitors currently in clinical trials. Its PPI interface is formed between a 13-residue helical section from the N-terminal transactivation domain of p53 and a well-defined binding groove in the surface of Mdm2. This interaction is known to be anchored by three primary hot spot residues from p53—Phe19, Trp23, Leu26 and a secondary hydrophobic interaction with Leu22.

Figure 9:
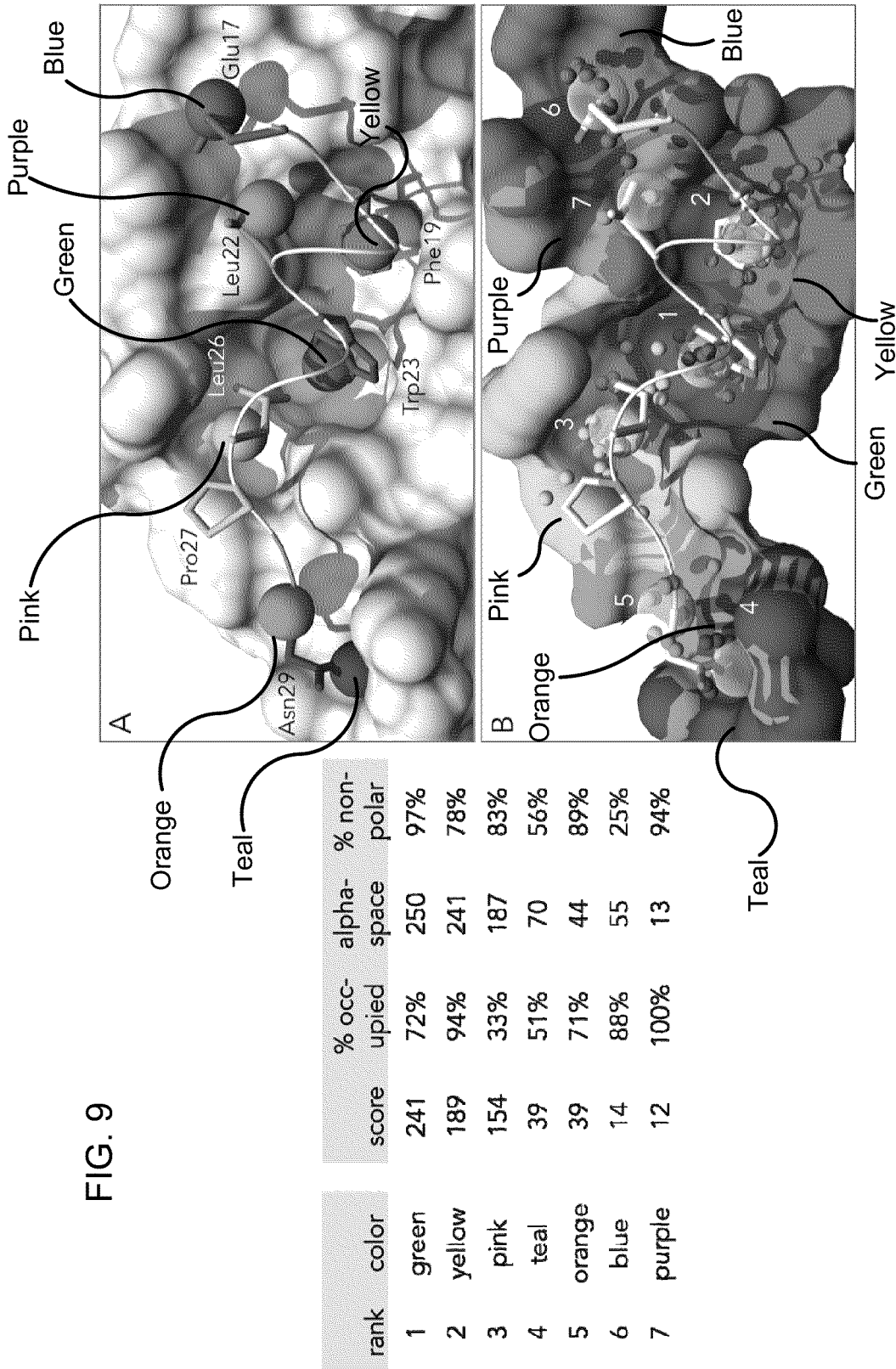
FIG. 9 is an illustration (right) of alpha-space-based pocket features presented for the 7 contact pockets at the Mdm2/p53 PPI interface, and a table (left) of pocket ranks. Panels (A) and (B) are different visual representations of the FCTM result for Mdm2/p53. Panel (A) shows interface pockets represented by the centroid of each alpha-cluster. The side chains from p53 are displayed and labeled whenever they make contact with one of the interface pockets. The natural modularity of the surface is exhibited in the overlap between the centroids and the side chains. In panel (B) each pocket is represented as a surface, alpha-sphere centers are shown as small spheres surrounded by pocket, and the alpha-cluster centroids are depicted as large transparent spheres. Pockets are numbered by rank, as in the table (left).

As shown in FIG. 9, FCTM performed using the system 300 detects a total of seven pockets in the surface of Mdm2 at the Mdm2/p53 interface. Aside from pocket 3, which is occupied by the side-chains of Leu26 and Pro27, and pocket 5, which interacts with the backbone of p53, the other five pockets each contact a single, distinct side chain from p53, including Phe19, Leu22, and Trp23. There is a clear spatial overlap between the alpha-cluster centroids and the pocket-bound peptide fragments. This indicates an innate structural modularity in the protein surface that reflects the corresponding side chain interactions.

For the seven pockets, the calculated pocket features (including pocket score, percent pocket occupation, total alpha-space, and percent non-polar) are presented in FIG. 9. The pockets are ranked and numbered by pocket score. As seen in FIG. 9, pocket 1 (Trp23; score=241; 72% occupied) and pocket 2 (Phe19; score=189; 94% occupied) engage the two essential hot spot residues Trp23 and Phe19 of p53, respectively. The less occupied Pocket 3 (score=154; 33% occupied) engages the third but less dominant hot spot residue Leu26. These results are very consistent with the experimental alanine-scanning data for p53, as shown in Table I, in which mutation of either Phe19 or Trp23 reduces the Mdm2/p53 binding affinity below the detectable limit and Leu26/Ala mutagenesis results in a significant reduction of binding affinity by more than 50 fold.

TABLE I

Experimental alanine scanning results for Mdm2/p53, calculated from $K_d$ values. $\Delta\Delta G$ >3.0 kcal/mol (red), 2.0 < $\Delta\Delta G$ < 3.0 kcal/mol (blue).

| ala mut | Mdm2/p53 | |
|---|---|---|
| | $K_d$ (μM) | $\Delta\Delta G$ (kcal/mol) |
| WT | 0.44 | 0 |
| Glu17 | 0.56 | 0.1 |
| Thr18 | 1.2 | 0.6 |
| Phe19 | n.d. | n.d. |
| Ser 20 | 0.21 | −0.4 |
| Asp21 | 0.83 | 0.4 |
| Leu22 | 5.0 | 1.4 |
| Trp23 | n.d. | n.d. |
| Lys24 | 0.23 | −0.4 |
| Leu25 | 0.73 | 0.3 |
| Leu26 | 27 | 2.4 |
| Pro27 | 0.051 | −1.3 |
| Glu28 | 0.24 | −0.4 |

"n.d." indicates a binding affinity below the detectable limit.

Figure 12:
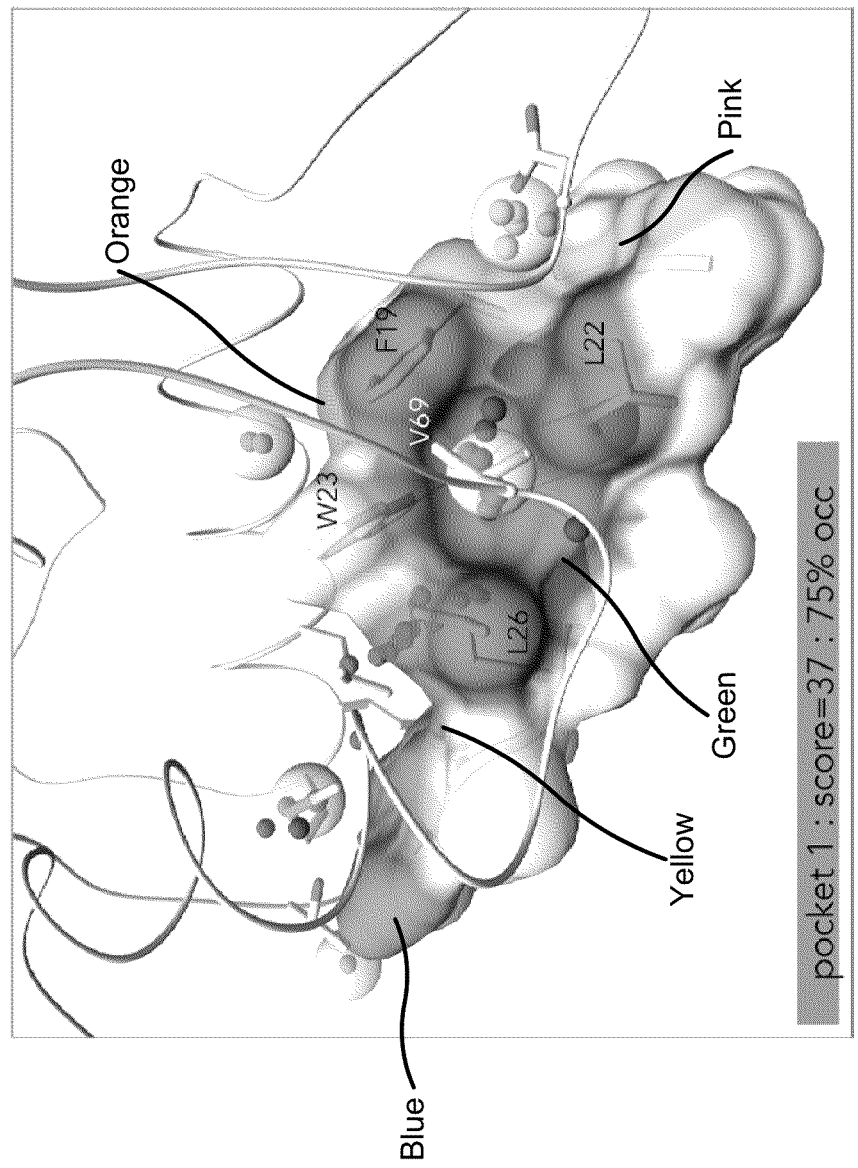
FIG. 12 is an illustration of mapping of the p53 surface of the Mdm2/p53 interface, highlighting pocket 1, formed by the three p53 hot spot residues (W23, F19, L26) and L22. The role of L22 in the formation of this pocket, which binds V69 from Mdm2, accounts for the residue's significant contribution to Mdm2/p53 affinity despite the low scoring pocket from Mdm2 to which it binds.

Meanwhile, the Leu22 of p53, whose alanine mutagenesis results in a 10 fold decrease in Mdm2/p53 binding affinity, interacts with the lowest ranked pocket 7 (score=12) but 100% occupied. A truly complete pocket analysis requires the mapping of both binding partners, because either surface may simultaneously function as both pocket and ligand, even for a helix-in-groove PPI such as Mdm2/p53. When the surface of the p53 helix is inversely mapped, Leu22 is involved in the formation of the most significant pocket (score=37, 75% occupied), which accommodates Val69 from Mdm2, as shown in FIG. 12. This dual role as ligand and pocket-lining residue is consistent with Leu22's significant contribution to Mdm2/p53 affinity despite the relatively low scoring pocket from Mdm2 to which it binds.

The system 300 calculates a range of additional pocket features as well. These include the pocket-centric and ligand-centric features presented, for Mdm2/p53, listed in Table II and the structure-based and alpha-cluster-centric features listed in Table III.

TABLE II

Pocket-centric and peptide-centric features of the Mdm2/p53 interface pockets.

| Rank | Color | # pocket atoms | Polar pocket atoms | Charged group | Peptide side chain resIDs | Peptide backbone resIDs | # peptide atoms | Polar peptide atoms | Peptide charged group |
|---|---|---|---|---|---|---|---|---|---|
| 1 | green | 19 | 3 | no | 23 | | 7 | 0 | no |
| 2 | yellow | 20 | 4 | no | 19, 23 | 19, 20, 23 | 13 | 2 | no |
| 3 | pink | 22 | 4 | no | 26, 27 | 26, 27 | 8 | 2 | no |
| 4 | teal | 15 | 5 | yes | 29 | | 3 | 2 | no |
| 5 | orange | 12 | 4 | yes | 29 | 28, 29 | 10 | 4 | no |
| 6 | blue | 12 | 7 | yes | 17 | | 5 | 2 | yes |
| 7 | purple | 9 | 2 | no | 22 | | 3 | 0 | no |

The complete set of PPI complexes from the 2P2I database that are listed in Table IV were used to perform this parameterization. 2P2I includes a total of 14 PPIs for which orthosteric inhibitors have been developed and for which apo, PPI complex, and iPPI complex structures have been experimentally solved. In the fitting, topographical mapping on the surface is performed from each PPI that is also targeted by a small-molecule inhibitor. An alpha-cluster, or pocket, is considered to be "occupied" if at least one atom from the peptide or inhibitor is within 1.6 angstrom of any alpha sphere center from that pocket.

TABLE III

Various structure-based and alpha-cluster-centric features of the Mdm2/p53 interface pockets

| index | color | atom-excl. space | tot. SA | pocket SA | alpha-clust SA | % nonpol | curv 1 | curv 2 | SA score 1 | SA score 2 | # alph. sph. | alpha-clust vol. | alpha-atom dens. | Alpha sph. vol. |
|---|---|---|---|---|---|---|---|---|---|---|---|---|---|---|
| 1 | green | 177 | 370 | 94 | 276 | 95% | 1.89 | 0.8 | 697 | 297 | 28 | 177 | 0.16 | 933 |
| 2 | yellow | 166 | 421 | 154 | 267 | 78% | 1.08 | 0.61 | 454 | 257 | 27 | 257 | 0.11 | 1366 |
| 3 | pink | 127 | 453 | 169 | 284 | 92% | 0.75 | 0.62 | 340 | 279 | 30 | 265 | 0.11 | 1272 |
| 4 | teal | 36 | 292 | 98 | 194 | 85% | 0.37 | 0.57 | 108 | 165 | 19 | 152 | 0.13 | 798 |
| 5 | orange | 23 | 279 | 98 | 181 | 82% | 0.24 | 0.62 | 66 | 173 | 11 | 133 | 0.08 | 912 |
| 6 | blue | 26 | 206 | 72 | 134 | 45% | 0.36 | 0.51 | 74 | 105 | 13 | 116 | 0.11 | 872 |
| 7 | purple | 3 | 151 | 58 | 93 | 92% | 0.05 | 0.5 | 7 | 75 | 7 | 65 | 0.11 | 539 |

TABLE IV

PDB-ID list for all PPI/iPPI structures used from the 2P2I database

| System (2P2I) | PPI (PDB-ID) | iPPI (PDB-ID) |
|---|---|---|
| Bcl2/Bax | 2XA0 | 4AQ3 |
| Bcl-xL/Bad | 2BZW | 2YXJ |
| Hpv-E2/Hpv-E1 | 1TUE | |
| Il-2/Il-2R | 1Z92 | 1PY2 |
| Integrase/LEDGF | 2B4J | 4E1N |
| Mdm2/p53 | 1YCR | 4ERF |
| Mdm4/p53 | 3DAB | 3LBJ |
| Menin/MLL | 4GQ6 | 4GQ4 |
| TNFalpha/TNFalpha | 1TNF | 2AZ5 |
| TNFR1-A/TNFR1-B | 1TNR | |
| Xdm2/p53 | 1YCQ | 1TTV |
| Xiap/Caspase | 1NW9 | 1TFT |
| Xiap/Smac | 1G73 | 2JK7 |
| ZipA/FtsZ | 1F47 | 1Y2F |

Figure 10:
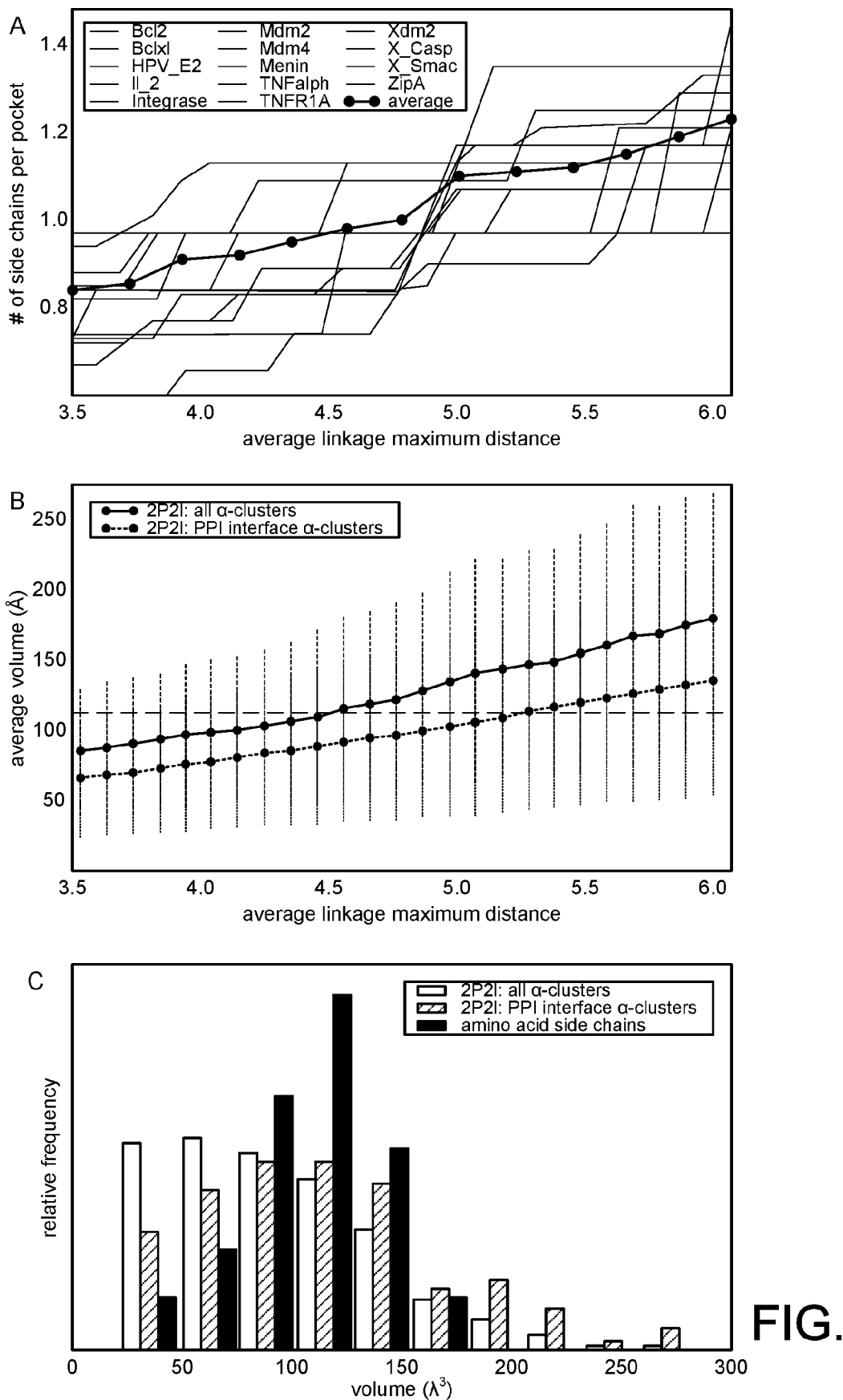
FIG. 10 panel A is a plot of the number of interacting peptide side chains per pocket as a function of the average linkage maximum distance for the 14 PPI interfaces in the 2P2I database. The average number of side chains per pocket is near unity from 4.6-4.8 angstroms indicating a promising range for fragment-centric clustering. Panel B is average and standard deviation of alpha-cluster volume as a function of average linkage maximum distance for the complete set of alpha-clusters and for the subset of interface alpha-clusters. The black dashed line marks 109.2 angstroms, the average volume of the 20 natural amino acids. Panel C are normalized histograms of the alpha-cluster volumes using the 4.7 angstroms average linkage maximum distance, overlaid with the histogram of amino acid volumes, for reference.

As shown in FIG. 10, the average number of side chains per pocket is near unity when the maximum average-linkage distance is within the range 4.6 to 4.8 angstroms. While the parameters was set to be 4.7 angstroms, however this is not intended to be a definitive assignment. Small variations will not significantly impact the overall clustering, but may allow the user to selectively merge or split certain pockets near the cutoff to customize an analysis. For example, for the Mdm2/p53 structure, used 4.6 angstroms was used in order to separate pockets 6 and 10 to facilitate comparison to the apo and iPPI structures in which these pockets are slightly more distinct A practical pocket-score should reflect a maximal affinity model, where the score is proportional to the affinity which can be expected to achieve between each pocket and a hypothetical complementary inhibitor fragment. As a single term, the total alpha-space of a fragment-centric pocket reflects both the surface area (SA) as well as the curvature associated with that interaction region. A unique SA and curvature-based metrics was developed to evaluate their correlation with total alpha-space. Two different intuitive metrics were established for curvature:

$$\text{curvature } 1 = \frac{\text{alpha-space}}{\text{pocket } SA} \text{ and}$$

$$\text{curvature } 2 = \frac{\text{desolvated alpha-cluster } SA}{\text{total alpha-cluster } SA}$$

for two simple SA-based pocket metrics:

$SA$ score 1 = curvature 1 × (desolvated pocket $SA$ + desolvated alpha-cluster $SA$) and $SA$ score 2 = curvature 2 ×

(desolvated pocket $SA$ + desolvated alpha-cluster $SA$)

Figure 11:
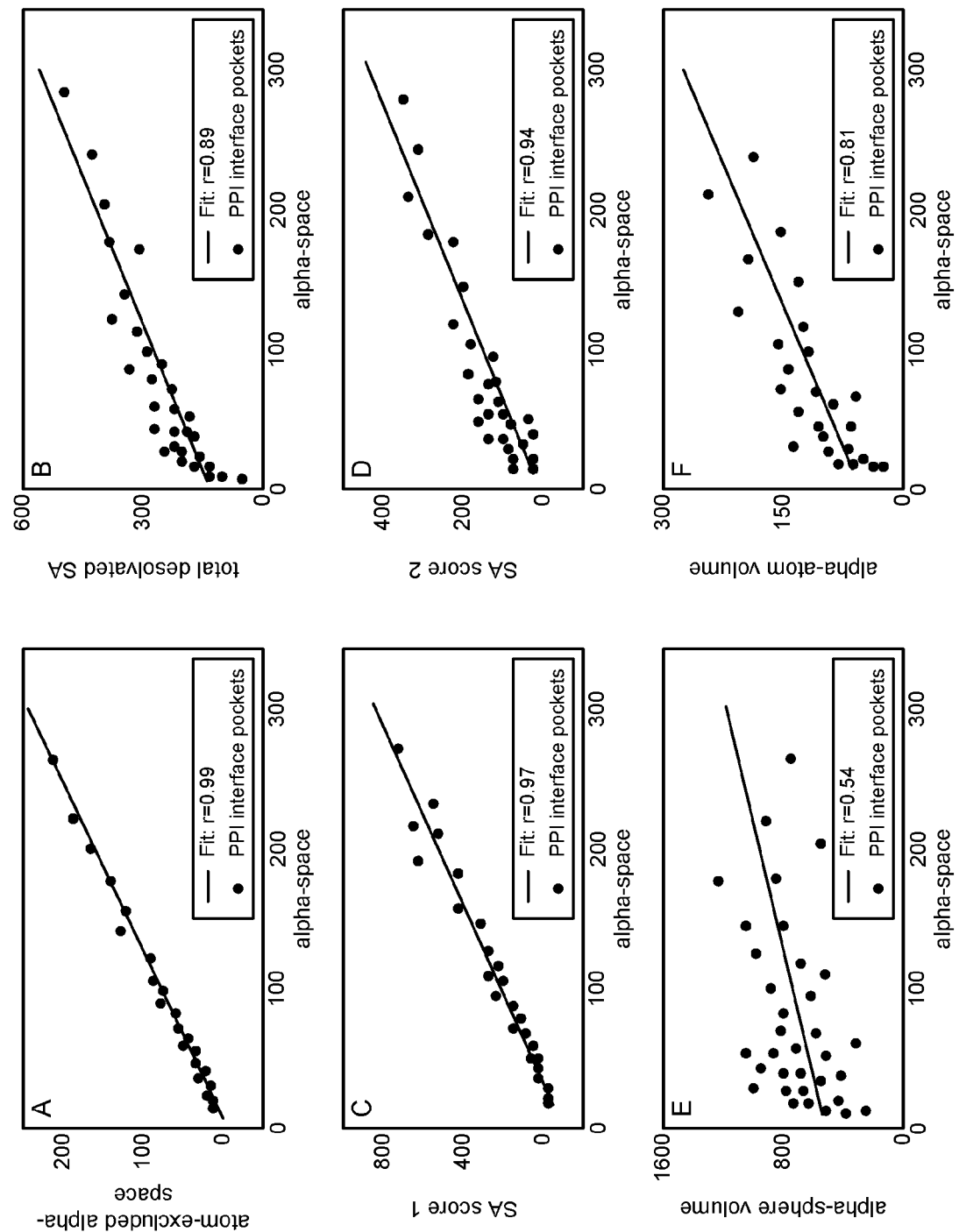
FIG. 11 panels A-F are scatter plots showing correlations of alpha-space with various pocket features for all interface pockets from the 14 2P2I PPI complexes along with a linear fit line for each plot. Panel A Atom-excluded alpha-space: r=0.99, panel B Total desolvated surface area for the alpha-cluster/pocket complex: r=0.89, panel C SA score 1: r=0.97, panel D SA score 2: r=0.94, panel E the union alpha sphere volume: r=0.54, panel F the union alpha-atom volume (or the alpha-cluster volume): r=0.81.

In FIG. 11, the alpha-space of all PPI interface pockets is plotted against the various volume and structure-based pocket metrics described: atom-excluded alpha-space, total desolvated SA, SA score 1, SA score 2, total alpha-sphere volume, and total alpha-cluster volume. The remarkably high correlations between total alpha-space and both SA score 1 (r=0.97) and SA score 2 (r=0.94) support that total alpha-space can be utilized as a strong proxy for a general curvature-weighted surface area metric. While the atom-excluded alpha-space has a more physical meaning, the application of alpha-space in pocket scoring as described herein is designed to represent not a physical volume, but a more abstract metric of general binding potential. Furthermore, the association of alpha spheres with fractional alpha-spaces, rather than full alpha-spaces, could compromise the pocket occupation model discussed below. Similarly, the advantage of evaluating pockets with alpha-space over these explicit SA-based scores derives from the ability to easily subdivide a pocket into occupied and unoccupied spaces due to the discrete nature of the individual alpha sphere/space pairs.

Pocket Matching Between Mdm2/p53 PPI and iPPIs.

The Mdm2/p53 interface is effectively targeted using both fragment-based and biomimetic inhibitor design. The nutlins, a set of cis-imidazoline small molecules that mimic the main four interaction points, were the first inhibitors discovered to modulate Mdm2/p53. Subsequent FBDD efforts led to the discovery of the current ultra-high affinity inhibitors that optimize these primary interactions and introduce additional, novel interaction points.

Two iPPI structures of Mdm2 are selected in complex with ultrahigh-affinity inhibitors emerging from each of these design strategies: a small fragment-based molecule (a piperidinone sulfone derivative) with $IC_{50}$ 0.10 nM (PDB: 4oaS) and a $_D$-peptide antagonist ($^D$PMI-δ) with $K_d$ 0.22 nM (PDB: 3tpx). FIG. 13 displays the mapping of each of these complexes, along with those of the native Mdm2/p53 PPI (PDB: 1ycr) and the apo state of Mdm2 (PDB: 1z1m). This mapping of Mdm2/p53 is expanded to include unoccupied pockets near the interface in addition to p53 contact pockets. The mapping of the apo Mdm2 has been focused using the interface atom list from Mdm2/p53. Quantitative results for the matching of the apo surface and the two iPPI interfaces to the native Mdm2/p53 interface are also presented in FIG. 13.

In the development of these picomolar inhibitors, mirror image phage display with chemical ligation and fragment-based screening methods led to the identification of three auxiliary interaction sites in the vicinity of the Mdm2/p53 interface but not utilized in the native Mdm2/p53 PPI. These are an acetate fragment binding region adjacent to the Leu22 interaction site (targeted by both inhibitors), a hydrophobic patch on the opposite side of the helix between the Trp23 and Leu26 binding pockets (targeted by $^D$PMI-δ), and the "glycine shelf", which is adjacent to the Phe19 binding pocket (targeted by the small molecule inhibitor). FCTM of these interfaces performed using the system 300 not only identifies each of these interaction regions as distinct pockets in the corresponding iPPIs, but identifies all three interaction regions as unoccupied pockets in the native Mdm2/p53 interface: pocket 7, pocket 10, and pocket 6, respectively (FIG. 13 panel A).

Figure 14:
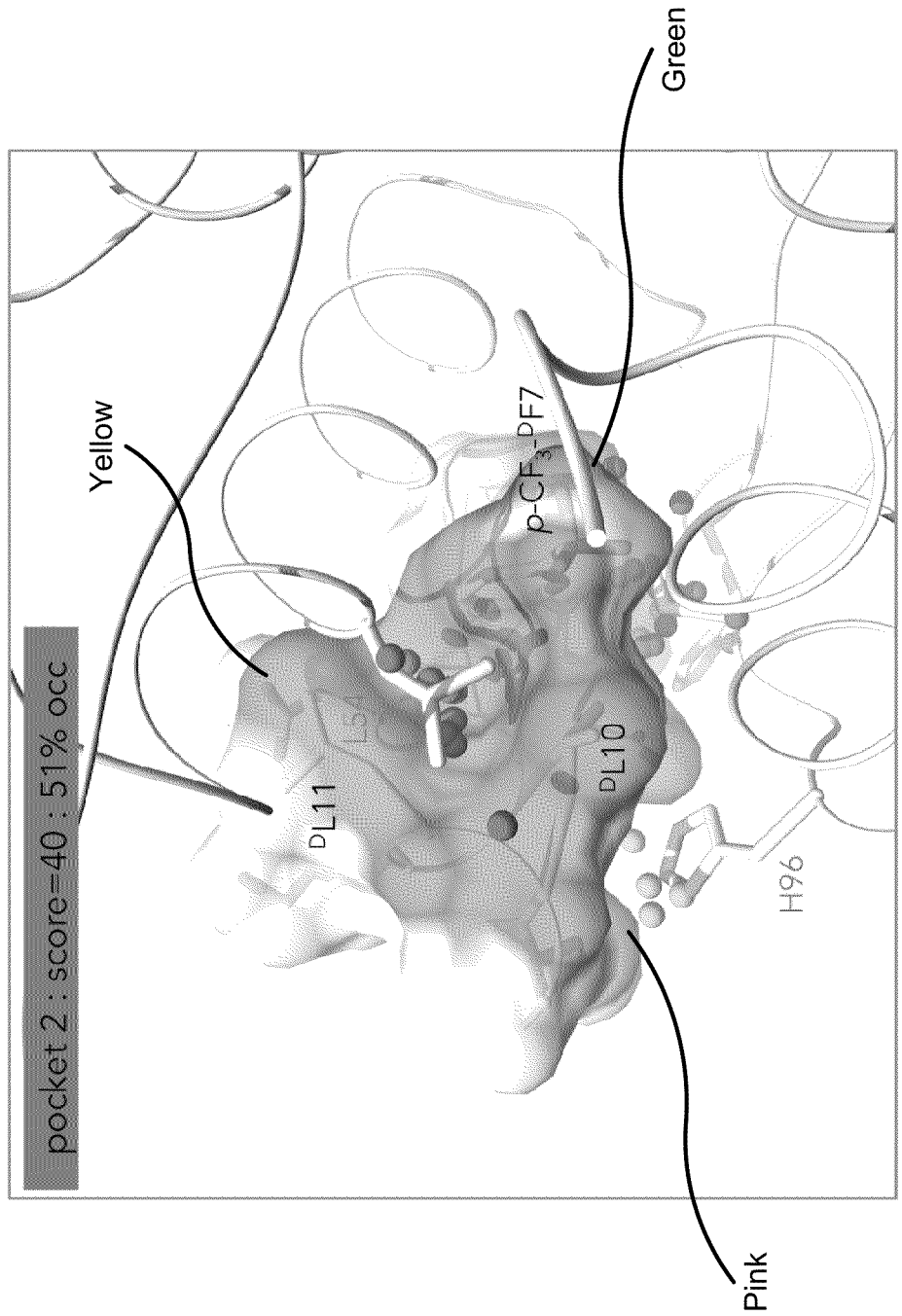
FIG. 14 is an illustration of mapping of the $_D$-peptide antagonist surface of the Mdm2/$^D$PMI-δ interface, highlighting pocket 2, formed by $^D$L11, p-CF$_3$-$^D$F7, and $^D$L10. The role of $^D$L10 in the formation of this pocket, which binds L54 from Mdm2, may account for the residue's contribution to Mdm2/$^D$PMI-δ affinity despite the low scoring pocket from Mdm2 to which it binds. Black residue labels are the $_D$-peptide; blue labels are Mdm2.

The targeting of pocket 7, despite its low pocket score, significantly enhances the affinity of both inhibitors by introducing favorable electrostatic interactions between the acetate fragment and Lys94, His96, and, for $^D$PMI-δ, His73. The affinity enhancement due to this fragment is roughly 20-fold for the small molecule inhibitor and, for $^D$PMI-α, a predecessor to $^D$PMI-δ, the alanine mutation of this acetate side chain reduces affinity by about 10-fold. For $^D$PMI-α, the alanine mutation of the Leu10, which targets pocket 10, reduces affinity by 4.5-fold. Pocket 10 has a particularly low pocket score, but, as with Leu22 of p53 discussed above, the targeting of this pocket forms a reciprocal pocket in the surface of $^D$PMI-δ (score=40) that is filled by Leu54 from Mdm2, as shown in FIG. 14. The specific affinity enhancement due to the targeting of pocket 6 by the tert-butyl fragment of the small molecule inhibitor is difficult to assess independently since this fragment and the ethyl fragment occupying pocket 2 were modified in tandem, but the initial targeting of this pocket in the development of its predecessor, AM-8553, enhanced affinity about 20-fold. Overall, this data makes it evident that the targeting of small, auxiliary pockets, detectable using the system 300, can significantly impact the productive design of competitive PPI inhibitors.

iPPI Optimizes Pocket-Fragment Complementarity.

Figure 15:
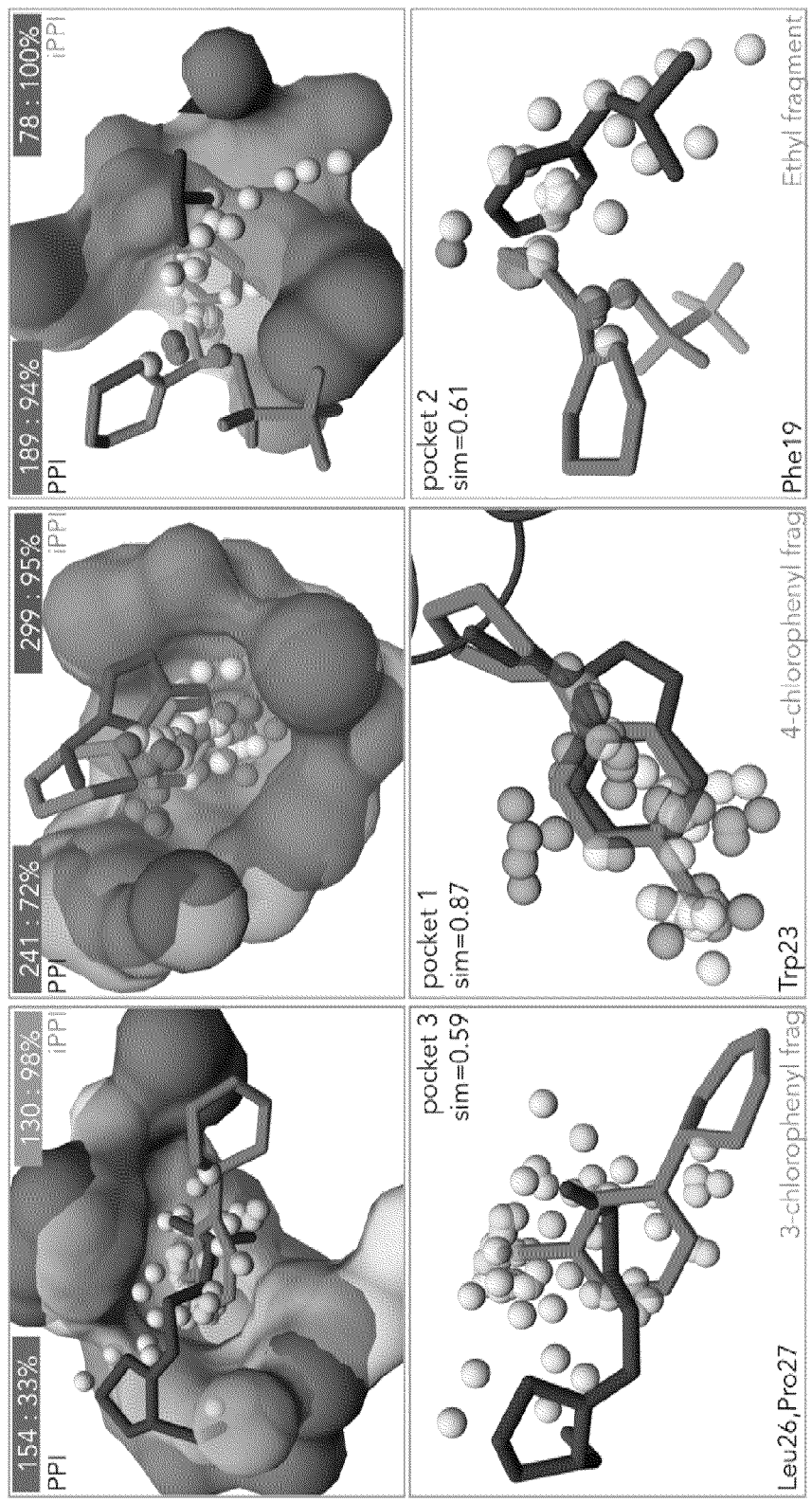
FIG. 15 is an illustration of pocket alignments between Mdm2/p53 (PPI) and Mdm2/small molecule inhibitor (iPPI) for pockets 1 (center), 2 (right), and 3 (left). For each pocket the pocket score and the percent occupation in the color-coded top bars is specified, for each pair of pockets the calculated similarity is specified, and the residue IDs of the native PPI fragments is specified.
Figure 16:
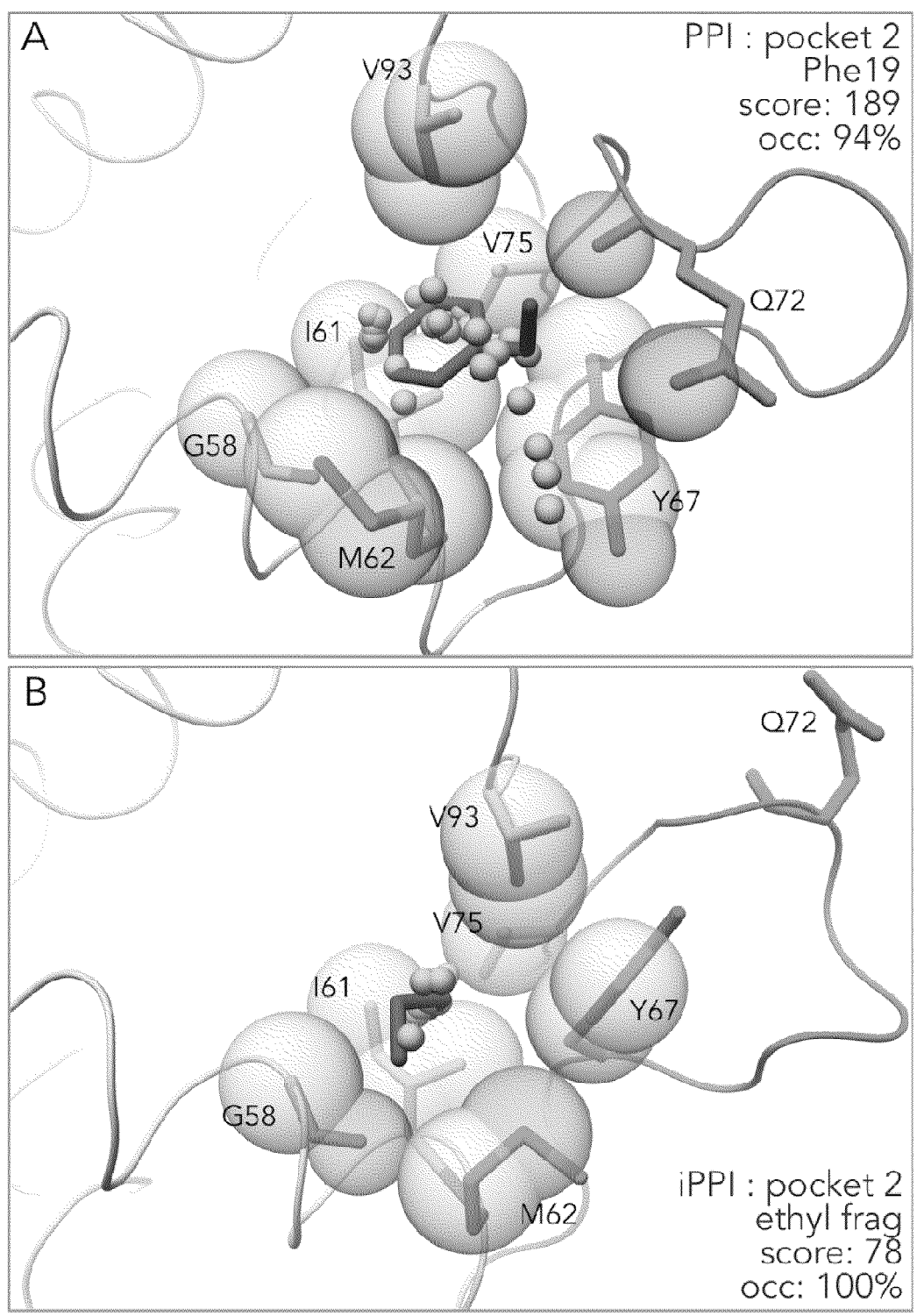
FIG. 16 is a residue-centric visualization of flexible pocket 2 at the Mdm2/p53 PPI (panel A) and the Mdm2/small molecule inhibitor iPPI (panel B). Pocket defining atoms are shown as transparent van der Waals (VdW) spheres colored by atom type.

The top three pockets from the Mdm2/p53 interface are associated with the primary hot spot residues from p53 and can be matched with three similar pockets from the iPPI interface between Mdm2 and the ultra-high affinity small molecule inhibitor, as shown in FIG. 15. For all three pockets, the pocket-fragment complementarity is higher in the iPPI. For pocket 1 and pocket 3, by individually aligning the matching pockets using the positions of shared pocket atoms, relationship between the unoccupied interaction space detected in the native PPI and the complementarity optimization measured for the iPPI is visualized. From the alignment of pocket 1, which is 72% occupied in the PPI, the ring from the 4-chlorophenyl fragment of the inhibitor overlays perfectly with the 6-member ring of Trp23, and the halogen extends directly into the unoccupied space identified in the PPI to achieve 95% pocket occupation. For Pocket 3, occupation is only 33% in the PPI; neither of the interacting residues (Leu26, Pro27) is optimally positioned to extend into the core of the pocket, leaving considerable unoccupied interaction space. Alternatively, the 3-chlorophenyl fragment from the iPPI approaches the pocket from a different angle, and the halogen extends directly into the space unoccupied in the PPI. Regarding pocket 2, the conservation of high pocket-fragment complementarity between the PPI and the iPPI (94% and 100% respectively) is a good example of functional pocket flexibility. This pocket, expanded in the PPI to accommodate the bulky side chain of Phe19, collapses significantly in the iPPI in response to the smaller ethyl fragment in order to retain complementarity with the ligand. As highlighted in FIG. 16, the structural mechanism for this pocket flexibility is driven primarily by secondary structure loop dynamics.

Comparison to FTMap®

Figure 17:
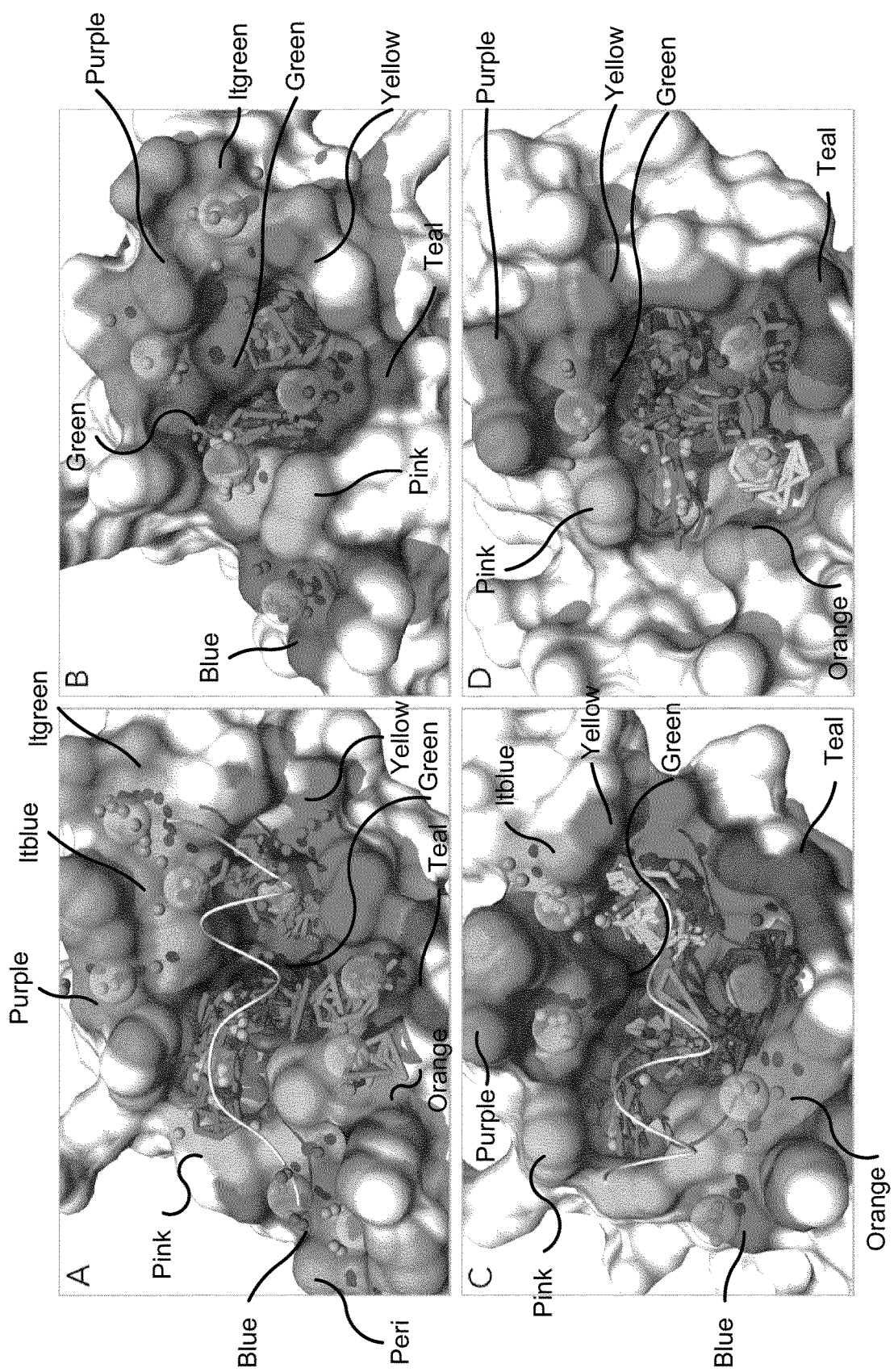
FIG. 17 panels A-D are illustrations comparing results from a conventional program (FTMap®) results, and results obtained using the system of FIG. 3 for the Mdm2 interfaces. Panel A is Mdm2/p53, panel B is Apo, panel C is Mdm2/$^D$PMI-δ and panel D is Mdm2/small molecule inhibitor. Probe clusters from FTMap® are represented as sticks, and alpha-centers determined from the system of FIG. 3 are represented as spheres. p53 peptide and $^D$PMI-δ are included for reference (no color).

FTMap® is a leading computational solvent mapping software, used to identify high quality interaction space at the protein surface. The topographical mapping results for the Mdm2 interfaces obtained using the system 300 were compared with the corresponding FTMap® results (see FIG. 17). In general, the results from the two methods are remarkably consistent. The high-quality interaction regions detected by FTMap® at the interfaces of Mdm2 overlap precisely with high-ranking alpha-clusters detected by the system 300. This pocket matching between methods is generally 1:1, aside from a few instances where a single pocket from system 300 will match with two overlapping probe clusters from FTMap® (see FIG. 17 panel A, pockets 1 and 3).

However, the results between the two methods are not identical. It was observed that the system 300 results in a more comprehensive coverage in the mapping of the interaction space. Several small auxiliary pockets, detected by the system 300 and directly targeted by the inhibitors described herein, go undetected in the FTMap® results. Additionally, for the apo state of Mdm2, FTMap® identifies only two of the seven pockets detected by system 300 (each of which can be matched to a pocket from the Mdm2/p53 interface). While these unidentified pockets may be reduced in size, their detection is critical for a continuous dynamic pocket model, especially for apo simulation where the full expansion of binding pockets may be rarely sampled events.

FCTM of the 2P2I Database

In order to test FCTM performed by the system 300 for a larger and more diverse data set, the system 300 was used to map a total of 24 protein surfaces (12 PPI/iPPI pairs) taken from the 2P2I database. The 2P2I database, which contains a total of 14 PPI/iPPI pairs, is weighted toward helix-in-groove type PPI interactions, but it does include several flatter and broader interaction interfaces, involving alpha helices, beta sheets, and loop regions. For the 12 systems included in this analysis, if multiple iPPI complexes were available in the 2P2I, the complex corresponding to the inhibitor with the highest binding affinity was selective. Table V includes a complete list of PDB IDs used in the analysis.

TABLE V

PDB-ID list for all PPI/iPPI structures used from the 2P2I database[5]

| System (2P2I) | PPI (PDB-ID) | iPPI (PDB-ID) |
| --- | --- | --- |
| Bcl2/Bax | 2XA0 | 4AQ3 |
| Bcl-xL/Bad | 2BZW | 2YXJ |
| Hpv-E2/Hpv-E1 | 1TUE | |
| Il-2/Il-2R | 1Z92 | 1PY2 |
| Integrase/LEDGF | 2B4J | 4E1N |
| Mdm2/p53 | 1YCR | 4ERF |
| Mdm4/p53 | 3DAB | 3LBJ |
| Menin/MLL | 4GQ6 | 4GQ4 |
| TNFalpha/TNFalpha | 1TNF | 2AZ5 |
| TNFR1-A/TNFR1-B | 1TNR | |
| Xdm2/p53 | 1YCQ | 1TTV |
| Xiap/Caspase | 1NW9 | 1TFT |
| Xiap/Smac | 1G73 | 2JK7 |
| ZipA/FtsZ | 1F47 | 1Y2F |

Figure 18:
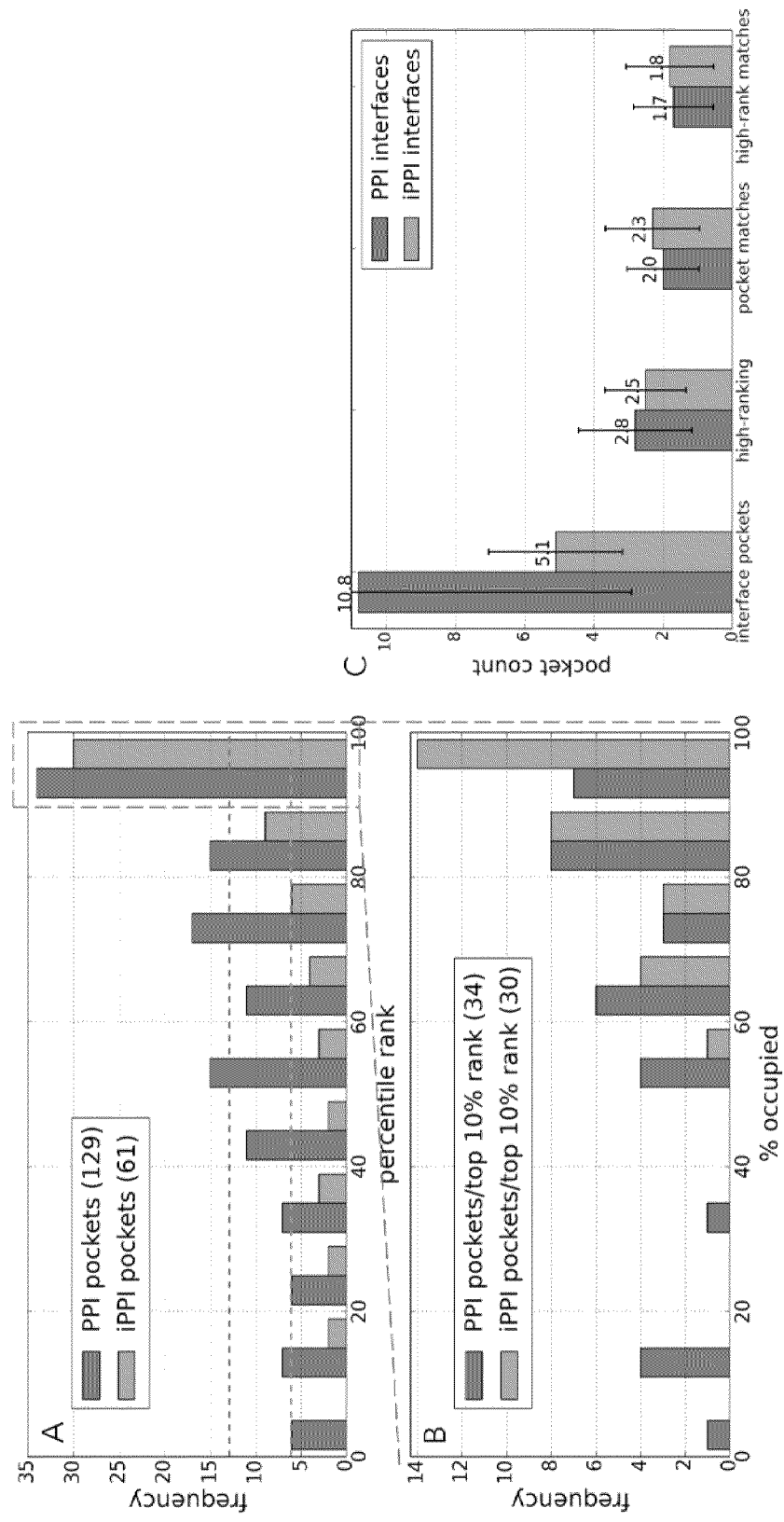
FIG. 18 panels A are histograms illustrating the distributions for the percentile rankings of all interface pockets for 12 PPIs (dark grey) and 12 iPPIs (light grey), ranking based on pocket scores. Dashed dark grey and light grey lines represent the statistically expected, uniform distributions for PPIs and iPPIs respectively. Panel B are histograms illustrating the distributions for the percent occupations of all high-ranking (90$^{th}$ percentile or above) PPI (dark grey) and iPPI (light grey) interface pockets. Percent occupation is calculated as the portion of a pocket's alpha-space that is associated with alpha-spheres in contact with peptide or inhibitor atoms. Panel C are mean values and standard deviations for the interface pocket matching data of the 12 PPI (dark grey) and 12 iPPI (light grey) complexes. Data presented include number of interface pockets, number of high-ranking interface pockets, number of high-ranking interface pockets with matches in the partner iPPI or PPI interface, number of these matches that also qualify as high-ranking.

A full topographical map accounts for all concave interaction space across the complete protein surface, subdivided into fragment-centric interaction regions. Each region is assigned a pocket score and is ranked among all other pockets in that protein. The rankings for the subset of pockets found at the interface of each of the 24 complexes was evaluated. As shown in FIG. 18 panel A, "high-ranking" pockets ($90^{th}$ percentile and above) are sharply enriched at the interfaces of the PPIs and the iPPIs, appearing 2.6 and 4.9 times their expected values. iPPI interfaces are nearly twice as enriched because, while the total number of PPI interface pockets (129) is nearly double the number of iPPI interface pockets (61), the total number of high-ranking pockets for each set is similar: 34 (PPIs), 30 (iPPIs). 25% of all PPI pockets are high-ranking pockets; 49% of all iPPI pockets are high-ranking pockets.

It was also evaluated whether the detected high-ranking interface pockets are being conserved between PPIs and corresponding iPPIs. For each high-ranking pocket at a PPI or iPPI interface, a "matching" pocket-similarity score above 0.40 is searched in the opposite interface. If such a similarity score is found, it is evaluated whether the matching pocket also qualifies as a high-ranking pocket. Table VI presents the system-by-system results for this analysis, and FIG. 18 panel C depicts the mean values from Table VI. On average, 71% of high-ranking PPI pockets can be detected at the respective iPPIs. Of these identified matches, 85% of them qualify as high-ranking pockets in the iPPI. Inversely, 92% of high-ranking iPPI pockets can be identified in the respective PPI interfaces, and 78% of these qualify as high-ranking in the PPI.

TABLE VI

Summary of topographical mapping and pocket conservation results for 12 PPI and 12 iPPI interfaces. For each protein complex the total number of pockets are listed for the complete protein surface, the number of PPI or iPPI interface pockets, the number of high-ranking interface pockets (90th percentile or above), the number of these high-ranking pockets that match to pockets in the partner interface, the number of these matches that also qualify as high-ranking pockets.

| | PPI | | | | | iPPI | | | | |
|---|---|---|---|---|---|---|---|---|---|---|
| System | Full surface | Interface | High-rank | iPPI match | iPPI high | Full surface | interface | High-rank | PPI match | PPI high |
| Bcl-2 | 108 | 13 | 4 | 3 | 3 | 107 | 6 | 4 | 4 | 3 |
| Bcl-xL | 104 | 13 | 5 | 4 | 4 | 107 | 10 | 4 | 4 | 4 |
| Il-2 | 104 | 9 | 3 | 1 | 0 | 97 | 6 | 2 | 0 | 0 |
| Integrase | 157 | 6 | 1 | 1 | 1 | 191 | 3 | 3 | 3 | 2 |
| Mdm2 | 67 | 7 | 3 | 3 | 3 | 77 | 6 | 3 | 3 | 3 |
| Mdm4 | 72 | 9 | 2 | 2 | 2 | 70 | 4 | 2 | 2 | 2 |
| Menin | 273 | 7 | 4 | 3 | 3 | 284 | 4 | 3 | 3 | 3 |
| TNFalpha | 202 | 33 | 6 | 1 | 1 | 178 | 3 | 2 | 2 | 1 |
| Xdm2 | 75 | 5 | 2 | 2 | 2 | 104 | 4 | 3 | 2 | 2 |
| Xiap (Casp) | 69 | 16 | 1 | 1 | 1 | 120 | 6 | 1 | 1 | 1 |
| Xiap (Smac) | 85 | 4 | 2 | 2 | 1 | 81 | 4 | 3 | 3 | 1 |
| ZipA | 110 | 7 | 1 | 1 | 0 | 102 | 5 | 0 | 0 | 0 |
| total: | 1426 | 129 | 34 | 24 | 21 | 1518 | 61 | 30 | 27 | 22 |
| mean: | 118.8 | 10.8 | 2.8 | 2 | 1.8 | 126.5 | 5.1 | 2.5 | 2.25 | 1.8 |

While generally most important iPPI pockets can be traced back to matching pockets in the original PPIs, the large standard deviations in this analysis indicates variation between systems. For example, in targeting the Il-2/Il-2R PPI, an interface already known to be flexible, the inhibitor interacts with 2 high-ranking pockets, but neither of these match with pockets from the PPI. In another variation from the norm, the inhibitor from the ZipA iPPI, a comparatively weak micromolar binder, targets five pockets, but because none of these qualify as high-ranking, the matching pockets in the PPI are simply not sought according to this particular analysis. However, the general picture emerging from this cross-interface analysis shows the iPPI to be established from a reduced set of the highest-ranking pockets engaged in the PPI.

The complementarity between high-ranking PPI/iPPI pockets and the peptide or inhibitor fragments they bind was also evaluated using the system 300. Pocket-fragment complementarity is expressed as the percent occupation of a pocket, calculated as described in method 200 and with reference to the pocket evaluation circuitry 304b of the system 300. FIG. 18 panel B illustrates that, generally, high-ranking PPI and iPPI interface pockets bind to their respective fragments with moderate to high complementarity. However, there is a distinct shift for high-ranking iPPI pockets toward higher pocket occupation; 47% of high-ranking iPPI pockets are occupied above 90% compared to 20% of high-ranking PPI pockets. Better complementarity may contribute to the generally high ligand efficiency (LE) documented for successful iPPIs. Furthermore, this analysis reveals that many high-scoring pockets are underutilized in native PPI interactions. From an inhibitor design perspective, these partially unoccupied pockets represent opportunities for complementarity optimization to gain a competitive edge over the native binders.

Thus, the system 300 represents a departure from existing geometry-based pocket detection in two central aspects. The most pronounced cavities in a protein surface are of particular functional interest as probable ligand binding sites or enzymatic active sites and have the potential to exhibit a classical druggability. The pockets associated with these sites tend to be large, concave, and isolated, which are the features typically sought by existing pocket detection software. Alternatively, PPI interfaces are marked by arrays of shallower pockets, with more subtle spatial separation. The strategy is to subdivide the broad PPI interaction regions into more localized fragment-centric interaction regions, reflecting the types of pockets targeted with FBDD to more precisely guide the global design of new chemotypes to match unique PPI interfaces. Furthermore, when mapping a complex, the pockets are evaluable for pocket-fragment complementarity at a resolution that is practical for the optimization of individual fragments.

The second divergence is that the system 300 provides a complete mapping of all interaction space across the surface or interface of interest. Cavity-centric methods tend to screen out what is appraised as insignificant interaction space and deliver only a small set of the most important pockets. This is useful to select for classical binding pockets in the surface, but leads to incomplete coverage when characterizing a PPI interface. The system 300 introduces a comprehensive surface map to illuminate the global topography of the interface. This is important for FBDD because, as seen for the high-affinity Mdm2/p53 iPPIs, even small pockets can provide guidance for the extension of fragment-based compounds and can provide opportunities to enhance ligand affinity. A complete interaction space model also sets the stage for a more nuanced modeling of protein surface dynamics. As seen for the Mdm2/p53 interface, the system 300 identifies and matches apo pockets to PPI pockets even for those that are greatly reduced at the apo state. This sensitivity should allow pockets to be tracked more continuously across a molecular dynamics trajectory, even if the size or quality of the binding pocket varies between different snapshots.

Accounting for the complete determinants of PPI affinity is a complex challenge, however the primary roles of the hydrophobic effect and of VdW interactions have been established and robustly reiterated. The pocket score determined by the system 300 serves as a practical metric reflecting two key structural features related to the hydrophobic effect—non-polar surface area and pocket curvature—to discern the approximate, relative druggabilities of fragment-centric pockets. The most valuable feature of this metric is its independence from interaction analysis, which allows for the treatment of apo structures in the absence of a binding partner. Similarly, the complementarity metric is not designed to yield provides a guide to the extent that pockets are being utilized and to detect the potential for the further optimization of pocket-fragment VdW interaction.

Contact Score

In some embodiments, the method 200 or any other method described herein may also include determination of a contact score between a protein surface and a chemical fragment, ligand, peptide, or other protein. The contact score may be calculated as the sum of the non-polar weighted alpha-spaces from the target protein surface that are associated with alpha-atoms that are "in contact" with or "occupied" by the "ligand" atoms or the chemical fragment, using a cutoff distance in the range of 1.4-1.8 angstrom inclusive of all ranges and values therebetween (e.g., 1.6 angstrom) as a measure for "contact" or "occupation". This contact score can be calculated as a total interface contact score, where the contact for all fragments in the ligand molecule or chemical fragment are summed. Alternatively, contact score can be reported at the fragment-centric resolution, in which contact scores will be calculated for each predefined chemical fragment or amino acid side chain individually.

In some embodiments, the ligand structure may also be mapped using the method 100 or the method 200 to detect the fragment-centric pockets in the surface of the ligand (this could be a small molecule, a peptide, or a protein). For this "inverse" mapping, contact score is calculated the same way as for the target protein, but the score associated with each alpha-atom occupied by the target protein is decomposed according to the relative ACSAs of each pocket-lining atom in the ligand associated with that alpha-atom, and these "inverse" contact scores are added to the ligand contact score for each respective fragment in the ligand, or to the entire ligand if calculating the complete contact interface.

In some embodiments, the chemical identity of the ligand atoms, the protein surface atoms, or both may be considered and contact alpha-space may be summed within sets of chemical combinations. For example, protein and ligand atoms may be classified into a set of pharmacophores (e.g., aromatic, aliphatic, h-bond donor, h-bond accepter, positive, negative, polar, and null). Contact alpha-space may be organized within "classes" of a pharmacophore depending on the identity of the pocket-lining atom associated with an alpha-space, the identity of the ligand atom occupying the alpha-atom associated with an alpha-space, or by considering the specific combination of the pocket-lining atom and the occupying ligand atom.

In some embodiments, the contact score associated with a set of chemical identities can be grouped together. For example, aliphatic and aromatic interactions may be grouped into a single non-polar class, and the contact score may be calculated as the sum of the nonpolar/nonpolar contact alpha-space.

Contact scores for total interfaces or by fragment may be calculated across a molecular dynamics trajectory or for a set of snapshots in different configurations, and ensemble average contact scores can be calculated for the full surface or by fragment.

Alpha-spaces associated with unoccupied alpha-atoms can also be summed to organize unoccupied interaction space, either at the full interface resolution or by fragment-centric pocket. Unoccupied interaction space can be targeted in the extension or design of chemical fragments to improve pocket-fragment complementarity. Ensemble average values for unoccupied pocket space by d-pocket can also be calculated to identify stable, targetable, unoccupied interaction regions at the protein surface.

Pocket Communities

Figure 22:
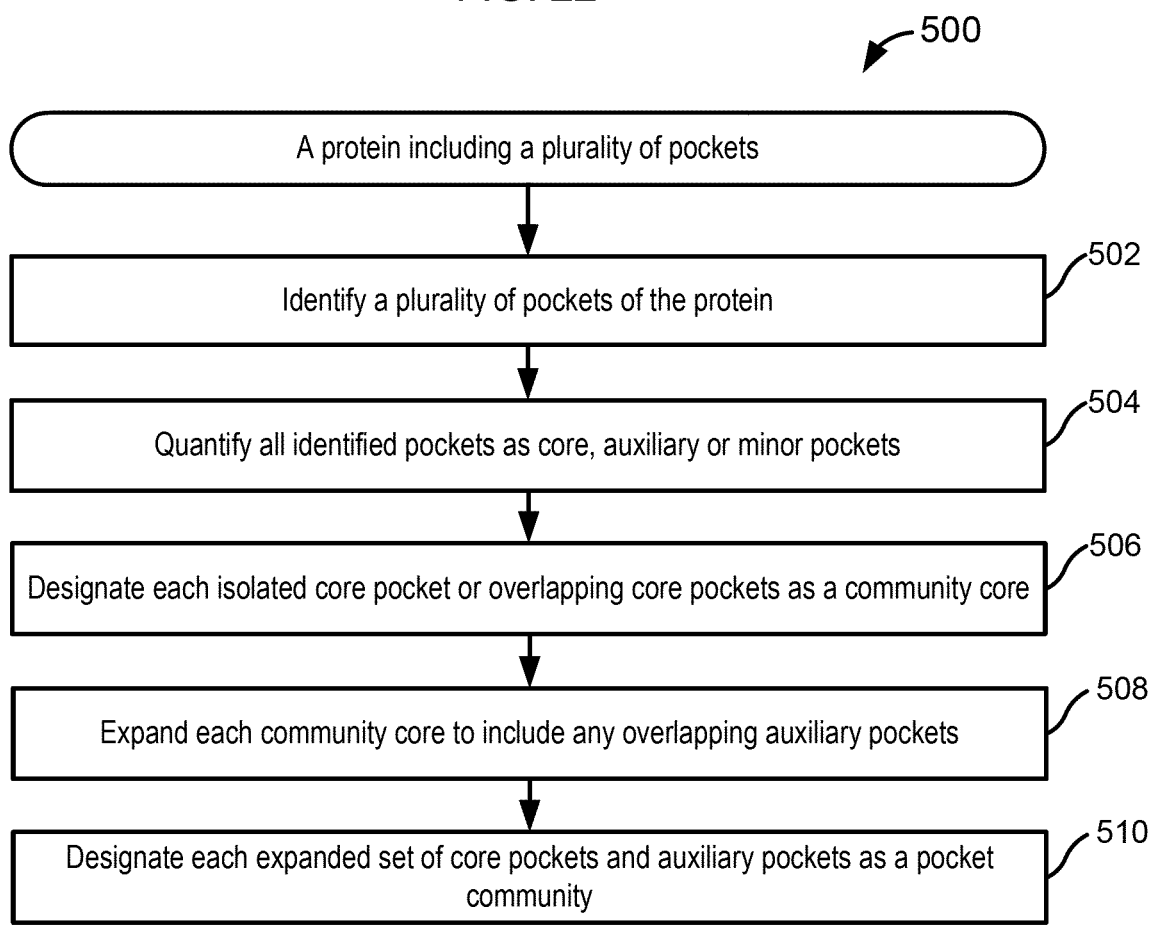
FIG. 22 is a schematic block diagram of a computing device that can be included in the system of FIG. 3 specifically programmed to execute the pocket identification module and the pocket evaluation module, for identifying and evaluation pockets, respectively and find chemical fragments that can engage in a PPI and/or iPPI with the pocket.

Druggable PPI interfaces are typically defined by multiple fragment targetable interaction regions in close proximity, which often include one or several particularly important anchor interactions. FIG. 22 is a schematic flow diagram of a method 500 for detecting potentially druggable protein surface regions pocket on the surface of a protein.

The method 500 includes identifying a plurality of pockets of the protein at 502. The plurality of pockets may be identified using any suitable method, for example the method 200. All identified pockets are quantified as core pockets, auxiliary pockets, or minor pockets at 504, by employing the pocket score. In some embodiments, the core pocket and auxiliary pocket score cutoffs may be set to 100 and 30, respectively. However, any other suitable pocket score cutoff may be used for the core pocket and/or the auxiliary pocket assignment.

The core pockets serve to initiate pocket communities. Each isolated core pocket or each set of overlapping core pockets is designated as a community core at 506. Each community core is then expanded to include any overlapping auxiliary pockets at 508. Each expanded set of core pockets and auxiliary pockets is designated as a pocket community at 510, which represents potentially druggable protein surface regions.

The pocket community method 500 allows for pocket overlap between distinct communities and overlapping communities are not consolidated. To qualify as overlapping pockets—in both core pocket consolidation and auxiliary pocket expansion—a pair of pockets may satisfy two conditions: (1) share at least one pocket atom; and (2) if the pockets point away from each other, the angle between their directional pocket vectors may not be greater than 90 degrees. The second condition strengthens the prediction of pocket community co-targetability, which is included to avoid grouping together pockets that do share atoms but face opposite directions. A pocket's directional vector, is defined from the centroid of its pocket atoms to the centroid of its alpha-cluster. The community score, which is the sum of all pocket scores (core and auxiliary) within a community, can be used to help detect potentially druggable protein surface regions.

2P2I Dataset: Pocket Communities

This method 500 is intended to detect fragment-based drug-targetable surface regions from the surface structure alone. To validate and to leverage the observed enrichment of high-scoring pockets at iPPIs, pocket communities as described with respect to the method 500 may be used to search the protein surface for overlapping clusters of high-scoring pockets.

The performance of pocket communities to identify the known druggable surface regions from the 12 iPPIs in the 2P2I dataset is studied. In 8 out of 12 structures, the iPPI interface is identified as the #1 ranked pocket community. In 11 out of 12 structures, the iPPI interface is identified in the top 3 ranked pocket communities. In 9 out of the 11 identified iPPIs, the druggable interface is represented by a single pocket community, otherwise, two pocket communities represent the interface. Table VII shows the high precision detection of the druggable interfaces.

TABLE VII

Ranking of pocket communities identified at iPPI interfaces

| system | Pocket Communities at iPPI Interfaces | | Pocket Community Coverage of iPPI Interface Pockets | | |
|---|---|---|---|---|---|
| | rank | #pock | #pock cover | #pock miss | #pock out |
| Bcl-2 | 1.2 | 5.3 | 5 | 0 | 1 |
| Bcl-xL | 1 | 11 | 8 | 0 | 3 |
| HPV-E2 | 1 | 8 | 4 | 0 | 4 |
| Il-2 | 2 | 2 | 2 | 1 | 0 |
| Integr. | 1 | 6 | 3 | 0 | 3 |
| Mdm2 | 1 | 5 | 5 | 0 | 0 |
| Mdm4 | 1 | 5 | 4 | 0 | 1 |
| Menin | 3.5 | 7.5 | 3 | 0 | 8 |
| TNFa | 2 | 5 | 3 | 0 | 2 |
| Xdm2 | 1 | 3 | 3 | 0 | 0 |
| Xiap | 1 | 4 | 2 | 0 | 1 |
| ZipA | — | — | 0 | 1 | — |

For 10 out of 11 predicted iPPI interfaces, the pocket communities account for 100% of the core and auxiliary pockets in contact with the ligand. For the 11th identified iPPI interface, there are, on average, 2.1 unoccupied pockets included in the corresponding pocket communities. In practice, these unoccupied pockets may represent viable auxiliary pockets yet to be targeted.

Figure 19:
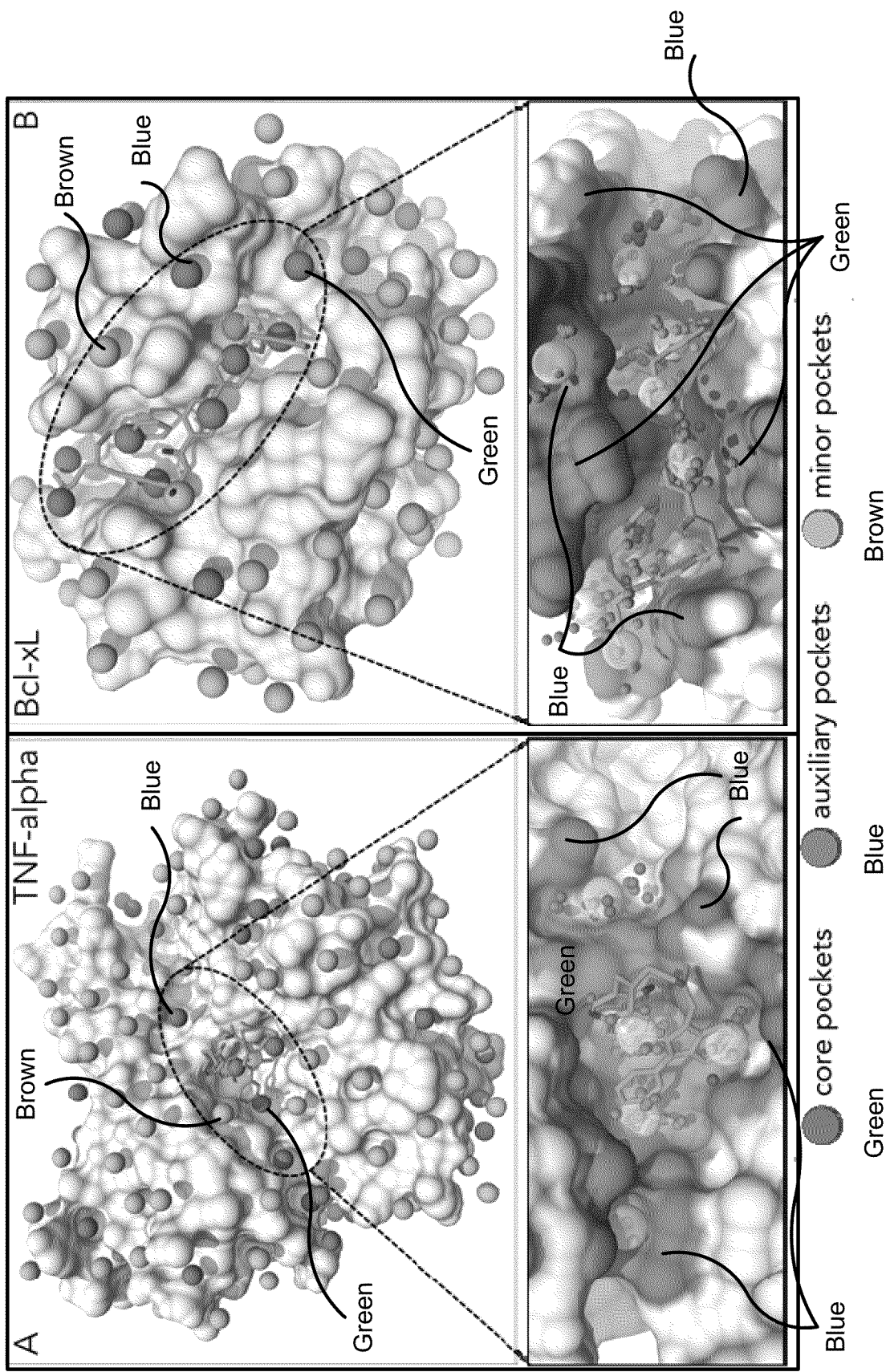
FIG. 19 are illustrations of pocket communities identified in various proteins; panel A and panel B of FIG. 19 are visualizations of all fragment-centric pockets of a TNF-alpha and Bcl-xL protein, respectively, and include an enlarged view of a core pocket and auxiliary pocket of each protein.

For example, FIG. 19 panels A-B are illustrations of pocket communities identified in various proteins. Panel A and panel B of FIG. 19 are visualizations of all fragment-centric pockets of a TNF-alpha and Bcl-xL protein, respectively, and an enlarged view of a core pocket and auxiliary pocket of each protein. Pocket communities are identified as high-scoring clusters of core and auxiliary pockets and represent potentially druggable surface regions. Each pocket is represented by a single sphere positioned at the centroid of its alpha-cluster. The spheres are colored by pocket classification: core pockets (green), auxiliary pockets (blue), and minor pockets (brown).

The respective fragment-based inhibitors are displayed as the stick structure shown in FIG. 19 panels A and B. The lower panels, are enlarged views of the specific pocket communities identified at the known iPPI interfaces. For each core and auxiliary pocket in each community, the detailed alpha-cluster is shown as small spheres (colored by pocket classification) and the alpha-cluster centroids are shown as transparent larger spheres. Pocket atoms in the surface of the proteins are colored by pocket classification. The TNF-alpha pocket community (FIG. 19 panel A) contains 2 core pockets, 3 auxiliary pockets, and community score=368. The Bcl-xL pocket community (FIG. 19 panel B) contains 5 core pockets, 6 auxiliary pockets, and community score=1208.

Figure 20:
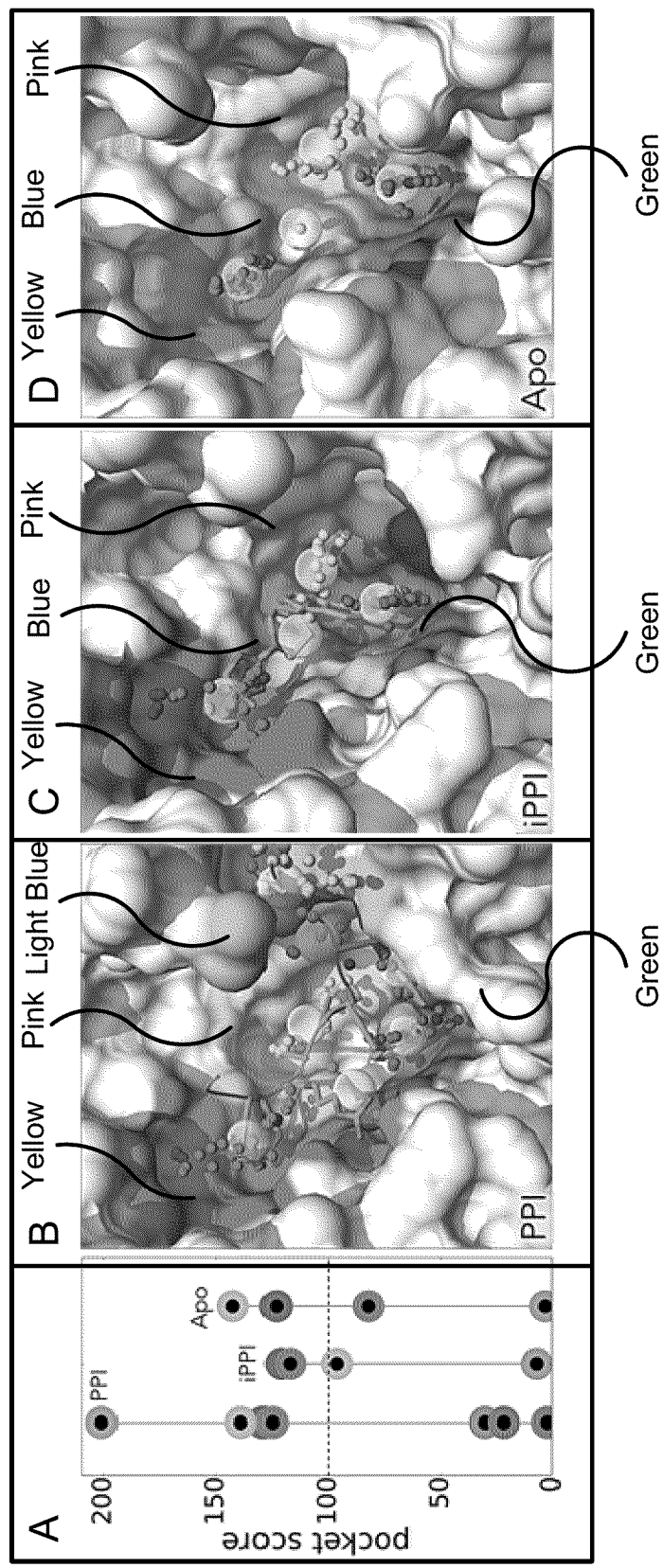
FIG. 20 panel A is a plot of pocket score of PPI, iPPI and apo protein surfaces of Menin; panel B, panel C and panel D of FIG. 20 are visualization of the PPI, iPPI and apo protein surfaces of the protein.

FIG. 20 panel A is a plot of pocket score of PPI, iPPI and apo protein surfaces of Menin. Panel B, Panel C and Panel D of FIG. 20 are visualization of the PPI, iPPI and apo protein surfaces of the protein. As shown in FIG. 20 panel A, each fragment-centric pocket at the respective interface is represented by a colored ring along the pocket score axis: PPI (FIG. 20 panel B), iPPI (FIG. 20 panel B), and apo (FIG. 20 panel C). Matching pockets are designated by matching ring color. In the surface structures to the right, alpha-clusters and pocket atoms are colored to match their respective ring colors. Alpha-cluster centroids are shown as transparent spheres. Binding partners are shown in red. The green, yellow, and pink pockets are well conserved across all three surface states.

The performance of pocket communities determined using the method 500 was also tested to detect drug-targetable communities in the corresponding apo structures near the known iPPI interfaces. For 5 out of 9 apo structures, the druggable interface can still be identified as the #1 ranked pocket community, and 1 more interface is identified by the #2 ranked pocket community. For the remaining 3 apo structures—Il-2, Bcl-xL, and ZipA—no pocket communities are identified at the known iPPI interfaces. It should be appreciated that an interface may not register as a pocket community unless at least one core pocket can be detected. However, for the 3 apo interfaces that do not register as pocket communities, several fragment-centric pockets scoring very close to the core pocket score cutoff were observed, indicating that the method 500 is sensitive to their latent druggability.

2P2I Dataset: Ligand—Alpha Cluster Volume/Shape Correlation

In order to highlight the capacity for alpha-clusters to serve as mock molecular binders, the volumetric correlation and shape similarity between the bound PPI inhibitors and the corresponding sets of contact alpha-clusters was evaluated. For the correlation between the total contact alpha-cluster volume and the total ligand volume, r was calculated as 0.77. This demonstrates a general volumetric correlation, but to evaluate the mock ligand feature more precisely, the calculated volumes of the specific alpha-atoms representing unoccupied interaction space as well as parts of the inhibitor molecule not in direct contact with the surface (i.e. outside 4.5 angstrom from the protein surface) may be omitted. For this corrected correlation between the occupied alpha-atom volume and the surface-contact ligand volume, r was calculated as 0.92.

Figure 21:
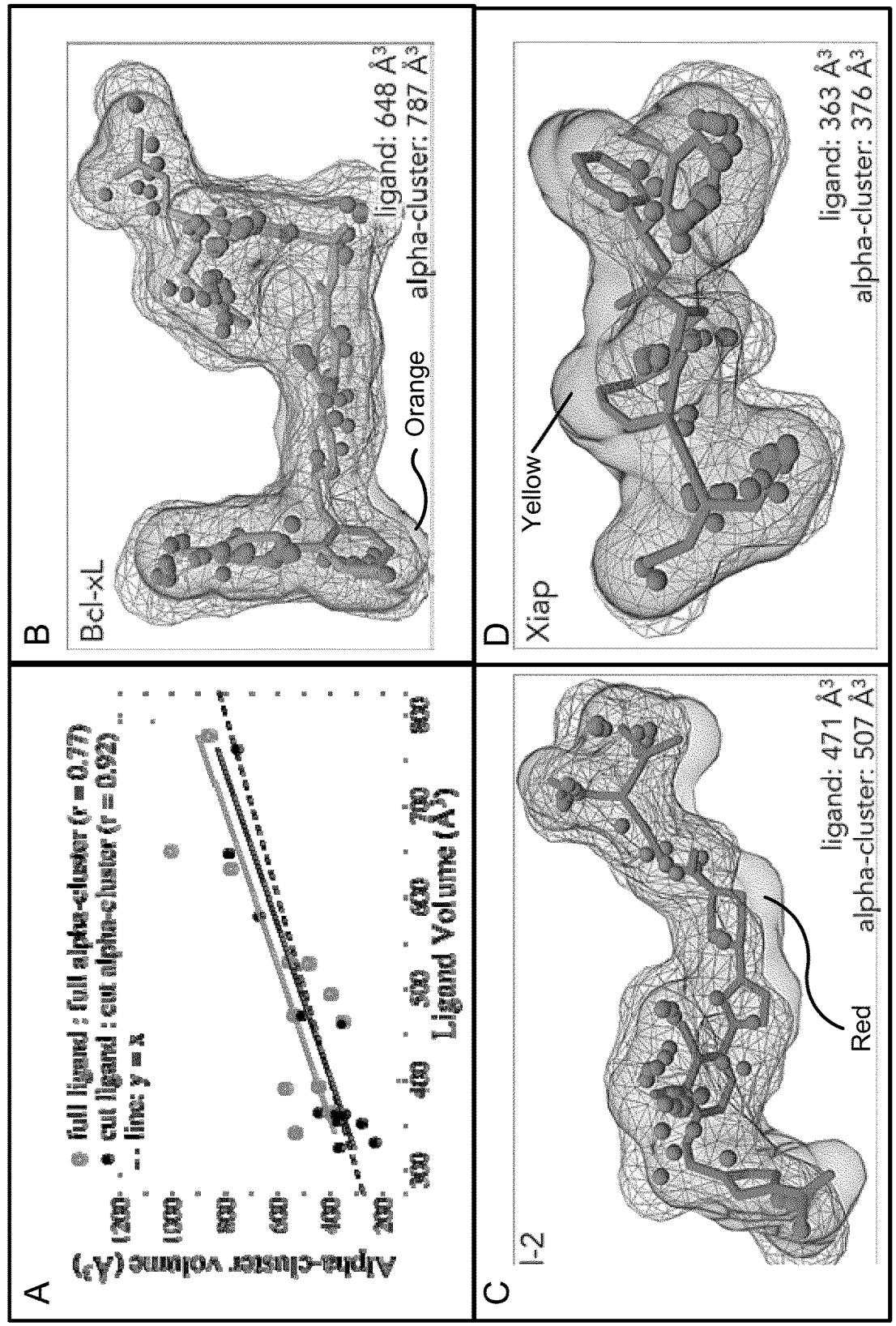
FIG. 21 panel A is a plot of correlation between ligand volume and contact-alpha cluster volume; panel B, panel C and panel D of FIG. 21 illustrate the shape similarity between the ligands that bind to Bcl-xL, Il-2 and Xiap, respectively and the corresponding cluster of contact alpha-atoms from the mapping of each iPPI interface.

For example, FIG. 21 panel A is a plot of correlation between ligand volume and contact-alpha cluster volume. Panel B, panel C and panel D of FIG. 21 illustrate the shape similarity between the ligands that bind to Bcl-xL (orange), Il-2 (red) and Xiap (yellow), respectively and the corresponding cluster of contact alpha-atoms from the mapping of each iPPI interface. Furthermore, as shown in FIG. 21 panel A, the linear fit for these corrected volumes is quite similar to the line y=x. This result demonstrates that alpha-clusters roughly approximate the actual size of corresponding molecular ligands.

Expanding further, the correlation between ligand volume and contact alpha-cluster volume is plotted and evaluated for 12 iPPIs from the 2P2I database in FIG. 21 panel A. Hollow circles are a plot of full ligand volume against the volume of the full alpha-cluster after merging the alpha-atoms of all ligand-contact pockets (r=0.77). Solid circles are a plot of the volume for a reduced set of ligand atoms, excluding ligand atoms not in contact with the protein surface, against the reduced alpha-cluster, excluding alpha-atoms not in contact with the ligand (r=0.92). Three example systems were used to illustrate the shape similarity between the ligands that bind to each of these systems and the corresponding cluster of contact alpha-atoms from the mapping of each iPPI interface: Bcl-xL (FIG. 21 panel B), Il-2 (FIG. 21 panel C), and Xiap (FIG. 21 panel D). Alpha-atom centers are shown as small spheres and the shape of each contact alpha-cluster is shown in wire representation. The ligands are shown simultaneously in stick representation and as transparent molecular surfaces. The volumes listed are for the reduced ligand and the reduced alpha-cluster.

In some embodiments, the volume overlap between an alpha-cluster (defined by a single fragment-centric pocket or by a combined set of fragment-centric pockets) and a docked or otherwise positioned ligand molecule can be utilized to evaluate the degree of structural complementarity between the target pocket, or set of pockets, and the proposed ligand. This metric can be applied to establish the relative complementarity between a set of proposed ligand molecules or to rank the set according to pocket-ligand complementarity.

Dynamic Topographical Mapping (DTM) and Surface State Clustering (SSC)

In some embodiments, an alignment free DTM approach for tracking fragment-centric pockets and pocket modulation across molecular dynamics trajectories may also be used. The DTM method is an extension of the pocket matching method as described before herein. A dynamic pocket entity, or "d-pocket," is introduced as well as several d-pocket features that reflect pocket ensemble properties, including pocket score, pocket stability, pocket integrity, and pocket modularity. SSC is a clustering approach that utilizes the variation in sets of the d-pockets co-exhibited at the PPI interface to cluster molecular dynamics trajectories according to surface state and to evaluate the similarity and variation between the different configurations of the protein surface. DTM may be integrated with the method 100 as described before herein for pocket matching.

The protein surface mapping method 100 is an alpha sphere-based model used to detect and characterize localized, fragment-centric interaction regions distributed across the protein surface. Mapping the structure of a PPI or iPPI interface will detect a set of fragment-centric pockets, each representing a localized concave interaction region, which generally results in a comprehensive coverage of the protein surface. The map is a guide to the spatial distribution and quality of fragment-centric interaction points utilized by a ligand, peptide, or protein binding partner. However, a biological protein surface is continually engaged in dynamic fluctuation, with each distinct conformation sampled from a molecular dynamics simulation resulting is a variation of this fragment-centric interaction map.

As described before, with the pocket matching method, a fragment-centric pocket can be tracked between different conformational states by identifying and associating pockets defined by similar sets of pocket-lining atoms. Using the DTM and SSC methods, it is possible to identify, whether fragment-centric pockets engaged in a PPI or iPPI interface could also be detected in the apo state of that interface. The results provide a high-resolution characterization of which fragment-centric pockets that engage in intermolecular interaction in the complex states are also detectable in the apo state, how the features of these pockets change from one state to another, and which pockets are not detectable in the apo state.

In some embodiments, the DTM method includes detecting all fragment-centric pockets at an interface of interest or interaction points. The pockets may be detected using the method 100 or any other method described herein.

For simulations of PPI or iPPI complexes, interface pockets are selected based on ligand contact, detected if there is proximity between any ligand atom and an alpha-atom from a fragment-centric pocket, using a cutoff distance in the range of 1.4-1.8 angstrom inclusive of all ranges and values therebetween (e.g., 1.6 angstrom). For apo state simulations, protein conformations can be aligned to a crystal structure of a corresponding PPI or iPPI complex and the crystallized binding partner can serve as a proxy ligand to detect ligand-pocket contact.

Similar fragment-centric pockets detected across the trajectory are associated into an array of pocket ensembles. Each ensemble represents a dynamic fragment-centric pocket, or "d-pocket". A n×n distance matrix is generated, where n is the total number of interface pockets among all included structures from the trajectory. To calculate a pairwise pocket distance, $d_{J,K}$, between pockets J and K, each pocket is represented by its pocket lining atoms as a one dimensional binary array, P:

$$P=[a_1, a_2, \ldots, a_i]$$

where i is the total number of heavy atoms in the protein structure, and $a_k=1$ if atom k is in pocket P and $a_k=0$ if atom k is not in pocket P. The Jaccard distance between pairs of pockets is then evaluated as:

$$d_{J,K} = \frac{\sum_k |P_{i,J} - P_{i,K}|}{\sum_k \{P_{i,J} + P_{i,K}\}}$$

This formula calculates the portion of all pocket-lining atoms that is dissimilar between the two pockets. The values range from 0, the distance between two identical pockets, to 1, the distance between two pockets with zero shared pocket-lining atoms. The pairwise pocket distance matrix is then clustered into d-pockets according to average linkage criteria using a clustering tool (e.g., the SciPy hierarchical clustering package) and a predetermined distance parameter. In some embodiments, the predetermined distance parameter may be in the range of 0.5 to 0.9 inclusive of all ranges and values therebetween (e.g., 0.7). However, the value of the distance parameter may be modified to tune the stringency of pocket association.

Using the DTM method, it may be possible for two pockets within a single interface conformation to be associated with the same d-pocket, since adjacent intra-interface pockets do express similarity in the overlap of their respective pocket-lining atoms. This may add consistency to and reduce noise in the definition of d-pockets that exhibit fluctuations in size near the clustering threshold. In this case, intra-interface pockets are then merged for the purpose of evaluating d-pocket ensemble statistics.

In some embodiments, the DTM method may be performed at the pocket-community level in which case only pocket-communities are included in the analysis and the atoms within the complete pocket-community are merged to represent a single interaction region. These interaction regions are then treated as pockets and clustered as in fragment-centric DTM.

DTM at the pocket-community level may be utilized to identify stable interaction regions with promising druggability potential. The degree of alpha-space anti-correlation between d-communities across a molecular dynamics trajectory can indicate potential allosteric activity between distinct pocket-communities or protein surface interaction regions.

DTM may also be used to cluster virtual screening results according to which ligand interactions co-target similar sets fragment-centric pockets. In this case, interface pockets are screened for direct ligand contact, and so the "surface state" of each protein surface with either a docked or simulated ligand will be defined by the binding pose of the ligand.

In another embodiment, the DTM method is performed in an alignment-dependent manner, for which the set of configurations from the molecular dynamics trajectory are each structurally aligned to a selected reference structure, which may be the crystal structure for that protein system, and individual fragment centric pockets are clustered into d-pockets according to the spatial proximity of the respective alpha-cluster centroids (instead of using the similarity in the sets of pocket lining atoms as described before). The pairwise pocket distance matrix is established from the Euclidean distances between pairs of alpha-cluster centroids. The matrix is then clustered into d-pockets according to average linkage criteria (or complete linkage criteria) using a clustering tool (e.g., the SciPy hierarchical clustering package) and a predetermined distance parameter. In some embodiments, the predetermined distance parameter may be in the range of 3.0 to 6.0 angstrom inclusive of all ranges and values therebetween (e.g., 4.5 Å). However, the value of the distance parameter may be modified to tune the stringency of pocket association.

The "surface state" of an interface observed in a particular conformation can be defined by the set of d-pockets co-represented across the protein surface. SSC is used in order to organize the trajectory into clusters of snapshots that express similar surface states. Each surface state cluster may represent a different binding mode accessible to that protein surface. A m×m distance matrix is generated, where m is the number of snapshots being evaluated from the trajectory. Each snapshot is represented by a surface state vector, S, of length j, where j is the total number of d-pockets identified in the trajectory using DTM. The value of each element in S indicates whether or not the corresponding d-pocket is observed in that particular surface state. The value is 0 if the d-pocket is absent and, if present, the value is taken to be the pocket score (calculated as described previously) of the fragment-centric pocket representing that d-pocket. The weighted Jaccard-like distance between two surface states P and Q is then evaluated as:

$$d_{P,Q} = \frac{\sum_j |S_{J,P} - S_{J,Q}|}{\sum_j \{S_{J,P} + S_{J,Q}\}}$$

The pairwise surface state distance matrix is then clustered using average linkage criteria with a distance parameter set to 0.5 by default. Because the surface state distance is weighted by pocket score, SSC can detect surface state variation even between pockets representing the same d-pocket. Thus, ensemble statistics for a d-pocket are more meaningful if evaluated for each d-pocket subset within each clustered surface state, as opposed to evaluating statistics for the full d-pocket. This subtlety is relevant for cases where a similar set of pocket-lining atoms exhibit a different pocket shape depending on the surface state. While this information is muted in the use of binary pocket vectors for DTM, it can be recovered in the pocket score-weighted SSC and leveraged by treating independently the d-pocket subsets within each surface state.

The DTM method allows calculation of ensemble average pocket features at the fragment-centric level. Three primary pocket features are of particular interest: pocket score, pocket stability, and pocket integrity. Each of these features may be calculated at the full d-pocket level or at the sub d-pocket level, which is limited to within a specific surface state cluster, as described previously.

D-pocket score is calculated as the simple average pocket score of an ensemble of pockets. An individual pocket score is calculated as previously described. It is the non-polar weighted total alpha-space of the pocket. More intuitively, this score can be considered to approximate the curvature-weighted non-polar surface area of the pocket. This feature reflects the potential hydrophobic effect between the pocket and a structurally complementary chemical fragment, which serves as an approximation for potential binding affinity.

D-pocket stability relates to the likelihood of observing a representative of that particular d-pocket within a set of snapshots, taken to be either the full trajectory or the subset of snapshots defined by a surface state cluster. It is calculated as the percentage of total snapshots in which that d-pocket is detected. Finally, pocket integrity reflects the degree of variation observed in the set of pocket-lining atoms between individual fragment-centric pockets within a d-pocket ensemble. It is the average pairwise pocket similarity within the ensemble, which is calculated as the complement of the average pairwise pocket distance, using the same pocket distance metric as in DTM. This feature reflects the general structural integrity versus structural pliability of that d-pocket.

The methods described herein allows assessment of the similarity, on a spectrum, between a particular surface state cluster from simulation and an established surface state of interest, for example the crystallized apo state or the crystallized iPPI state. Once a protein has undergone DTM, the average distance is calculated between each pocket in the crystallized interface of interest and each d-pocket ensemble from the simulation. Each pocket from the crystal is assigned to the d-pocket that exhibits the lowest average distance, as long as that average distance is below the cutoff applied as the distance parameter for the original DTM clustering. Crystal pockets for which each average d-pocket distance falls outside this cutoff are considered to be unique pockets and are thus assigned to a unique d-pocket. The average distance between the crystal surface state and each surface state cluster from the simulation may be calculated directly using the distance metric from SSC, and the corresponding average similarity is calculated as the complement to the average distance.

In this manner, the DTM method along with SSC provides a framework from which to study the detailed structure and dynamics of the protein surface. The set of fragment-centric pockets presented at a PPI interface relates directly to the geometry of its complementary molecular binder. Using this information to cluster molecular dynamics trajectories informs a more diverse conformation selection for virtual screening, a more sensitive detection of transient binding opportunities, and a way to evaluate the performance of enhanced sampling methods.

The DTM and SSC methods also provides for a more rational interpretation of configuration clustering results since the detailed similarities and deviations between, as well as within, states can be traced directly to which fragment-centric pockets are conserved and which diverge. Pocket similarities within surface states highlight which sub-regions of the interface are most stable, which may be more reliably targetable for rational drug design. Assessment of pocket similarities across all surface states identifies globally stable anchoring points, which may be important for ligand or peptide recognition.

Ligand Fragment Centers (LFC) and Alpha Cluster Centers (ACC)

Virtual screening of ligand molecules against the protein surface can be performed by clustering the atoms within a ligand, using a similar average linkage clustering approach as is used to cluster alpha-atoms into alpha-clusters, into ligand fragment centers or LFCs. These LFCs can be structurally aligned to sets of alpha-cluster centers, ACCs at any region of the protein surface. A low root-mean-square deviation (RMSD) for the alignment of a number of LFCs and ACCs may indicate the potential for structural complementarity between the targeted surface region and the ligand being screened.

Beta-Atoms

Any alpha-cluster can be re-clustered individually using a complete linkage clustering criteria with a distance cutoff of about 1.4 angstrom in order to reduce the total number of alpha-atoms and to make the spatial distribution of alpha-atoms more "molecular". The resulting centers of these sub-clusters are taken to be beta-atom centers. And the collection of beta-atoms clustered from an alpha-cluster is considered a beta-cluster. Methodologically, beta-clusters are intended to fulfill the same role as alpha-clusters, but will represent a more accurate pseudo ligand molecule, which will not contain multiple alpha-atoms overlapping in an unmolecular fashion.

Figure 23:
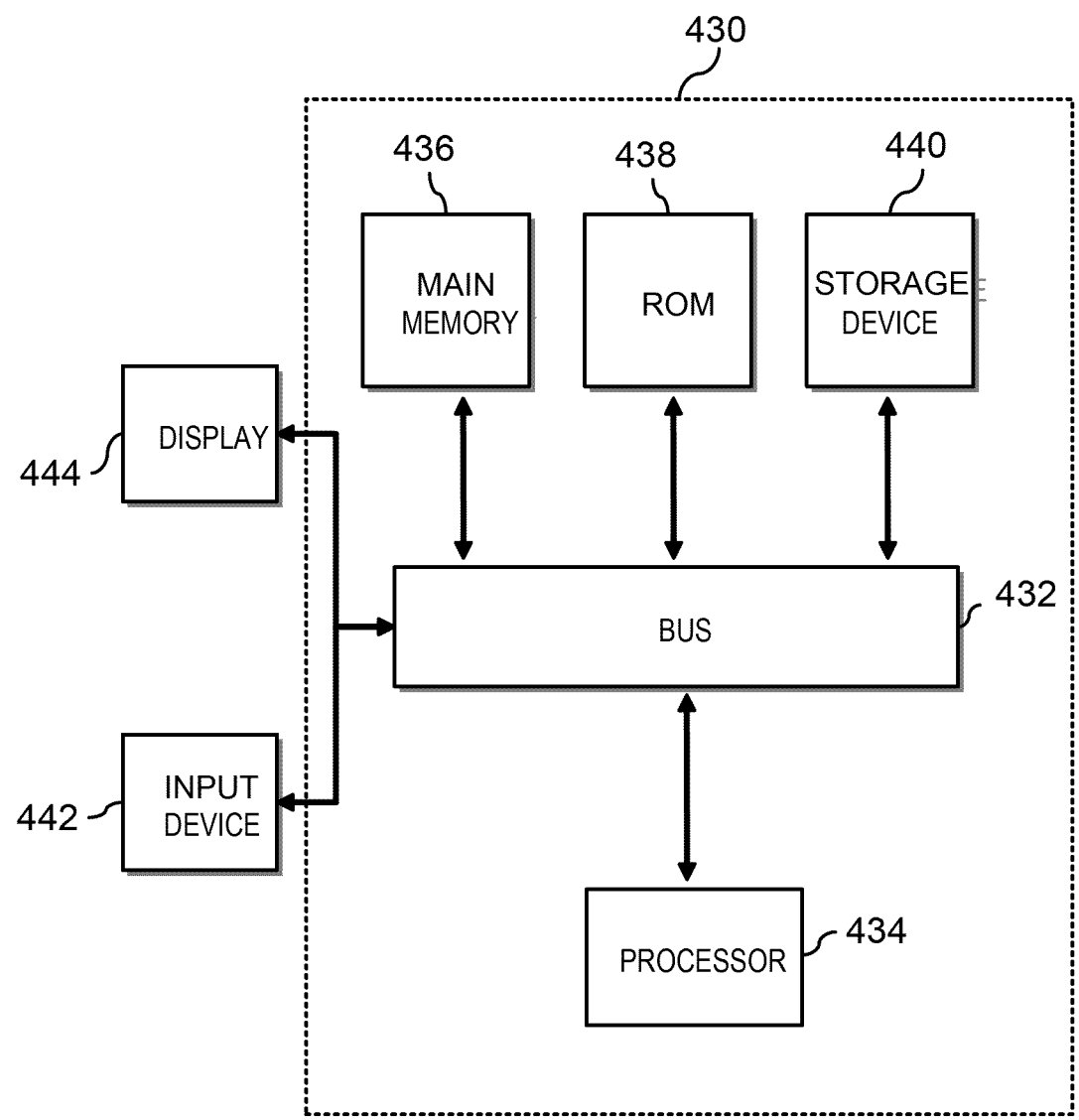
FIG. 23 is a schematic block diagram of a computing device which may be used to perform operations of any of the methods described herein.

Any of the methods defined herein, for example, the method 100, 200 can be executed and a stored on a computer readable medium and executed by a computing device specifically programmed to execute the instructions stored on the computer readable medium. FIG. 23 is a block diagram of a computing device 430 in accordance with an illustrative implementation. The computing device 430 can be included in the system 300 and configured to execute the pocket identification circuitry 304a and the pocket evaluation circuitry 304b, as described herein.

The computing device 430 includes a bus 432 or other communication component for communicating information and a processor 434 or processing circuit coupled to the bus 432 for processing information. The computing device 430 can also include one or more processors 434 or processing circuits coupled to the bus for processing information. The computing device 430 also includes a main memory 436, such as a random access memory (RAM) or other dynamic storage device, coupled to the bus 432 for storing information, and instructions to be executed by the processor 434. Main memory 436 can also be used for storing position information, temporary variables, or other intermediate information during execution of instructions by the processor 434. The computing device 430 may further include a read only memory (ROM) 438 or other static storage device coupled to the bus 432 for storing static information and instructions for the processor 434. A storage device 440, such as a solid-state device, magnetic disk or optical disk, is coupled to the bus 440 for persistently storing information and instructions.

The computing device 430 may be coupled via the bus 432 to a display 635, such as a liquid crystal display, or active matrix display, for displaying information to a user. An input device 442, such as a keyboard including alphanumeric and other keys, may be coupled to the bus 432 for communicating information and command selections to the processor 434. In another implementation, the input device 442 has a touch screen display 444. The input device 442 can include a cursor control, such as a mouse, a trackball, or cursor direction keys, for communicating direction information and command selections to the processor 434 and for controlling cursor movement on the display 444.

According to various implementations, the processes and methods described herein can be implemented by the computing device 430 in response to the processor 434 executing an arrangement of instructions contained in main memory 436. Such instructions can be read into main memory 436 from another non-transitory computer-readable medium, such as the storage device 440. Execution of the arrangement of instructions contained in main memory 436 causes the computing device 430 to perform the illustrative processes described herein. One or more processors in a multi-processing arrangement may also be employed to execute the instructions contained in main memory 436. In alternative implementations, hard-wired circuitry may be used in place of or in combination with software instructions to effect illustrative implementations. Thus, implementations are not limited to any specific combination of hardware circuitry and software.

Although an example computing device has been described in FIG. 23, implementations described in this specification can be implemented in other types of digital electronic circuitry, or in computer software, firmware, or hardware, including the structures disclosed in this specification and their structural equivalents, or in combinations of one or more of them.

Implementations described in this specification can be implemented in digital electronic circuitry, or in computer software, firmware, or hardware, including the structures disclosed in this specification and their structural equivalents, or in combinations of one or more of them. The implementations described in this specification can be implemented as one or more computer programs, i.e., one or more modules of computer program instructions, encoded on one or more computer storage media for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate components or media (e.g., multiple CDs, disks, or other storage devices). Accordingly, the computer storage medium is both tangible and non-transitory.

The operations described in this specification can be performed by a data processing apparatus on data stored on one or more computer-readable storage devices or received from other sources. The term "data processing apparatus" or "computing device" encompasses all kinds of apparatus, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

As used herein, the singular forms "a", "an" and "the" include plural referents unless the context clearly dictates otherwise. Thus, for example, the term "a member" is intended to mean a single member or a combination of members, "a material" is intended to mean one or more materials, or a combination thereof.

As used herein, the terms "about" and "approximately" generally mean plus or minus 10% of the stated value. For example, about 0.5 would include 0.45 and 0.55, about 10 would include 9 to 11, about 1000 would include 900 to 1100.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Other substitutions, modifications, changes and omissions may also be made in the design, operating conditions and arrangement of the various exemplary embodiments without departing from the scope of the present invention.

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

While this specification contains many specific implementation details, these should not be construed as limitations on the scope of any embodiments or of what may be claimed, but rather as descriptions of features specific to particular implementations of particular embodiments. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings and tables in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated in a single software product or packaged into multiple software products.

Thus, particular implementations of the invention have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A method for mapping and evaluating protein surfaces; comprises:
   performing, by a processor, a Voronoi tessellation of a protein structure;
   developing, by the processor, a Voronoi diagram of the surface of the protein, the Voronoi diagram including a plurality of Voronoi vertices;
   identifying, by the processor, all alpha-spheres at the surface of the protein, a center of the alpha-spheres corresponding to the Voronoi vertices;
   filtering, by the processor, the alpha-spheres based on radius, the filtering including removing alpha-spheres having a radius below a minimum radius and above a maximum radius;
   clustering, by the processor, remaining alpha-spheres into alpha-clusters, the alpha-clusters comprising localized pockets on the protein structure clustered using a linkage algorithm with optimized clustering parameters;
   selecting, by the processor, a plurality of alpha-clusters, the plurality of alpha-clusters each comprising an individual pocket of the localized pockets on the protein structure and each of the localized pockets on the protein is proximate to a protein-protein interaction; and
   displaying, on a graphical user interface, at least one of the individual pockets of the localized pockets on the protein structure to a user.

2. The method of claim 1, wherein the minimum radius is 3.2 angstroms, and wherein the maximum radius is 5.4 angstroms.

3. The method of claim 1, wherein the linkage algorithm includes one of an average linkage algorithm, a complete linkage algorithm, a density-based algorithm, or a density peak algorithm.

4. The method of claim 3, wherein the linkage algorithm is the average linkage algorithm and the average linkage algorithm uses a pair wise alpha-sphere Euclidean distance matrix to generate a hierarchical dendrogram of the alpha-spheres according to an average-linkage criterion, or maximum mean distance between elements of any single cluster.

5. The method of claim 4, wherein the average linkage algorithm defines a clustering parameter corresponding to a maximum average linkage distance within alpha-clusters and is between 4.6 angstrom and 4.8 angstrom to separate the dendrogram of the alpha-spheres into a plurality of alpha-clusters.

6. The method of claim 5, wherein an average number of side chains of the chemical fragment which can be engaged by each pocket of the protein is 1.

7. A method for evaluating a pocket of a protein, comprises:
   determining sets of alpha-sphere contact atoms in a plurality of localized regions of the pocket, the contact atoms including four atoms of the protein that are equidistant to a corresponding alpha-sphere, the alpha-sphere representing a single interaction point;
   performing a Delaunay triangulation of the four contact atoms of each interaction point;
   determining a plurality of alpha-spaces of each interaction point, each alpha-space corresponding to a volume of a region defined by the Delaunay triangulation of the contact atoms of each interaction point;
   determining an alpha-atom of each interaction point, the alpha-atom comprising a theoretical atom having a radius of 1.8 angstroms in contact with a surface of each of the contact atoms in a localized region of the pocket;
   determining an alpha-atom contact surface area (ACSA) of the pocket;
   ranking the pocket to determine a pocket score, the pocket score corresponding to a nonpolar-weighted alpha-space volume;
   determining a pocket-fragment complementarity by discretely evaluating whether there is overlap for individual alpha-atoms;
   matching pockets between various conformations of the protein;
   identifying an optimal chemical fragment for binding to the pocket of the protein in a protein-protein interaction; and
   displaying the optimal chemical fragment to a user.

8. The method of claim 7, wherein each of the plurality of alpha-spaces does not overlap with another of the plurality of alpha-spaces and further wherein the plurality of alpha-spaces are positioned face-to-face within the pocket to define a contiguous volume and wherein a sum of all the alpha-spaces correlates with a combination of the surface area and curvature of the entire pocket.

9. The method of claim 7, wherein alpha-atoms of each localized region of the pocket form an overlapping alpha-cluster, an outline of the alpha-cluster representing a shape and size of a chemical fragment complimentary to the pocket.

10. The method of claim 9, wherein determining the ACSA comprises:
    taking a difference between a first contact surface of the contact atoms of each interaction point before binding to the alpha-cluster, and a second contact surface of the contact atoms of each interaction point after binding to the alpha-cluster.

11. The method of claim 7, wherein the pocket score is determined using a formula selected from formula I-A, formula I-B, formula II, and formula III wherein:

$$\text{score}_J = \sum_{\alpha \in J} \left( V_\alpha * \frac{\sum_{i \in \alpha} (ACSA_{i,J} * NP_{i,J})}{\sum_{i \in \alpha} (ACSA_{i,J})} \right) \quad \text{Formula I-A}$$

where:

$\alpha$ is an alpha-space within the pocket J with volume $V_\alpha$, $ACSA_{i,J}$ is the alpha-atom contact surface area for atom i calculated using alpha-cluster J and $NP_{i,J}$ is the binary polarity status for atom i in pocket J;

$$\text{score}_J = \sum_{\alpha \in J} (V_\alpha) \quad \text{Formula I-B}$$

where:

$\alpha$ is an alpha-space within the pocket J with volume $V_\alpha$;

$$\text{score}_J = \frac{\sum_{\alpha \in J}\left(V_\alpha * \frac{\sum_{i \in \alpha}(ACSA_{i,J} * NP_{i,J})}{\sum_{i \in \alpha}(ACSA_{i,J})}\right)}{\sum_{\alpha \in J}(V_\alpha)} \quad \text{Formula I-C}$$

where:

$\alpha$ is an alpha-space within the pocket J with volume $V_\alpha$, $ACSA_{i,J}$ is the alpha-atom contact surface area for atom i calculated using alpha-cluster J and $NP_{i,J}$ is the binary polarity status for atom i in pocket J;

$$\% \, occ_J = \frac{\sum_{\alpha \in J}(V_\alpha * O_\alpha)}{\sum_{\alpha \in J} V_\alpha} \quad \text{Formula II}$$

where:

% $occ_J$ is the percentage of the interaction space of pocket J that is occupied by the bound ligand, $\alpha$ is an alpha-space within pocket J with volume $V_\alpha$, and $O\alpha$ is the binary occupation status of $\alpha$; and $$sim_{J,K} = \frac{\sum_{i \in (J \cap K)}(ACSA_{i,J} + ACSA_{i,K})}{\sum_{i \in J} ACSA_{i,J} + \sum_{i \in K} ACSA_{i,K}} \quad \text{Formula III}$$

where:

$sim_{J,K}$ is a similarity matrix between a first conformation J of the pocket and a second conformation K of the pocket.

12. The method of claim 11, wherein pocket score is determined using formula II and an alpha-space is at least partially occupied when a distance between a center of the alpha-atom and a center of the overlapping chemical fragment atom is less than 1.6 angstroms.

13. The method of claim 7, wherein the alpha-space is unoccupied when the distance between the center of the alpha-atom and the center of the overlapping chemical fragment atom is greater than 1.6 angstroms.

14. The method of claim 7, wherein at least a portion of a chemical fragment is extended to overlap the alpha-atom associated with an unoccupied alpha-space to optimize pocket occupation.

15. The method of claim 11, wherein pocket score is determined using a formula III and a similarity cut-off for matching the first conformation J of the pocket and a second conformation K of the pocket is 30%.

16. The method of claim 7, further comprising:
determining the pocket score using only the alpha-spaces associated with the alpha-atoms that are occupied by a chemical fragment.

17. The method of claim 7, further comprising:
determining a contact score associated with an interacting chemical fragment, the contact score comprising a sum of the alpha-spaces of the protein that are occupied by atoms from the chemical fragment.

18. The method of claim 17, further comprising;
inverse mapping of pockets in the ligand surface; and
adding to fragment contact score the decomposed alpha-space associated with alpha-atoms within pockets defined by the ligand surface and occupied by the protein target atoms.

19. The method of claim 18, further comprising;
classifying the contact interactions by the respective pharmacophore identities of the pocket-atoms from the protein and/or the ligand; and
grouping contact scores according to predefined sets of pharmacophore combinations.

* * * * *

UNITED STATES PATENT AND TRADEMARK OFFICE
CERTIFICATE OF CORRECTION

| | |
|---|---|
| PATENT NO. | : 11,538,553 B2 |
| APPLICATION NO. | : 15/559719 |
| DATED | : December 27, 2022 |
| INVENTOR(S) | : Yingkai Zhang and David Rooklin |

It is certified that error appears in the above-identified patent and that said Letters Patent is hereby corrected as shown below:

In the Specification

Column 1, following after the "Cross Reference to Related Applications" sub-heading and paragraph, add new sub-heading and paragraph:
STATEMENT OF GOVERNMENT INTEREST
"This invention was made with government support under R01 GM073943, and R01 GM079223 awarded by the National Institutes of Health. The government has certain rights in the invention."

Signed and Sealed this
Twenty-sixth Day of August, 2025

Coke Morgan Stewart
*Acting Director of the United States Patent and Trademark Office*